United States Patent
Carpino

(10) Patent No.: US 6,686,359 B2
(45) Date of Patent: Feb. 3, 2004

(54) GROWTH HORMONE SECRETAGOGUES

(75) Inventor: Philip A. Carpino, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/313,495

(22) Filed: Dec. 6, 2002

(65) Prior Publication Data

US 2003/0130284 A1 Jul. 10, 2003

Related U.S. Application Data

(62) Division of application No. 09/989,040, filed on Nov. 21, 2001, now Pat. No. 6,559,150, which is a division of application No. 09/377,326, filed on Aug. 18, 1999, now Pat. No. 6,358,951.
(60) Provisional application No. 60/097,502, filed on Aug. 21, 1998.

(51) Int. Cl.[7] ............... C07D 471/04; C07D 241/86; C07D 487/04; A61K 31/445; A61K 31/519
(52) U.S. Cl. .............. 514/249; 514/303; 544/350; 546/120
(58) Field of Search ................. 514/248, 249, 514/303, 230.5; 544/236, 91, 350; 546/120

(56) References Cited

U.S. PATENT DOCUMENTS

| 4,411,890 A | 10/1983 | Momany | 424/177 |
|---|---|---|---|
| 6,251,902 B1 | 6/2001 | Carpino et al. | 514/249 |
| 6,358,951 B1 | 3/2002 | Carpino | 514/248 |

FOREIGN PATENT DOCUMENTS

| WO | WO9411012 | 5/1994 | A61K/37/00 |
|---|---|---|---|
| WO | WO9413696 | 6/1994 | C07K/5/02 |
| WO | WO9638471 | 12/1996 | C07K/5/02 |
| WO | WO9709060 | 3/1997 | A61K/38/27 |
| WO | WO9724369 | 7/1997 | C07K/5/06 |
| WO | WO9803473 | 1/1998 | C07C/237/16 |
| WO | WO9810653 | 3/1998 | A01N/43/08 |
| WO | WO9825897 | 6/1998 | C07D/209/04 |
| WO | WO9858947 | 12/1998 | C07K/5/023 |

OTHER PUBLICATIONS

Jorgensen, et al., "Beneficial Effects of Growth Hormone Treatment in GH–Deficient Adults", *The Lancet*, pp. 1221–1224 (1989).

Richelsen, et al., "Growth hormone treatment of obese women in 5 wk: effect on body composition and adipose tissue LPL activity", *Am. J. Physiol.* 266, pp. E211–E216 (1994).

Rudman, et al. "Effects of Human Growth Hormone on Body Composition in Elderly Men", *Horm. Res.* 36(1), pp. 73–81 (1991).

Gertz, et al., "L–692,429, a Nonpeptide Growth Hormone (GH) Secreagogue, Reverses Glucocorticoid Suppression of GH Secretion", *Journ. of Clin. Endocr. And Metabolism* 79(3), pp. 745–749, (1994).

Aloi, et al., "Neuroendocrine Responses to a Novel Growth Hormone Secretagogue, L–692,429, in Healthy Older Subjects", *Journ. of Clin. Endocrin. And Metabolism* 79(4), pp. 943–949 (1994).

Maccario, et al. "Metabolic Modulation of the Growth Hormone–Releasing Activity of Hexarelin in Man", *Metabolism* 44(1), pp. 134–138 (1995).

Jacks, et al., "Effects of acute and repeated intravenous administration of L–692,585, a novel non–peptidyl growth hormone secretagogue, on plasma growth hormone, IGF–1, ACTH, cortisol, prolactin, insulin, and thyroxine levels in beagles", *Journal of Endocrinology* 143, pp. 399–406 (1994).

Arvat, et al., "Arginine and Growth Hormone–Releasing Hormone Restore the Blunted Growth Hormone–Releasing Activity of Hexarelin in Elderly Subjects", *Journ. of Clin. Endocrin. And Metabolism* 79(50), pp. 1440–1443 (1994).

*Primary Examiner*—Deepak Rao
(74) *Attorney, Agent, or Firm*—Peter C. Richardson; Gregg C. Benson; John A. Wichtowski

(57) ABSTRACT

This invention is directed to compounds of the formula

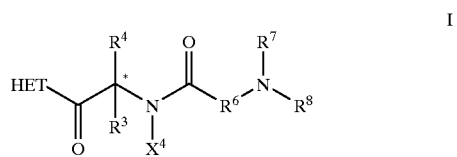

I and the pharmaceutically-acceptable salts thereof, where the substituents are as defined in the specification, which are growth hormone secretogogues and which increase the level of endogenous growth hormone. The compounds of this invention are useful for the treatment and prevention of osteoporosis, congestive heart failure, frailty associated with aging, obesity; accelerating bone fracture repair, attenuating protein catabolic response after a major operation, reducing cachexia and protein loss due to chronic illness, accelerating wound healing, or accelerating the recovery of burn patients or patients having undergone major surgery; improving muscle strength, mobility, maintanence of skin thickness, metabolic homeostasis or renal homeostasis. The compounds of the present invention are also useful in treating osteoporosis when used in combination with: a bisphosphonate compound such as alendronate; estrogen, premarin, and optionally progesterone; a $\beta_3$ adrenergic receptor agonist; an estrogen agonist or antagonist; or calcitonin, and pharmaceutical compositions useful therefor. Further, the present invention is directed to pharmaceutical compositions useful for increasing the endogenous production or release of growth hormone in a human or other animal which comprises an effective amount of a compound of the present invention and a growth hormone secretagogue selected from GHRP–6, Hexarelin, GHRP–1, growth hormone releasing factor (GRF), IGF–1, IGF–2 or B-HT920.

20 Claims, No Drawings

GROWTH HORMONE SECRETAGOGUES

CROSS REFERENCE TO RELATED APPLICATIONS

This is a divisional application of U.S. Ser. No. 09/989,040, filed Nov. 21, 2001, now U.S. Pat. No. 6,559,150, which is a divisional application of U.S. Ser. No. 09/377,326, filed Aug. 18, 1999, now U.S. Pat. No. 6,358,951, which claims the benefit of U.S. provisional application No. 60/097,502, filed Aug. 21, 1998.

This invention relates to dipeptide compounds, which are growth hormone secretagogues and are useful for the treatment and prevention of musculoskeletal frailty including osteoporosis.

BACKGROUND OF THE INVENTION

Growth hormone (GH), which is secreted from the pituitary gland, stimulates growth of all tissues of the body that are capable of growing. In addition, growth hormone is known to have the following basic effects on the metabolic processes of the body:

1. Increased rate of protein synthesis in substantially all cells of the body;
2. Decreased rate of carbohydrate utilization in cells of the body; and
3. Increased mobilization of free fatty acids and use of fatty acids for energy.

Deficiency in growth hormone results in a variety of medical disorders. In children, it causes dwarfism. In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological well-being.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in an expensive product, and carried with it the risk that a disease associated with the source of the pituitary gland could be transmitted to the recipient of the growth hormone (e.g., Jacob-Creutzfeld disease). Recently, recombinant growth hormone has become available which, while no longer carrying any risk of disease transmission, is still a very expensive product which must be given by injection or nasal spray.

Most GH deficiencies are caused by defects in GH release, not primary defects in pituitary synthesis of GH. Therefore, an alternative strategy for normalizing serum GH levels is by stimulating its release from somatotrophs. Increasing GH secretion can be achieved by stimulating or inhibiting various neurotransmitter systems in the brain and hypothalamus. As a result, the development of synthetic growth hormone-releasing agents to stimulate pituitary GH secretion are being pursued, and may have several advantages over expensive and inconvenient GH replacement therapy. By acting along physiologic regulatory pathways, the most desirable agents would stimulate pulsatile GH secretion, and excessive levels of GH that have been associated with the undesirable side effects of exogenous GH administration would be avoided by virtue of intact negative feedback loops.

Physiologic and pharmacologic stimulators of GH secretion, which include arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GHRF) or an unknown endogenous growth hormone-releasing hormone or all of these.

Obesity is a major risk factor for diabetes, and a large fraction of NIDDM patients are obese. Both conditions are characterized by elevated circulating insulin levels and suppressed GH levels. GH treatment of GH-deficient adults (Jorgensen, J. O. L., et al., Lancet 1:1221 (1989)), obese women (Richelsen, B., et al., Am J Physiol, 266:E211 (1994)) and elderly men (Rudman, D., et al, Horm Res 36 (Suppl 1):73 (1991)) has been shown to produce increases in lean body, hepatic and muscle mass while decreasing fat mass. Thus, GH therapy for obesity would seem attractive except for the diabetogenic effects of GH.

An alternative to exogenous GH administration is therapy that stimulates endogenous GH secretion. It has been shown that a substantial pituitary reserve of GH is present in pituitary-intact GH-deficient patients and the elderly so that decreased serum GH levels are due to hyposecretion.

Hyposecretion of GH in several clinical settings (obesity, aging, glucocorticoid suppression) is relatively resistant to stimulation by GHRH (Gertz, B. J., et al., J Clin Endocrinol Metab, 79:745 (1994); Arvat, E., et al., J Clin Endocrinol Metab, 79:1440 (1994); Maccario, M., et al., Metabolism, 44:134 (1995)). In contrast, administration of a growth hormone releasing peptide (GHRP) or combined administration of growth hormone releasing hormone (GHRH) and a GHRP in these patients can elicit a robust GH response (Aloi, J. A., et al., J Clin Endocrinol Metab, 79:943; (1994)). Single dose studies of GHRPs have demonstrated the absence of an acute effect on circulating insulin or glucose levels. Insulin and glucose have generally not been monitored in chronic studies except to document the absence of unfavorable changes (Jacks, T., et al., J Endocrinol. 143:399 (1993)).

Prior to the present invention, the use of GHRPs or GHRP mimetics to improve glycemic control has not specifically been explored. The method of treating insulin resistance in a mammal comprising the administration of a compound of Formula I of this invention is practiced preferentially in patients who have a functional hypothalamic-pituitary axis capable of GH secretory responses to GHRPs and who have pancreatic beta-cells capable of secreting insulin.

Other compounds have been developed which stimulate the release of endogenous growth hormone such as analogous peptidyl compounds related to GHRF or the peptides of U.S. Pat. No. 4,411,890. These peptides, while considerably smaller than growth hormones, are still susceptible to various proteases. As with most peptides, their potential for oral bioavailability is low.

International Patent Application Publication No. WO 94/13696 refers to certain spiropiperidines and homologues which promote release of growth hormone. Preferred compounds described therein are of the general structure shown below:

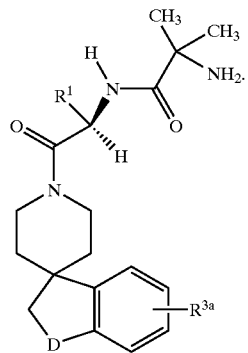

International Patent Application Publication No. WO 94/11012 refers to certain dipeptides that promote release of growth hormone. These dipeptides have the general structure:

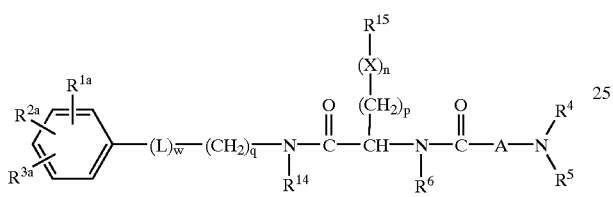

where L is

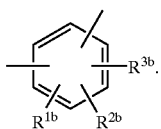

The compounds of WO 94/11012 and WO 94/13696 are disclosed to be useful in the treatment of osteoporosis in combination with parathyroid hormone or a bisphosphonate.

International Patent Application Publication No. WO 97/09060 discloses the use of growth hormone releasing hormone or a functional analog thereof in the treatment of insulin resistance in mammals.

International Patent Application Publication No. WO98/10653 discloses compounds of the formula:

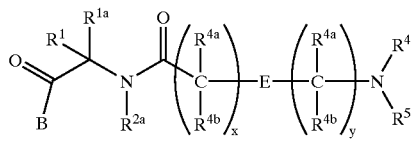

wherein the variables are defined as set forth therein.

International Patent Application Publication No. WO97/24369 discloses growth hormone secretagogue compounds of the formula:

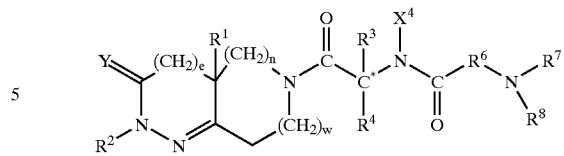

wherein $R^6$ is a bond or is

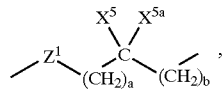

and the remaining variables are as defined as set forth therein.

SUMMARY OF THE INVENTION

This invention is directed to compounds of the Formula I:

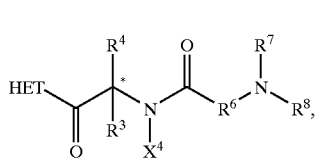

or stereoisomeric mixtures thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug,
wherein:
HET is a heterocyclic moiety selected from the group consisting of

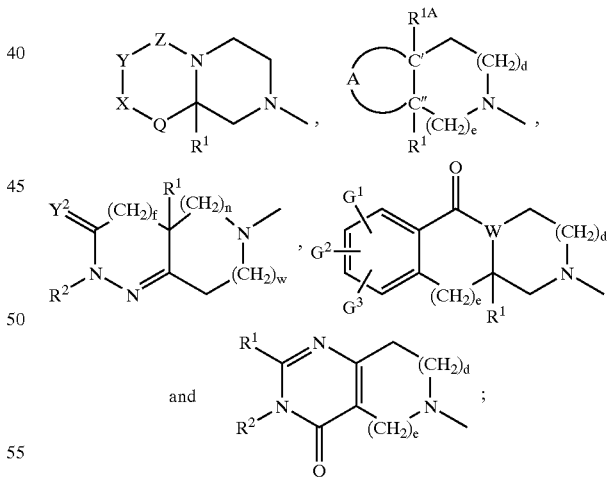

d is 0, 1 or 2;
e is 1 or 2;
f is 0 or 1;
n and w are 0, 1 or 2, provided that n and w cannot both be 0 at the same time;
$Y^2$ is oxygen or sulfur;
A is a divalent radical, where the left hand side of the radical as shown below is connected to C" and the right hand side of the radical as shown below is connected to C', selected from the group consisting of —NR²—C(O)—NR²—, —NR²—S(O)₂—NR²—,
—O—C(O)—NR²—, —NR²—C(O)—O—,
—C(O)—NR²—C(O)—, —C(O)—NR²—C(R⁹R¹⁰)—, —C(R⁹R¹⁰)—NR²—C(O)—,
—C(R⁹R¹⁰)—C(R⁹R¹⁰)—C(R⁹R¹⁰)—, —S(O)₂—C(R⁹R¹⁰)—C(R⁹R¹⁰)—, —C(R⁹R¹⁰)—O—C(O)—,
—C(R⁹R¹⁰)—O—C(R⁹R¹⁰)—, —NR²—C(O)—C(R⁹R¹⁰)—, —O—C(O)—C(R⁹R¹⁰)—, —C(R⁹R¹⁰)—C(O)—NR²—, —C(O)—NR²—C(O)—,
—C(R⁹R¹⁰)—C(O)—O—, —C(O)—NR²—C(R⁹R¹⁰)—C(R⁹R¹⁰)—, —C(O)—O—C(R⁹R¹⁰)—,
—C(R⁹R¹⁰)—C(R⁹R¹⁰)—C(R⁹R¹⁰)—C(R⁹R¹⁰)—,
—S(O)₂—NR²—C(R⁹R¹⁰)—C(R⁹R¹⁰)—,
—C(R⁹R¹⁰)—C(R⁹R¹⁰)—NR²—C(O)—,
—C(R⁹R¹⁰)—C(R⁹R¹⁰)—O—C(O)—, —NR²—C(O)—C(R⁹R¹⁰)—C(R⁹R¹⁰)—, —NR²—S(O)₂—C(R⁹R¹⁰)—C(R⁹R¹⁰)—, —O—C(O)—C(R⁹R¹⁰)—C(R⁹R¹⁰)—, —C(R⁹R¹⁰)—C(R⁹R¹⁰)—C(O)—NR²—,
—C(R⁹R¹⁰)—C(R⁹R¹⁰)—C(O)—, —C(R⁹R¹⁰)—NR²—C(O)—O—, —C(R⁹R¹⁰)—O—C(O)—NR²—, —C(R⁹R¹⁰)—NR²—C(O)—NR²—, —NR²—C(O)—O—C(R⁹R¹⁰)—, —NR²—C(O)—NR²—C(R⁹R¹⁰)—,
—NR²—S(O)₂—NR²—C(R⁹R¹⁰)—, —O—C(O)—NR²—C(R⁹R¹⁰)—, —C(O)—N=C(R¹¹)—NR²—,
—C(O)—NR²—C(R¹¹)=N—, —C(R⁹R¹⁰)—NR¹²—C(R⁹R¹⁰)—, —NR¹²—C(R⁹R¹⁰)—, —NR¹²—C(R⁹R¹⁰)—C(R⁹R¹⁰)—, —C(O)—O—C(R⁹R¹⁰)—C(R⁹R¹⁰)—, —NR²—C(R¹¹)=N—C(O)—,
—C(R⁹R¹⁰)—C(R⁹R¹⁰)—N(R¹²)—, —C(R⁹R¹⁰)—NR¹²—, —N=C(R¹¹)—NR²—C(O)—,
—C(R⁹R¹⁰)—C(R⁹R¹⁰)—NR²—S(O)₂—,
—C(R⁹R¹⁰)—C(R⁹R¹⁰)—S(O)₂—NR²—,
—C(R⁹R¹⁰)—C(R⁹R¹⁰)—C(O)—O—, —C(R⁹R¹⁰)—S(O)₂—C(R⁹R¹⁰)—, —C(R⁹R¹⁰)—C(R⁹R¹⁰)—S(O)₂—, —O—C(R⁹R¹⁰)—C(R⁹R¹⁰)—,
—C(R⁹R¹⁰)—C(R⁹R¹⁰)—O—, —C(R⁹R¹⁰)—C(O)—C(R⁹R¹⁰)—, —C(O)—C(R⁹R¹⁰)—C(R⁹R¹⁰)— and —C(R⁹R¹⁰)—NR²—S(O)₂—NR²—;

Q is a covalent bond or CH₂;
W is CH or N;
X is CR⁹R¹⁰, C=CH₂ or C=O;
Y is CR⁹R¹⁰, O or NR²;
Z is C=O, C=S or S(O)₂;
G¹ is hydrogen, halo, hydroxy, nitro, amino, cyano, phenyl, carboxyl, —CONH₂, —(C₁-C₄)alkyl optionally independently substituted with one or more phenyl, one or more halogens or one or more hydroxy groups, —(C₁-C₄)alkoxy optionally independently substituted with one or more phenyl, one or more halogens or one or more hydroxy groups, —(C₁-C₄)alkylthio, phenoxy, —COO(C₁-C₄)alkyl, N,N-di-(C₁-C₄)alkylamino, —(C₂-C₆)alkenyl optionally independently substituted with one or more phenyl, one or more halogens or one or more hydroxy groups, —(C₂-C₆)alkynyl optionally independently substituted with one or more phenyl, one or more halogens or one or more hydroxy groups, —(C₃-C₆)cycloalkyl optionally independently substituted with one or more (C₁-C₄)alkyl groups, one or more halogens or one or more hydroxy groups, —(C₁-C₄)alkylamino carbonyl or di-(C₁-C₄)alkylamino carbonyl;
G² and G³ are each independently selected from the group consisting of hydrogen, halo, hydroxy, —(C₁-C₄)alkyl optionally independently substituted with one to three halogens and —(C₁-C₄)alkoxy optionally independently substituted with one to three halogens;
R¹ is hydrogen, —CN, —(CH₂)$_q$N(X⁶)C(O)X⁶, —(CH₂)$_q$N(X⁶)C(O)(CH₂)$_t$—A¹, —(CH₂)$_q$N(X⁶)S(O)₂(CH₂)$_t$—A¹,
—(CH₂)$_q$N(X⁶)S(O)₂X⁶, —(CH₂)$_q$N(X⁶)C(O)N(X⁶)(CH₂)$_t$—A¹, —(CH₂)$_q$N(X⁶)C(O)N(X⁶)(X⁶), —(CH₂)$_q$C(O)N(X⁶)(X⁶), —(CH₂)$_q$C(O)N(X⁶)(CH₂)$_t$—A¹,
—(CH₂)$_q$C(O)OX⁶, —(CH₂)$_q$C(O)O(CH₂)$_t$—A¹,
—(CH₂)$_q$OX⁶, —(CH₂)$_q$OC(O)X⁶, —(CH₂)$_q$OC(O)(CH₂)$_t$—A¹, —(CH₂)$_q$OC(O)N(X⁶)(CH₂)$_t$—A¹,
—(CH₂)$_q$OC(O)N(X⁶)(X⁶), —(CH₂)$_q$C(O)X⁶,
—(CH₂)$_q$C(O)(CH₂)$_t$—A¹, —(CH₂)$_q$N(X⁶)C(O)OX⁶,
—(CH₂)$_q$N(X⁶)S(O)₂N(X⁶)(X⁶), —(CH₂)$_q$S(O)$_m$X⁶,
—(CH₂)$_q$S(O)$_m$(CH₂)$_t$—A¹, —(C₁-C₁₀)alkyl,
—(CH₂)$_t$—A¹, —(CH₂)$_q$—(C₃-C₇)cycloalkyl,
—(CH₂)$_q$—Y¹—(C₁-C₆)alkyl, —(CH₂)$_q$—Y¹—(CH₂)$_t$—A¹ or —(CH₂)$_q$—Y¹—(CH₂)$_t$—(C₃-C₇)cycloalkyl;
where the alkyl and cycloalkyl groups in the definition of R¹ are optionally substituted with (C₁-C₄)alkyl, hydroxy, (C₁-C₄)alkoxy, carboxyl, —CONH₂, —S(O)$_m$(C₁-C₆)alkyl, —CO₂(C₁-C₄)alkyl ester, 1H-tetrazol-5-yl or 1, 2 or 3 fluoro groups;
Y¹ is O, S(O)$_m$, —C(O)NX⁶—, —CH=CH—, —C≡C—, —N(X⁶)C(O)—, —C(O)NX⁶—, —C(O)O—, —OC(O)N(X⁶)— or —OC(O)—;
q is 0, 1, 2, 3 or 4;
t is 0, 1, 2 or 3;
said (CH₂)$_q$ group and (CH₂)$_t$ group in the definition of R¹ are optionally independently substituted with hydroxy, (C₁-C₄)alkoxy, carboxyl, —CONH₂, —S(O)$_m$(C₁-C₆)alkyl, —CO₂(C₁-C₄)alkyl ester, 1H-tetrazol-5-yl, 1, 2 or 3 fluoro groups or 1 or 2 (C₁-C₄)alkyl groups;
R$^{1A}$ is selected from the group consisting of hydrogen, F, Cl, Br, I, (C₁-C₆)alkyl, phenyl(C₁-C₃)alkyl, pyridyl(C₁-C₃)alkyl, thiazolyl(C₁-C₃)alkyl and thienyl(C₁-C₃)alkyl, provided that R$^{1A}$ is not F, Cl, Br or I when a heteroatom is vicinal to C";
R², for each occurrence, is hydrogen, (C₁-C₈)alkyl, —(C₀-C₃)alkyl-(C₃-C₈)cycloalkyl, —(C₁-C₄)alkyl-A¹ or A¹;
where the alkyl groups and the cycloalkyl groups in the definition of R² are optionally substituted with hydroxy, —C(O)OX⁶, —C(O)N(X⁶)(X⁶), —N(X⁶)(X⁶), —S(O)$_m$(C₁-C₆)alkyl, —C(O)A¹, —C(O)(X⁶), CF₃, CN or 1, 2 or 3 independently selected halogens;
R³ is selected from the group consisting of A¹, (C₁-C₁₀)alkyl, —(C₁-C₆)alkyl-A¹, —(C₁-C₆)alkyl-(C₃-C₇)cycloalkyl, —(C₁-C₅)alkyl-X¹-(C₁-C₅)alkyl, —(C₁-C₅)alkyl-X¹—(C₀-C₅)alkyl-A¹ and —(C₁-C₅)alkyl-X¹—(C₁-C₅)alkyl-(C₃-C₇)cycloalkyl;
where the alkyl groups in the definition of R³ are optionally substituted with —S(O)$_m$(C₁-C₆)alkyl, —C(O)OX³, 1, 2, 3, 4 or 5 independently selected halogens or 1, 2 or 3 independently selected —OX³ groups;
X¹ is O, S(O)$_m$, —N(X²)C(O)—, —C(O)N(X²)—, —OC(O)—, —C(O)O—, —CX²=CX²—, —N(X²)C(O)O—, —OC(O)N(X²)— or —C≡C—;
R⁴ is hydrogen, (C₁-C₆)alkyl or (C₃-C₇)cycloalkyl, or R⁴ is taken together with R³ and the carbon atom to which they are attached and form (C₅-C₇)cycloalkyl, (C₅-C₇)cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

$R^6$ is $-(CR^aR^b)_a-E-(CR^aR^b)_b-$, where the $-(CR^aR^b)_a-$ group is attached to the carbonyl carbon of the amide group of the compound of formula I and the $-(CR^aR^b)_b$ group is attached to the terminal nitrogen atom of the compound of formula I;

E is $-O-$, $-S-$, $-CH=CH-$ or an aromatic moiety selected from

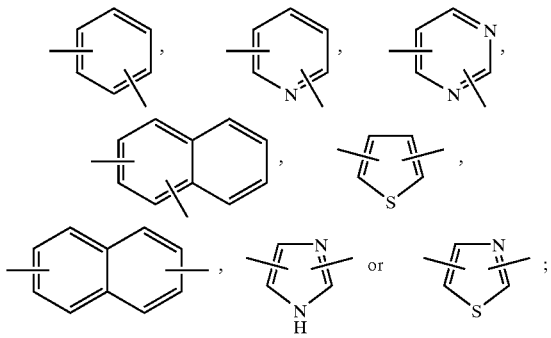

said aromatic moiety in the definition of E optionally substituted with up to three halo, hydroxy, $-N(R^c)(R^c)$, $(C_1-C_6)$alkyl or $(C_1-C_6)$alkoxy;

$R^a$ and $R^b$ are, for each occurrence, independently hydrogen, $(C_1-C_6)$alkyl, trifluoromethyl, phenyl or monosubstituted $(C_1-C_6)$alkyl where the substituents are imidazolyl, naphthyl, phenyl, indolyl, p-hydroxyphenyl, $-OR^c$, $S(O)_mR^c$, $C(O)OR^c$, $(C_3-C_7)$cycloalkyl, $-N(R^c)(R^c)$, $-C(O)N(R^c)R^c$, or $R^a$ or $R^b$ may independently be joined to one or both of $R^7$ or E (where E is other than O, S or $-CH=CH-$) to form an alkylene bridge between the terminal nitrogen and the alkyl portion of the $R^a$ or $R^b$ and the $R^7$ or E group, wherein the bridge contains 1 to 8 carbon atoms; or $R^a$ and $R^b$ may be joined to one another to form a $(C_3-C_7)$cycloalkyl;

$R^c$, for each occurrence, is independently hydrogen or $(C_1-C_6)$alkyl; a and b are independently 0, 1, 2 or 3, with the proviso that if E is $-O-$ or $-S-$, y is other than 0 or 1 and with the further proviso that if E is $-CH=CH-$, y is other than 0;

$R^7$ and $R^8$ are each independently hydrogen or optionally substituted $(C_1-C_6)$alkyl;

where the optionally substituted $(C_1-C_6)$alkyl in the definition of $R^7$ and $R^8$ is optionally independently substituted with $A^1$, $-C(O)O-(C_1-C_6)$alkyl, $-S(O)_m(C_1-C_6)$alkyl, 1 to 5 halogens, 1 to 3 hydroxy groups, 1 to 3 $-O-C(O)(C_1-C_{10})$alkyl groups or 1 to 3 $(C_1-C_6)$alkoxy groups; or $R^7$ and $R^8$ can be taken together to form $-(CH_2)_r-L-(CH_2)_r-$;

where L is $C(X^2)(X^2)$, $S(O)_m$ or $N(X^2)$;

$R^9$ and $R^{10}$ are each independently selected from the group consisting of hydrogen, fluoro, hydroxy and $(C_1-C_5)$alkyl optionally independently substituted with 1-5 halogens;

$R^{11}$ is selected from the group consisting of $(C_1-C_5)$alkyl and phenyl optionally substituted with 1-3 substituents each independently selected from the group consisting of $(C_1-C_5)$alkyl, halo and $(C_1-C_5)$alkoxy;

$R^{12}$ is selected from the group consisting of $(C_1-C_5)$ alkylsulfonyl, $(C_1-C_5)$alkanoyl and $(C_1-C_5)$alkyl where the alkyl portion is optionally independently substituted by 1–5 halogens;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $-OX^6$, $-C(O)N(X^6)(X^6)$, $-C(O)OX^6$, oxo, $(C_1-C_6)$ alkyl, nitro, cyano, benzyl, $-S(O)_m(C_1-C_6)$alkyl, 1H-tetrazol-5-yl, phenyl, phenoxy, phenylalkyloxy, halophenyl, methylenedioxy, $-N(X^6)(X^6)$, $-N(X^6)C(O)(X^6)$, $-S(O)_2N(X^6)(X^6)$, $-N(X^6)S(O)_2$-phenyl, $-N(X^6)S(O)_2X^6$, $-CONX^{11}X^{12}$, $-S(O)_2NX^{11}X^{12}$, $-NX^6S(O)_2X^{12}$, $-NX^6$ $CONX^{11}X^{12}$, $-NX^6S(O)_2$ $NX^{11}X^{12}$, $-NX^6C(O)X^{12}$, imidazolyl, thiazolyl and tetrazolyl, provided that if $A^1$ is optionally substituted with methylenedioxy then it can only be substituted with one methylenedioxy;

where $X^{11}$, for each occurrence, is independently hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, $-S(O)_m(C_1-C_6)$alkyl, 1 to 5 halogens, 1 to 3 hydroxy groups, 1 to 3 $(C_1-C_{10})$alkanoyloxy groups or 1 to 3 $(C_1-C_6)$alkoxy groups;

$X^{12}$, for each occurrence, is independently hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form $-(CH_2)_r-L^1-(CH_2)_r-$;

$L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$ cycloalkyl in the definition of $X^2$ are optionally independently substituted with $-S(O)_m(C_1-C_6)$alkyl, $-C(O)OX^3$, 1 to 5 halogens or 1–3 $OX^3$ groups;

$X^3$ for each occurrence is independently hydrogen or $(C_1-C_6)$alkyl;

$X^6$ for each occurrence is independently hydrogen, optionally substituted $(C_1-C_6)$alkyl, $(C_2-C_6)$halogenated alkyl, optionally substituted $(C_3-C_7)$cycloalkyl, $(C_3-C_7)$ halogenated cycloalkyl, where optionally substituted $(C_1-C_6)$alkyl and optionally substituted $(C_3-C_7)$ cycloalkyl in the definition of $X^6$ is optionally independently mono- or di-substituted with $(C_1-C_4)$alkyl, hydroxy, $(C_1-C_4)$alkoxy, carboxyl, $CONH_2$, $-S(O)_m$ ($C_1$–$C_6$)alkyl, carboxylate ($C_1$–$C_4$)alkyl ester or 1H-tetrazol-5-yl; or when there are two $X^6$ groups on one atom and both $X^6$ are independently ($C_1$–$C_6$)alkyl, the two ($C_1$–$C_6$)alkyl groups may be optionally joined and, together with the atom to which the two $X^6$ groups are attached, form a 4- to 9-membered ring optionally having oxygen, sulfur or $NX^7$ as a ring member;

$x^7$ is hydrogen or ($C_1$–$C_6$)alkyl optionally substituted with hydroxy;

m for each occurrence is independently 0, 1 or 2;

with the proviso that:

$X^6$ and $X^{12}$ cannot be hydrogen when attached to C(O) or $S(O)_2$ in the form $C(O)X^6$, $C(O)X^{12}$, $S(O)_2X^6$ or $S(O)_2X^{12}$.

A preferred group of compounds, designated the A Group, comprises those compounds having the Formula I shown above or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $X^4$ is hydrogen;

$R^4$ is hydrogen or methyl;

$R^7$ is hydrogen or ($C_1$–$C_3$)alkyl; and $R^8$ is hydrogen or ($C_1$–$C_3$)alkyl optionally substituted with up to two hydroxyl groups.

A preferred group of compounds within the A Group, designated the B Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein Het is

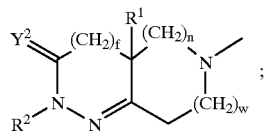

$R^1$ is $A^1$—$(CH_2)_t$, —$(CH_2)_q$—($C_3$–$C_7$)cycloalkyl or ($C_1$–$C_{10}$)alkyl;

where $A^1$ in the definition of $R^1$ is optionally substituted with up to three substituents, each substituent being independently selected from the group consisting of fluoro, chloro, methyl, methoxy, trifluoromethoxy, difluoromethoxy and trifluoromethyl;

the cycloalkyl and alkyl groups in the definition of $R^1$ are optionally substituted with ($C_1$–$C_4$)alkyl, hydroxyl, ($C_1$–$C_4$)alkoxy, carboxyl, $CONH_2$, —$S(O)_m$($C_1$–$C_6$) alkyl, —$CO_2$($C_1$–$C_4$)alkyl ester, 1H-tetrazol-5-yl or up to 3 fluoro;

$Y^2$ is O; and $R^2$ is hydrogen, —($C_0$–$C_3$)alkyl-($C_3$–$C_8$)cycloalkyl, phenyl or ($C_1$–$C_8$)alkyl where the ($C_1$–$C_8$)alkyl group is optionally substituted with hydroxy, trifluoromethyl or up to 3 halogen.

A preferred group of compounds within the B Group, designated the C Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein n and w are each 1; f is 0; $R^2$ is H, methyl, ethyl or trifluoroethyl and $R^1$ is phenyl-$CH_2$—, pyridyl-$CH_2$— or thiazolyl-$CH_2$.

A preferred group of compounds within the C Group, designated the D Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^7$ and $R^8$ are each hydrogen; and $R^3$ is phenyl-$CH_2$—O—$CH_2$—, phenyl-$CH_2$—$CH_2$—$CH_2$— or naphthyl-$CH_2$; said phenyl being optionally substituted with up to three fluoro, chloro.

A preferred compound within the D Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^1$ is phenyl-$CH_2$—, $R^2$ is methyl; $R^3$ is phenyl-$CH_2$—O—$CH_2$—; $R^a$ and $R^b$ are each hydrogen; a is 0; b is 1; and E is vinylene.

Another preferred compound within the D Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^1$ is phenyl-$CH_2$—, $R^2$ is methyl; $R^3$ is phenyl-$CH_2$—O—$CH_2$—; $R^a$ is methyl; $R^b$ is hydrogen; a is 0; b is 1; and E is vinylene.

Another preferred compound within the D Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^1$ is phenyl-$CH_2$—, $R^2$ is methyl; $R^3$ is phenyl-$CH_2$—O—$CH_2$—; $R^a$ and $R^b$ are each methyl; a is 0; b is 1; and E is vinylene.

Another preferred compound within the D Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^1$ is phenyl-$CH_2$; $R^2$ is methyl; $R^3$ is phenyl-$CH_2$—O—$CH_2$—; $R^a$ and $R^b$ are each hydrogen; a is 0; b is 1; and E is metaphenylene.

Another preferred compound within the D Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ is methyl; $R^b$ is hydrogen; a is 0; b is 1; and E is metaphenylene.

Another preferred compound within the D Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ and $R^b$ are each methyl; a is 0; b is 1; and E is metaphenylene.

A preferred group of compounds within the D Group are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, selected from 4-amino-but-2-enoic acid (2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-amide; 4-amino-pent-2-enoic acid (2-(3a-benzyl-2-methyl-3-oxo-2,3,3a,4,6,7-hexaydro-pyrazolo[4,3-c]pyridin-5-yl)-1-benzyloxymethyl-2-oxo-ethyl)-amide; 4-amino-4-methyl-pent-2-enoic acid (2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-amide; 3-aminomethyl-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide; 3-(1-amino-ethyl)-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide; and 3-(1-amino-1-methyl-ethyl)-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide.

Another preferred group of compounds within the B Group, designated the E Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein n and w are each 1; f is 0; $R^2$ is hydrogen; $R^3$ is Ph—$CH_2$—O—$CH_2$—; $R^7$ and $R^8$ are each hydrogen; and $R^1$ is phenyl-$CH_2$—.

A particularly preferred compound within the E Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each methyl; a is 0; b is 1; and E is metaphenylene.

Another particularly preferred compound within the E Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, which is 3-(1-amino-1-methyl-ethyl)-N-(2-(3a-benzyl-03-oxo-2,3,3a,4,6,7-hexahydro-pyrazolo[4,3-c]pyridin-5-yl)-1-benzyloxymethyl-2-oxo-ethyl)-benzamide.

Another preferred group of compounds within the C Group, designated the F Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^7$ and $R^8$ are each hydrogen; and $R^3$ is 3-indolyl-methyl.

A preferred compound within the F Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each methyl; a is 0; b is 1; and E is metaphenylene.

Another preferred compound within the F Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, which is 3-(1-amino-1-methyl-ethyl)-N-(2-(3a-benzyl-2-methyl-3-oxo-2,3,3a,4,6,7-hexahydro-pyrazolo[4,3-c]pyridin-5-yl)-1-(1H-indol-3-ylmethyl)-2-oxo-ethyl)-benzamide.

Another preferred group within the B Group, designated the G Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein n and w are each 1; f is 0; $R^2$ is 2,2,2-trifluoroethyl; and $R^1$ is 2-pyridylmethyl.

A preferred group of compounds within the G Group, designated the H Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, $R^7$ and $R^8$ are each hydrogen; and $R^3$ is 2,4-difluorobenzyloxymethyl.

A particularly preferred compound within the H Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each hydrogen; a is 0; b is 1; and E is metaphenylene.

Another particularly preferred compound within the H Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, which is 3-(1-amino-1-methyl-ethyl)-N-(2-(3a-pyridin-2-ylmethyl-2-(2,2,2-trifluoro-ethyl)-3-oxo-2,3,3a,4,6,7-hexahydro-pyrazolo[4,3-c]pyridin-5-yl)-1-(2,4-difluorobenzyloxymethyl)-2-oxo-ethyl)-benzamide.

Another particularly preferred group of compounds within the A Group, designated the I Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein
Het is

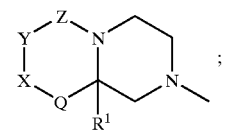

$R^1$ is —$(CH_2)_r$—$A^1$, —$(CH_2)_q$—$(C_3$-$C_7)$cycloalkyl or $(C_1$-$C_{10})$alkyl;
where $A^1$ in the definition of $R^1$ is optionally substituted with up to three substituents, each substituent being independently selected from the group consisting of fluoro, chloro, methyl, methoxy, trifluoromethoxy, difluoromethoxy and trifluoromethyl; and the cycloalkyl and alkyl groups in the definition of $R^1$ are optionally substituted with ($C_1$–$C_4$)alkyl, hydroxyl, ($C_1$–$C_4$)alkoxy, carboxyl, $CONH_2$, —S(O)$_m$($C_1$–$C_6$) alkyl, —$CO_2$($C_1$–$C_4$)alkyl ester, 1H-tetrazol-5-yl or up to 3 fluoro.

A preferred group of compounds within the I Group, designated the J Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein Z is C=O; Q is a covalent bond; X is C=O; $R^2$ is H, methyl, ethyl or trifluoroethyl; $R^1$ is phenyl-$CH_2$—, pyridyl-$CH_2$— or thiazolyl-$CH_2$; and Y is $NR^2$.

A preferred group of compounds within the J Group, designated the K Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein Z is C=O; $R^1$ is $A^1$—$CH_2$—, where $A^1$ in the definition of $R^1$ is phenyl or pyridyl where said phenyl or pyridyl is optionally substituted with up to three substituents, each substituent being independently selected from the group consisting of fluoro, chloro, methyl, methoxy, difluoromethoxy, trifluoromethoxy and trifluoromethyl; and $R^3$ is phenyl-$CH_2$—O—$CH_2$—, pyridyl-$CH_2$—O—$CH_2$—, phenyl-($CH_2$)$_3$—, 3-indolyl-$CH_2$—, alpha-naphthyl($C_1$–$C_4$)alkyl or thiazolyl-$CH_2$—O—$CH_2$—, where the aryl portion of the groups defined for $R^3$ is optionally substituted with up to three substituents, each substituent being independently selected from the group consisting of fluoro, chloro, methyl, methoxy, difluoromethoxy, trifluoromethoxy and trifluoromethyl.

A preferred group of compounds within the K Group, designated the L Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^2$ is hydrogen or ($C_1$–$C_3$)alkyl where the alkyl group is optionally substituted with up to three fluoro groups.

A preferred group of compounds within the L Group, designated the M Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^3$ is phenyl-$CH_2$—O—$CH_2$ or phenyl-($CH_2$)$_3$—, where the phenyl in the definition of $R^3$ is optionally substituted with up to three substituents, each substituent being independently selected from the group consisting of fluoro, chloro, methyl, methoxy, difluoromethoxy, trifluoromethoxy and trifluoromethyl.

A preferred group of compounds within the M Group, designated the N Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^1$ is $CH_2$—$A^1$ where $A^1$ in the definition of $R^1$ is phenyl, 2-pyridyl or 3-pyridyl optionally substituted with up to three fluoro or chloro groups; $R^2$ is methyl or ethyl, said ethyl being optionally substituted with up to three fluoro groups; and $R^3$ is phenyl-$CH_2$—O—$CH_2$—, where the phenyl group is optionally substituted with up to three fluoro or chloro groups or up to two trifluoromethyl groups.

A preferred group of compounds within the N Group, designated the O Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^1$ is 2-pyridylmethyl; $R^2$ is 2,2,2-trifluroethyl; $R^3$ is 2,4-difluorophenylmethyloxymethyl; and $R^4$, $X^4$, $R^7$ and $R^8$ are each hydrogen.

A preferred compound within the O Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each hydrogen; a is 0; b is 1; and E is metaphenylene.

Another preferred compound within the O Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ is methyl; $R^b$ is hydrogen; a is 0; b is 1; and E is metaphenylene.

Another preferred compound within the O Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each methyl; a is 0; b is 1; and E is metaphenylene.

Another preferred compound within the O Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ and $R^b$ are each hydrogen; a is 0; b is 1; and E is vinylene.

Another preferred compound within the O Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ is methyl; $R^b$ is hydrogen; a is 0; b is 1; and E is vinylene.

Another preferred compound within the O Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ and $R^b$ are each methyl; a is 0; b is 1; and E is vinylene.

A preferred group of compounds within the O Group are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, selected from 3-aminomethyl-N-(1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 3-(1-amino-ethyl)-N-(1-(2,4-difluoro-benzyloxymethyl)-2-(1,3-dioxo-8a-pyridin-2-ylmethyl-2(2,2,2-trifluoro-ethyl)-hexahydro-imidazo[1,5-a]pyrazin-7-yl)-20-oxo-ethyl)-benzamide; 3-(1-amino-1-methyl)-N-(1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 4-amino-but-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; 4-amino-pent-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; and 4-amino-4-methyl-pent-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

Another preferred group of compounds within the N Group, designated the P Group, are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, wherein $R^1$ is 2-pyridylmethyl; $R^2$ is 2,2,2-trifluroethyl; $R^3$ is phenylmethyloxymethyl; and $R^4$, $X^4$, $R^7$ and $R^8$ are each hydrogen.

A preferred compound within the P Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each hydrogen; a is 0; b is 1; and E is metaphenylene.

Another preferred compound within the P Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ is methyl; $R^b$ is hydrogen; a is 0; b is 1; and E is metaphenylene.

Another preferred compound within the P Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^a$ and $R^b$ are each methyl; a is 0; b is 1; and E is metaphenylene.

Another preferred compound within the P Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ and $R^b$ are each hydrogen; a is 0; b is 1; and E is vinylene.

Another preferred compound within the P Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ is methyl; $R^b$ is hydrogen; a is 0; b is 1; and E is vinylene.

Another preferred compound within the P Group is the compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^2$ is methyl; $R^3$ is phenyl-$CH_2$—O—$CH_2$—; $R^a$ and $R^b$ are each methyl; a is 0; b is 1; and E is vinylene.

A preferred group of compounds within the P Group are those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs, selected from 3-aminomethyl-N-(2-(1,3-dioxo-8a-pyridin-2-ylmethyl-2-(2,2,2-trifluoro-ethyl)-hexahydro-imidazo[1,5-a]pyrazin-7-yl)-1-benzyloxymethyl-2-oxo-ethyl)-benzamide; 3-(1-amino-ethyl)-N-(benzyloxymethyl-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 3-(1-amino-1-methyl-ethyl)-N-(benzyloxymethyl-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 4-amino-but-2-enoic acid (1-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; 4-amino-pent-2-enoic acid (1-(benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; and 4-amino-4-methyl-pent-2-enoic acid (1-(benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

This invention is also directed to a pharmaceutical composition comprising a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug and a pharmaceutically acceptable carrier or diluent.

This invention is also directed to methods for treating or preventing musculoskeletal frailty in a mammal comprising administering to said mammal a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within the above method is a method wherein osteoporosis is treated.

This invention is also directed to methods for increasing IGF-1 levels in mammal deficient in IGF-1 comprising administering to said mammal a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method, designated Method A, for treating or preventing a growth hormone mediated disease or condition in a mammal comprising administering to said mammal a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method A, designated Method B, is a method wherein the disease or condition is diabetes, congestive heart failure, obesity, frailty associated with aging or frailty associated with obesity.

A preferred method within Method B is a method wherein the disease or condition is congestive heart failure.

Another preferred method within Method B is a method wherein the disease or condition is frailty associated with aging.

This invention is also directed to a method, designated Method C, for accelerating bone fracture repair in a mammal, attenuating protein catabolic response after a major operation in a mammal, reducing cachexia and protein loss due to chronic illness in a mammal, accelerating wound healing in a mammal, or accelerating the recovery of burn patients or patients having undergone major surgery comprising administering to said mammal a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method C is a method for accelerating the recovery of patients having undergone major surgery.

Another preferred method within Method C is a method for accelerating bone fracture repair.

This invention is also directed to a method for improving muscle strength, mobility, maintenance of skin thickness, metabolic homeostasis or renal homeostasis in a mammal comprising administering to said mammal a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method, designated Method D, for the treatment or prevention of musculoskeletal frailty in a mammal comprising administering to said mammal a therapeutically effective amount of a bisphosphonate and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method D is wherein osteoporosis is treated in a mammal.

Another preferred method within Method D is wherein said bisphosphonate is alendronate.

Another preferred method within Method D is wherein said bisphosphonate is ibandronate.

This invention is also directed to a method, designated Method E, for the treatment or prevention of musculoskeletal frailty in a mammal comprising administering to said mammal a therapeutically effective amount of estrogen or Premarin® and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method E is wherein osteoporosis is treated in a mammal.

This invention is also directed to a method, designated Method F, for the treatment of musculoskeletal frailty in a mammal comprising administering to said mammal a therapeutically effective amount of calcitonin and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method F is wherein osteoporosis is treated in a mammal.

This invention is also directed to a method, designated Method G, for the treatment of musculoskeletal frailty in a mammal comprising administering to said mammal a therapeutically effective amount of a selective estrogen receptor modulator (SERM) and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method G is wherein said SERM is tamoxifen, droloxifene, raloxifene or idoxifene.

Another preferred method within Method G is wherein said SERM is cis-6-(4-fluoro-phenyl)-5-[4-(2-piperidin-1-yl-ethoxy)-phenyl]-5,6,7,8-tetrahydro-naphthalene-2-ol; (−)-cis-6-phenyl-5-[4-(2-pyrrolidin-1-yl-ethoxy)-phenyl]-5,6,7,8-tetrahydro-naphthalene-2-ol; cis-6-phenyl-5-[4-(2-pyrrolidin-1-yl-ethoxy)-phenyl]-5,6,7,8-tetrahydro-naphthalene-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydro-isoquinoline.

This invention is also directed to a method for enhancing growth and improving carcass quality of an animal other than a human comprising administering to said animal an effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method for enhancing feed efficiency in an animal other than a human comprising administering to said animal an effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method for increasing milk production in a female mammal comprising administering to said female mammal an effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method for increasing piglet number, increasing pregnancy rate in a sow, increasing viability of a piglet, increasing weight of a piglet or increasing muscle fiber size in a piglet comprising administering to said sow or piglet an effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method for increasing muscle mass in a mammal comprising administering to said mammal a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method for promoting growth in a growth hormone deficient child comprising administering to said growth hormone deficient child a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method, designated Method H, for the treatment or prevention of diabetes, congestive heart failure, obesity, frailty associated with aging or frailty associated with obesity in a mammal comprising administering to said mammal a therapeutically effective amount of a functional somatostatin antagonist and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method H is wherein said functional somatostatin antagonist is an alpha-2 adrenergic agonist and the mammal is a dog, cat or horse.

Another preferred method within Method H is wherein said alpha-2 adrenergic agonist is clonidine, xylazine or medetomidine.

This invention is also directed to a method, designated Method I, for treating insulin resistance in a mammal comprising administering to said mammal an effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

A preferred method within Method I is wherein said mammal is suffering from type I diabetes, type II diabetes, hyperglycemia, impaired glucose tolerance or an insulin resistant syndrome.

Another preferred method within Method I is wherein said mammal is suffering from insulin resistance is associated with obesity or old age.

This invention is also directed to a method for increasing the endogenous production or release of growth hormone in a mammal comprising administering a therapeutically effective amount of a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug and a growth hormone secretagogue selected from the group consisting of GHRP-6, Hexarelin, GHRP-1, growth hormone releasing factor (GRF), IGF-1, IGF-2 and B-HT920 or an analog thereof.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug; a bisphosphonate and a pharmaceutically acceptable carrier or diluent.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug; estrogen or Premarin® and a pharmaceutically acceptable carrier or diluent.

This invention is particularly directed to a pharmaceutical composition as set forth in the immediately preceding paragraph further comprising progesterone.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, calcitonin and a pharmaceutically acceptable carrier or diluent.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, an alpha-2 adrenergic agonist and a pharmaceutically acceptable carrier or diluent.

This invention is particularly directed to a pharmaceutical composition as set forth in the immediately preceding paragraph wherein said alpha-2 adrenergic agonist is clonidine, xylazine or medetomidine.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, a growth hormone secretagogue selected from the group consisting of GHRP-6, Hexarelin, GHRP-1, growth hormone releasing factor (GRF), IGF-1, IGF-2 and B-HT920 or an analog thereof, and a pharmaceutically acceptable carrier or diluent.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, a $\beta_3$ adrenergic receptor agonist and a pharmaceutically acceptable carrier or diluent.

This invention is particularly directed to a pharmaceutical composition as set forth in the immediately preceding paragraph wherein said $\beta_3$ adrenergic receptor agonist is (4-(2-(2-(6-aminopyridin-3-yl)-2(R)-hydroxyethylamino)ethoxy)phenyl)acetic acid.

This invention is also directed to a method for increasing levels of endogenous growth hormone in a mammal comprising administering to said mammal a therapeutically effective amount of a functional somatostatin antagonist and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a method for treating obesity and/or improving lean meat to fat ratio in a mammal comprising administering to said mammal a therapeutically effective amount of a $\beta_3$ adrenergic receptor agonist and a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, a selective estrogen receptor modulator (SERM) and a pharmaceutically acceptable carrier or diluent.

This invention is also directed to a pharmaceutical composition comprising a compound of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, a functional somatostatin antagonist and a pharmaceutically acceptable carrier or diluent.

This invention is also directed to a kit comprising:
a. a compound of claim 1 and a pharmaceutically acceptable carrier or diluent in a first unit dosage form;
b. a growth hormone secretagogue selected from the group consisting of GHRP-6, Hexarelin, GHRP-1, growth hormone releasing factor (GRF), IGF-1, IGF-2 and B-HT920 or an analog thereof and a pharmaceutically acceptable carrier or diluent in a second unit dosage form; and
c. a container.

This invention is also directed to a kit comprising:
a. a compound of claim 1 and a pharmaceutically acceptable carrier or diluent in a first unit dosage form;
b. a selective estrogen receptor modulator (SERM) and a pharmaceutically acceptable carrier or diluent in a second unit dosage form; and
c. a container.

This invention is also directed to a kit comprising:
a. a compound of claim 1 and a pharmaceutically acceptable carrier or diluent in a first unit dosage form;
b. calcitonin and a pharmaceutically acceptable carrier or diluent in a second unit dosage form; and
c. a container.

This invention is also directed to a kit comprising:
a. a compound of claim 1 and a pharmaceutically acceptable carrier or diluent in a first unit dosage form;
b. a functional somatostatin antagonist and a pharmaceutically acceptable carrier or diluent in a second unit dosage form; and
c. a container.

This invention is also directed to a kit comprising:
a. a compound of claim 1 and a pharmaceutically acceptable carrier or diluent in a first unit dosage form;
b. a bisphosphonate and a pharmaceutically acceptable carrier or diluent in a second unit dosage form; and
c. a container.

This invention is also directed to a kit comprising:
a. a compound of claim 1 and a pharmaceutically acceptable carrier or diluent in a first unit dosage form;
b. estrogen or Premarin® and a pharmaceutically acceptable carrier or diluent in a second unit dosage form; and
c. a container.

This invention is also directed to a kit comprising:
a. a compound of claim 1 and a pharmaceutically acceptable carrier or diluent in a first unit dosage form;
b. a $\beta_3$ adrenergic receptor agonist and a pharmaceutically acceptable carrier or diluent in a second unit dosage form; and
c. a container.

DETAILED DESCRIPTION OF THE INVENTION

In general the compounds of Formula I can be made by processes well known in the chemical arts. In particular, the preparation of the compounds of Formula I of the present invention can be carried out in sequential or convergent synthetic routes. Syntheses detailing the preparation of the compounds of Formula I in a sequential manner are presented in the following reaction schemes.

Many of the schemes illustrated below describe compounds which contain protecting groups Prt, Prt' or Prt", which can be any suitable protecting group known to those skilled in the art. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi can be employed; pressures from 10 to 70 psi are preferred. Alternatively, the benzyloxycarbonyl group can be removed by transfer hydrogenation.

Removal of BOC protecting groups can be accomplished using a strong acid such as trifluoroacetic acid or hydrochloric acid with or without the presence of a cosolvent such as dichloromethane or methanol at a temperature of about −30° to 70° C., preferably about −5° to about 35° C.

Benzyl groups on amines can be removed by a number of methods including catalytic hydrogenation with hydrogen in the presence of a palladium catalyst in a protic solvent such as methanol. Hydrogen pressures from 1–1000 psi can be employed; pressures from 10 to 70 psi are preferred. The addition and removal of these and other protecting groups are discussed in detail by T. Greene in Protective Groups in Organic Synthesis, John Wiley & Sons, New York, 1981.

The variables shown in the following schemes are as described for compounds of Formula I, above, unless otherwise indicated.

SCHEME 1

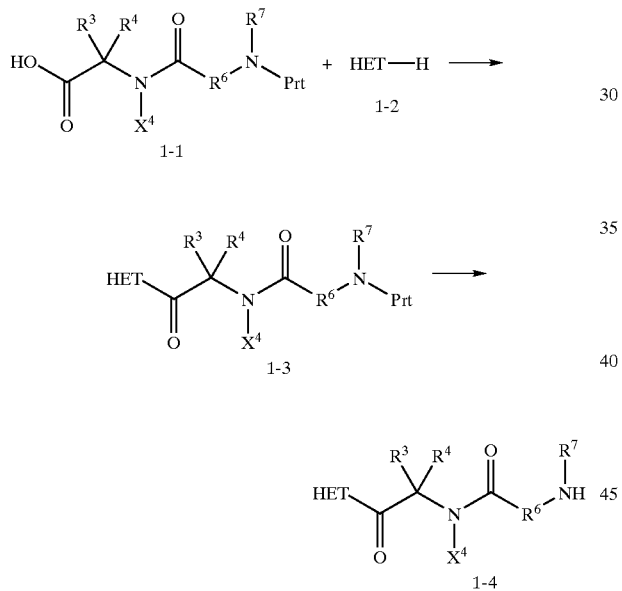

As illustrated in Scheme 1, coupling of a heterocyclic amine (HET at the NH) of formula 1-2, as defined for Formula I, with a protected amino acid of formula 1-1, where Prt is a suitable protecting group, is conveniently carried out in an inert solvent such as dichloromethane or DMF by a coupling reagent such as EDC, DCC or DEC in the presence of HOBT or HOAT. In the case where amine 1-2 is present as the hydrochloride salt, it is preferable to add one equivalent of a suitable base such as triethylamine to the reaction mixture. Alternatively, the coupling can be effected with a coupling reagent such as BOP in an inert solvent such as methanol or with PPAA in a solvent like ethyl acetate. Such coupling reactions are generally conducted at temperatures of about −30° to about 80° C., preferably 0° to about 25° C. For a discussion of other conditions used for coupling peptides see Houben-Weyl, Vol. XV, part II, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization, or by trituration. Transformation of 1-3 into an intermediate of formula 1-4 can be carried out by removal of the protecting group Prt as described above.

SCHEME 2

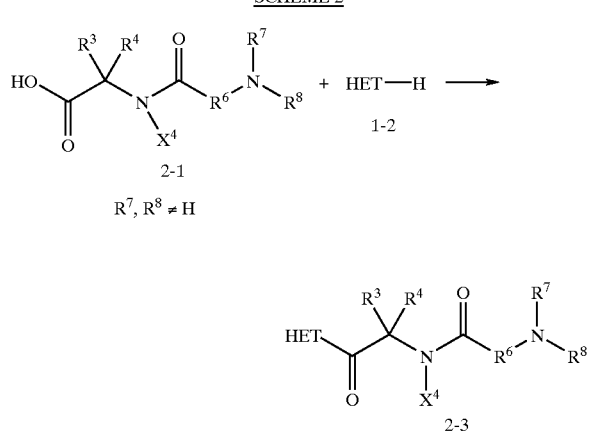

As illustrated in Scheme 2, coupling of a heterocyclic amine of formula 1-2, as defined in claim 1, with an amino acid of formula 2-1, where $R^7$ and $R^8$ are not hydrogen, is conveniently carried out in a manner similar to that described in Scheme 1.

SCHEME 3

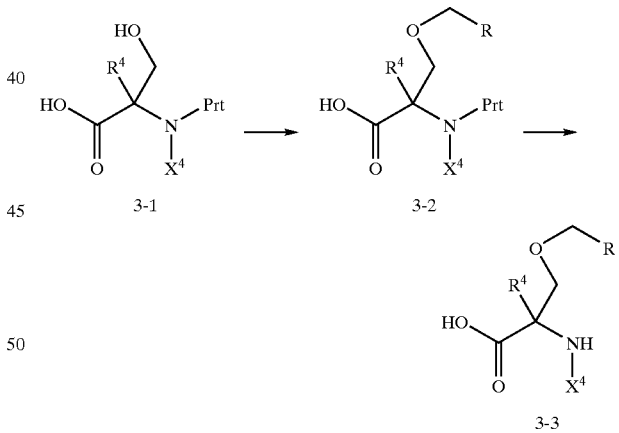

As illustrated in Scheme 3, an intermediate ether of formula 3-2 can be prepared by treating an amino acid of formula 3-1, where Prt is a suitable protecting group, with a base such as potassium carbonate or sodium hydride followed by an alkyl halide, benzyl halide, tosylate or mesylate such as benzylbromide in a suitable solvent such as DMF or THF. Deprotection of the amine transforms 3-2 into 3-3. Alternatively, many amino acids of formula 3-3 are commercially available. R is a group defined for $R^3$ in Formula I, above.

SCHEME 4

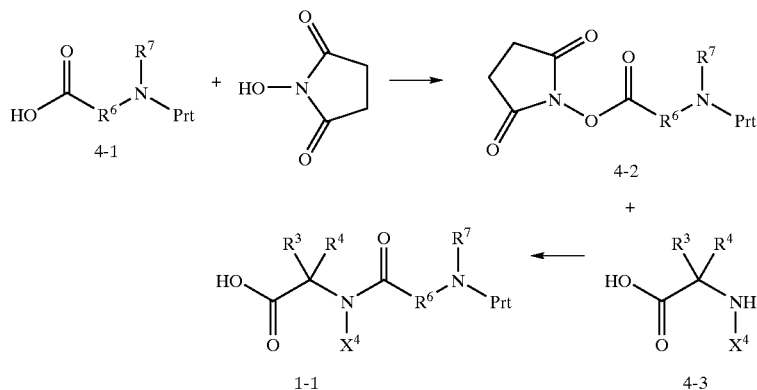

As illustrated in Scheme 4, intermediates of formula 4-2 can be prepared by treating an acid of formula 4-1 with hydroxysuccinimide in the presence of a coupling agent such as EDC in an inert solvent such as methylene chloride. Treating 4-2 with an amino acid of formula 4-3 in a solvent such as DMF in the presence of a base such as diisopropylethylamine produces compounds of formula 1-1.

SCHEME 5

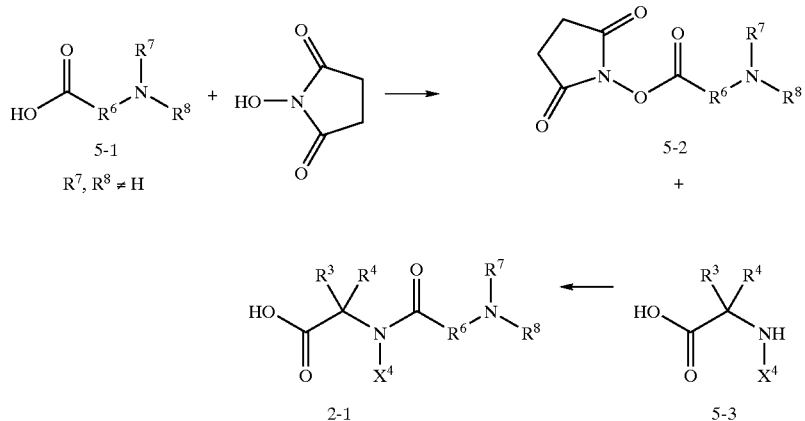

As illustrated in Scheme 5, dipeptides of formula 2-1, where $R^7$ and $R^8$ are not hydrogen, is conveniently synthesized by the procedures described in Scheme 4.

In Schemes 5a–5c, syntheses of amino acids of formulas 5a-3, 5b-3 and 5c-3 are described. Various methods of preparing protected amino acids of formula 5a-3 are well known in the art.

SCHEME 5A

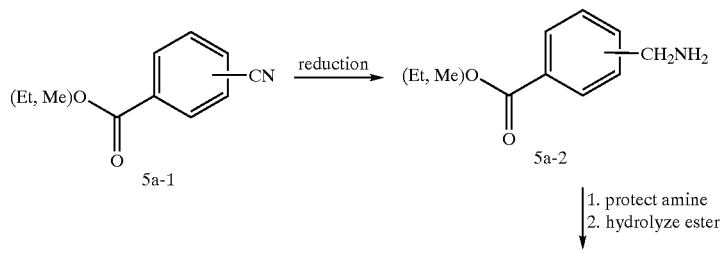

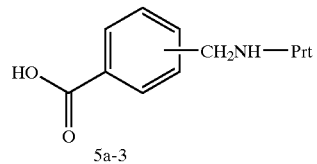

As illustrated in Scheme 5a, benzoic acid esters of formula 5a-1 are reduced, e.g., with Raney nickel in ethanol in the presence of ammonia to provide the corresponding benzylamine derivative 5a-2. The amino group is protected according to methods well known to those skilled in the art, e.g., as a BOC or CBZ derivative and the ester group is hydrolyzed to afford the protected amino acids of formula 5a-3.

Olefinic amino acids of formula 5c-3 may be prepared as illustrated in Scheme 5c. The protected (Prt) aminoisobutyric methyl or ethyl ester of formula 5c-1 is reduced, e.g., with diisobutylaluminum hydride in a protic solvent such as THF or dichloromethane, to the corresponding aldehyde derivative of formula 5c-2. Alternatively, the commercially available acid of 5c-3 (when Prt is BOC) may be reduced, e.g., with diborane to afford the corresponding alcohol and

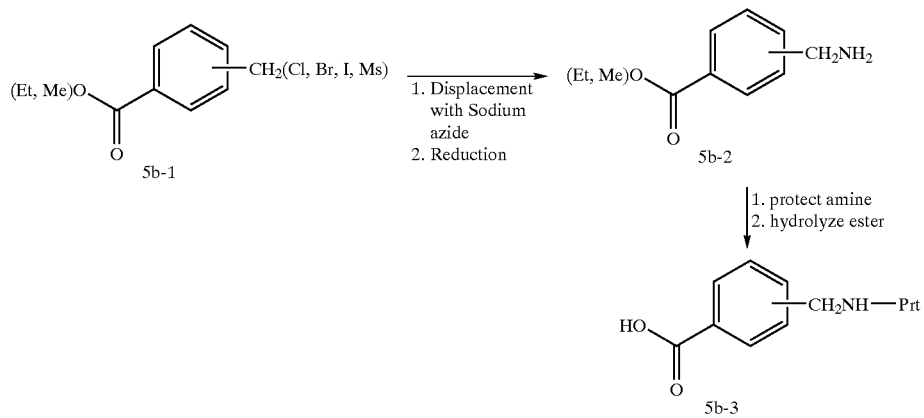

As illustrated in Scheme 35, compounds of the formula 5b-3 can be prepared from the corresponding benzyl compounds (e.g., benzyl halides, benzyl mesylates) of formula 5b-1. The leaving group (e.g., halide, mesylate) is displaced with sodium azide, usually in a polar aprotic solvent such as DMF or DMSO to afford the corresponding azide which is reduced, e.g., with triphenylphosphine in THF-water, to afford the amine derivative, which is converted to acids of formula 5b-3.

oxidized back to the aldehyde 5c-2 by using, e.g., a Swern oxidation procedure. A Horner-Emmons condensation of 5c-2 with triethylphosphonoacetate with a base, e.g., potassium t-butoxide in an aprotic solvent, provides the corresponding unsaturated ester, which can be hydrolyzed under standard conditions to afford the protected amino acid of formula 5c-3.

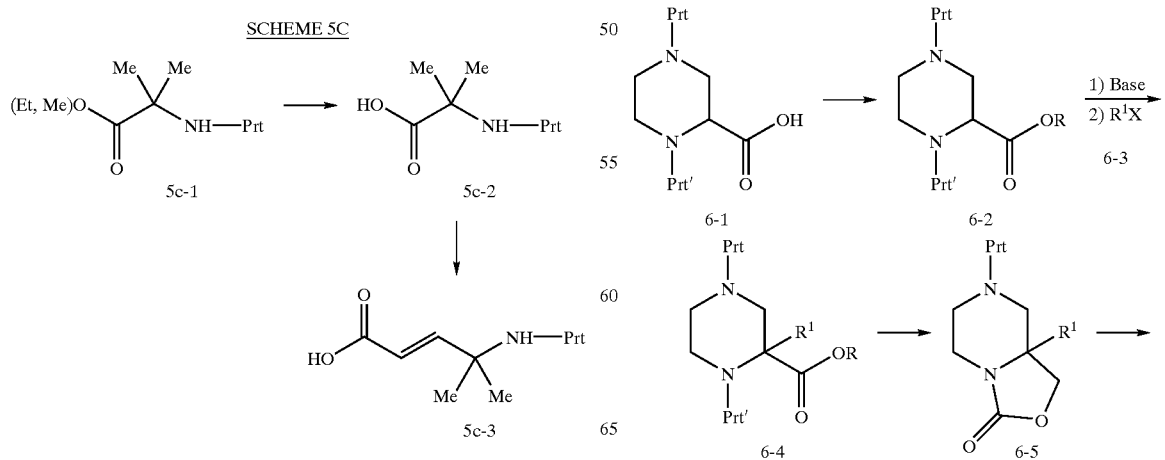

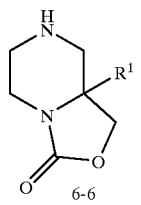

Intermediate esters of formula 6-2, where Prt and Prt' are protecting groups, preferably Prt' is a carbamate protecting group such as CBZ, can be prepared by treating an acid of formula 6-1 with a base such as potassium carbonate followed by an alkyl halide such as iodomethane in a suitable solvent such as DMF. Alternatively, an ester of formula 6-2 can be prepared by reacting an acid of formula 6-1 with diazomethane. For the preparation of compound 6-2 see Bigge, C. F. et al., Tet. Lett., 1989, 30, 5193–5196. Intermediate 6-4 is generated by alkylating ester 6-2 with a reagent such as an alkyl halide, tosylate or mesylate with a base such as NaHMDS in a suitable solvent system such as DMF/THF at a temperature of about −78° C.

Intermediate carbamates of formula 6-5 can be prepared by reacting an intermediate of formula 6-4 with a hydride such as sodium borohydride or superhydride. Transformation of intermediate 6-5 to 6-6 can be achieved by removal of the protecting group Prt as described above.

SCHEME 7

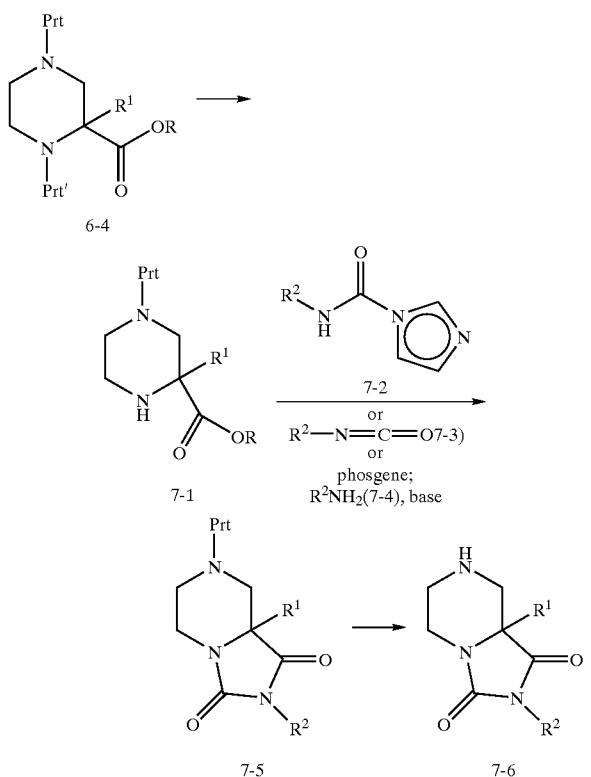

Transformation of intermediate 6-4 to 7-1 can be achieved by removal of the protecting group Prt' as described above. Intermediate ureas of formula 7-5 can be prepared by reacting an intermediate of formula 7-1 with either an acyl imidizolide of formula 7-2, an isocyanate of formula 7-3, or phosgene (or other phosgene equivalent) followed by an amine of formula 7-4 in the presence of a suitable base such as triethylamine. When $R^1$ is —$CH_2$-pyridyl it is preferred to use an isocyanate or acyl imidizolide. Transformation of 7-5 to 7-6 can be achieved by removal of the protecting group Prt as described above.

SCHEME 8

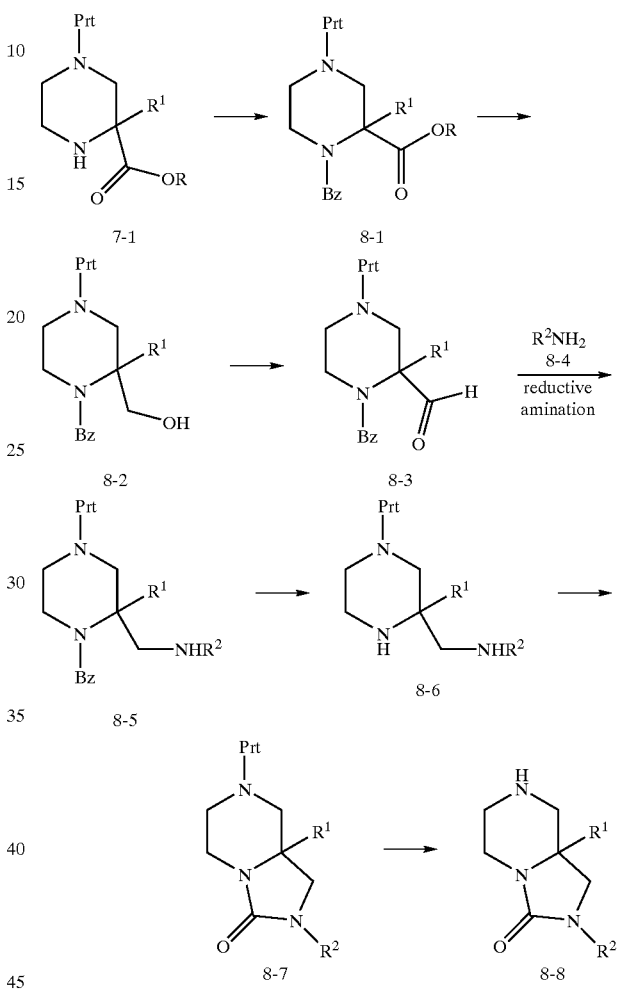

An intermediate benzylamine of formula 8-1 can be prepared by treating an amine of formula 7-1 with a base such as diisopropylethylamine followed by a benzyl halide such as benzyl bromide in a suitable solvent such as acetonitrile. Alternatively, 8-1 can be prepared by treating 7-1 with benzaldehyde and a suitable reducing agent such as $NaCNBH_3$ or $Na(OAc)_3BH$ in a suitable solvent such as methanol or dichloromethane. An alcohol of the formula 8-2 can be prepared by reducing an intermediate of the formula 8-1 with a reducing agent such as superhydride in a suitable solvent such as THF. An alcohol of the formula 8-2 can be oxidized to an aldehyde of the formula 8-3 with an oxidizing agent such as oxalyl chloride/DMSO in a suitable solvent such as dichloromethane at a temperature of about −78° C., with the later addition of a base such as triethylamine to neutralize the reaction mixture (Swern-type oxidation, see Mancuso, A. J., Swern, D., Synthesis, 1981, pp. 165–185).

Compounds of formula 8-5 can be prepared by treating an aldehyde of formula 8-3 with an amine of formula 8-4 in the presence of a suitable reducing agent which include alkali metal borohydrides and cyanoborohydrides. The preferred reducing agent is sodium cyanoborohydride. Sodium borohydride and sodium triacetoxyborohydride may also be used. For a general review of reductive aminations see R. F. Borch, Aldrichimica Acta, 8, 3–10 (1975). Removal of the benzyl group to give 8-6 can be accomplished by a number of reductive methods including hydrogenation in the presence of platinum or palladium catalyst in a protic solvent such as methanol. Cyclization of a diamine of formula 8-6 with CDI or other phosgene equivalents generates a compound of formula 8-7. Removal of the protecting group, as described above, transforms 8-7 into 8-8.

SCHEME 9

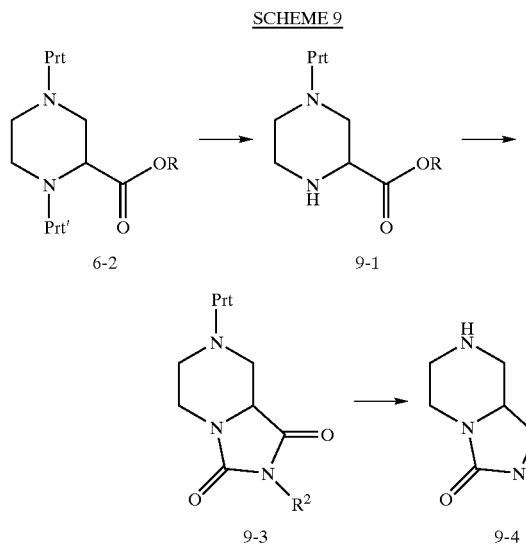

As illustrated in Scheme 9, an intermediate hydantoin of formula 9-4 can be prepared in three steps. An ester of formula 9-1, prepared by cleavage of Prt' from 6-2, can be acylated with an acyl imidizolide of formula 7-2, an isocyanate of formula 7-3, or phosgene (or other phosgene equivalent) followed by an amine of formula 7-4 in the presence of a suitable base such as triethylamine. Transformation of 9-3 to 9-4 can be accomplished by removal of the protecting group Prt as described above.

SCHEME 10

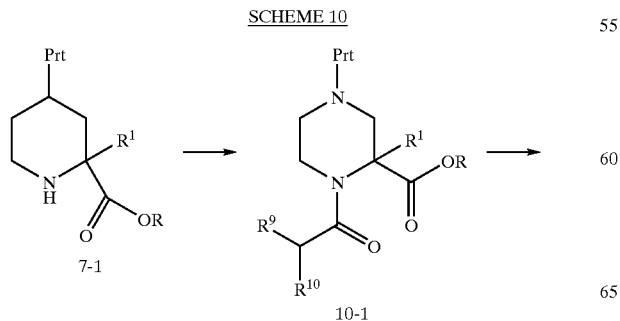

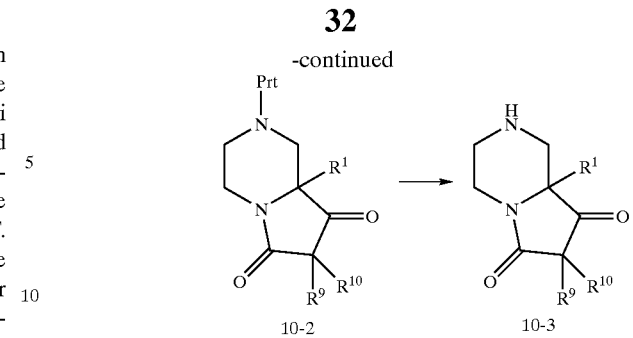

Intermediates of formula 10-1 can be prepared by treating a compound of formula 7-1 with an acyl chloride or other activated carboxylic acid derivative and a suitable base, such as TEA or N,N-diisopropylethylamine. Cyclization of a compound of formula 10-1 occurs upon treating 10-1 with a strong base such as LHMDS at a suitable temperature, about −78° C. to 40° C., to produce an intermediate of formula 10-2. When $R^9$ and/or $R^{10}$ is H, 10-2 may be alkylated with a reagent such as methyl iodide in the presence of a base like NaH to give 10-2 where $R^9$ and $R^{10}$ are not H. Removal of the protecting group, as described above, transforms 10-2 to 10-3.

SCHEME 11

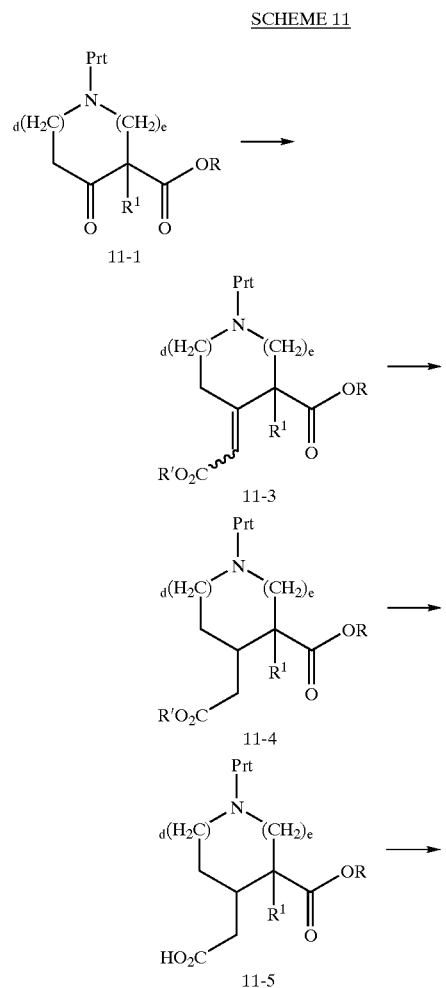

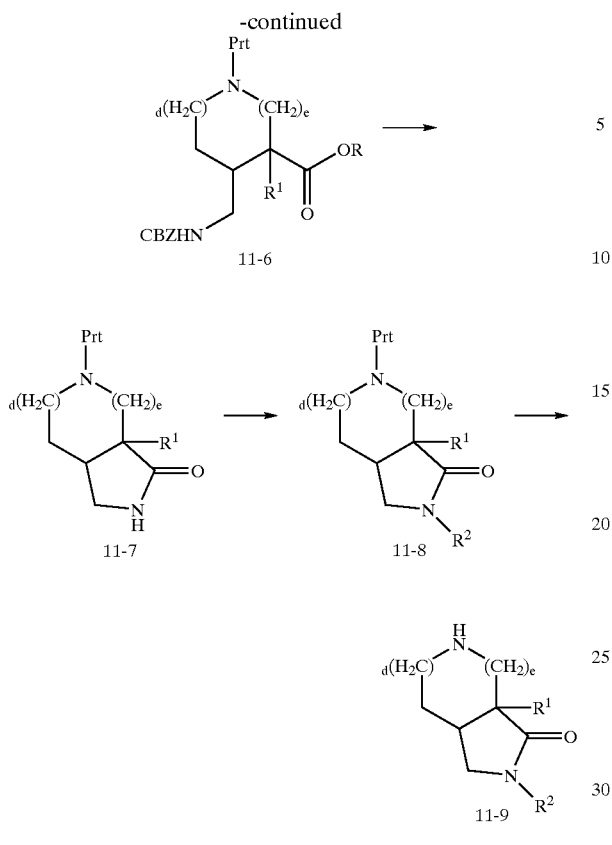

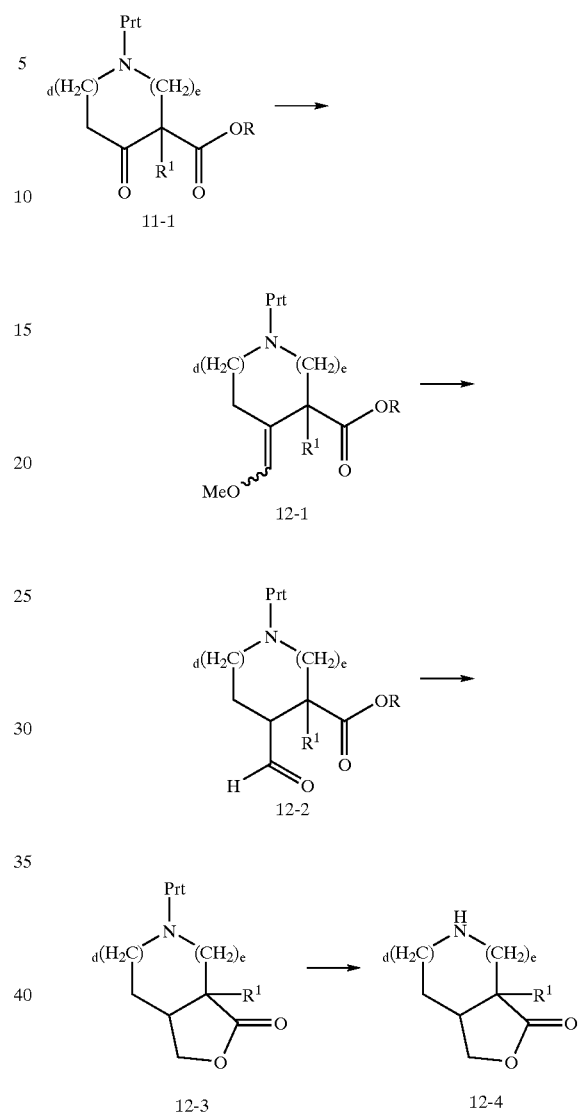

SCHEME 12

Intermediate α,β-unsaturated esters of formula 11-3 (R is an alkyl group) can be prepared by olefinating 11-1 with a reagent such as the anion generated upon treating trimethylphosphonoacetate with a strong base such as potassium tert-butoxide in a suitable solvent such as THF. Catalytic hydrogenation, such as with Pd on carbon in the presence of hydrogen, preferably at 1-4 atmospheres, in a suitable solvent, such as ethyl acetate or methanol, reduces the double bond of 11-3 to produce 11-4. Selective hydrolysis of the less hindered ester group in 11-4 can be performed with a base such as an alkali metal hydroxide in an appropriate solvent, such as a mixture of water, methanol, and/or dioxane. A carboxylic acid of formula 11-5, thus produced can be transformed to 11-6 by converting 11-5 to an acyl azide, such as with DPPA and TEA in benzene, followed by rearrangement to an isocyanate by heating to reflux in a solvent such as benzene, which is then reacted with benzyl alcohol to form 11-6. A lactam of formula 11-7 can be prepared by removal of the CBZ protecting group from the amine in 11-6, followed by cyclization of the amine with the adjacent ester group. Deprotection of this material provides 11-9, $R^2$=H. Alternatively, amide 11-7 can be alkylated by deprotonation with a strong base such as sodium hydride, LHMDS, or KHMDS in a suitable solvent such as DMF or THF followed by treatment with an alkylating agent such as an alkyl halide, mesylate or tosylate. The product, 11-8, may then be deprotected, as described above, to provide 11-9. One skilled in the art will recognize that substitution next to the lactam nitrogen could have been introduced by alkylating ester 11-4 or by olefinating 11-1 to give a tetra-substituted olefin analogous to 11-3.

Intermediate enol ethers of formula 12-1 can be prepared by treating 11-1 (R is an alkyl group) with a reagent, such as methoxymethyl triphenylphosphonium chloride and a strong base, such as potassium tert-butoxide, in a suitable solvent such as THF. Hydrolysis of an enol ether of formula 12-1 under acidic conditions produces aldehyde 12-2. Reduction of the aldehyde group to an alcohol, for example with sodium borohydride in methanol, followed by cyclization converts 12-2 to a lactone of formula 12-3. Deprotection of the nitrogen, as described above, affords 12-4. One skilled in the art will recognize that an $R^{1A}$ substituent could have been introduced by alkylating aldehyde 12-2. In addition, substitution next to the lactone oxygen ($R^9/R^{10}$) could be introduced by olefinating 11-1 to give a tetra-substituted olefin and by treating the latter ketone or aldehyde (12-2) with an alkyl metal such as a Grignard reagent.

SCHEME 13

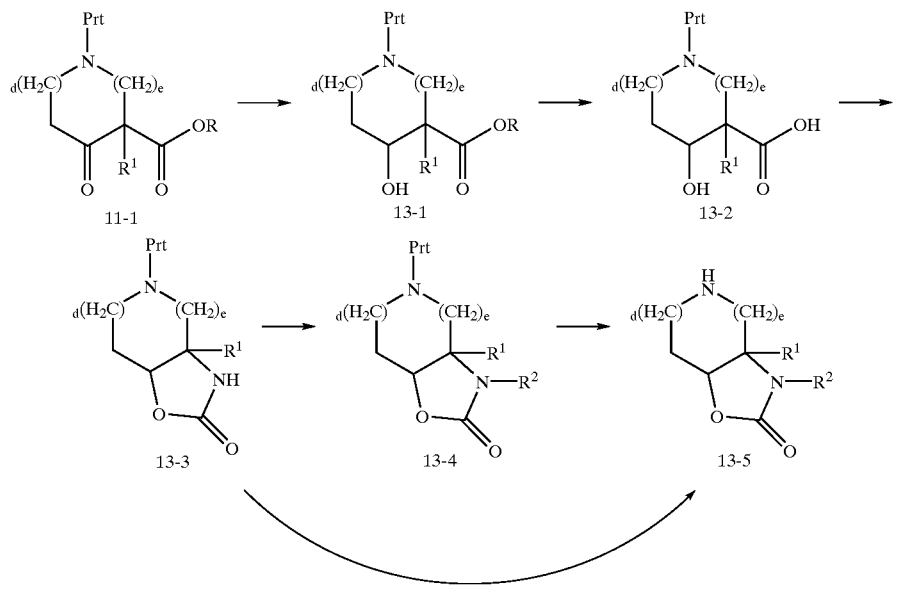

Reduction of the ketone in 11-1 (R is an alkyl group) to an alcohol with a suitable reducing reagent, such as with sodium borohydride in methanol, converts 11-1 to 13-1. Hydrolysis of the ester group in 13-1 according to the method discussed in Scheme 11 produces acid 13-2. Transformation of 13-2 to 13-3 can be achieved by converting 13-2 to acyl azides, for instance with DPPA and TEA in a solvent such as benzene, followed by rearrangement to isocyanates, which then react intramolecularly with the adjacent alcohol to form carbamate 13-3. Deprotection of 13-3 as described above provides 13-5 where $R^2$ is H.

Alternatively, carbamate 13-3 can be alkylated by deprotonation with a strong base such as sodium hydride, LHMDS, or KHMDS in a suitable solvent such as DMF or THF followed by treatment with an alkylating agent such as an alkyl halide ($R^2$-halide), mesylate or tosylate. Removal of the protecting group, as described above, transforms 13-4 to 13-5. One skilled in the art will recognize that an $R^{1A}$ substituent could have been introduced by treating ketone 11-1 with an alkyl metal reagent, such as methyl magnesium bromide, at a suitable temperature for a Grignard reaction.

SCHEME 14

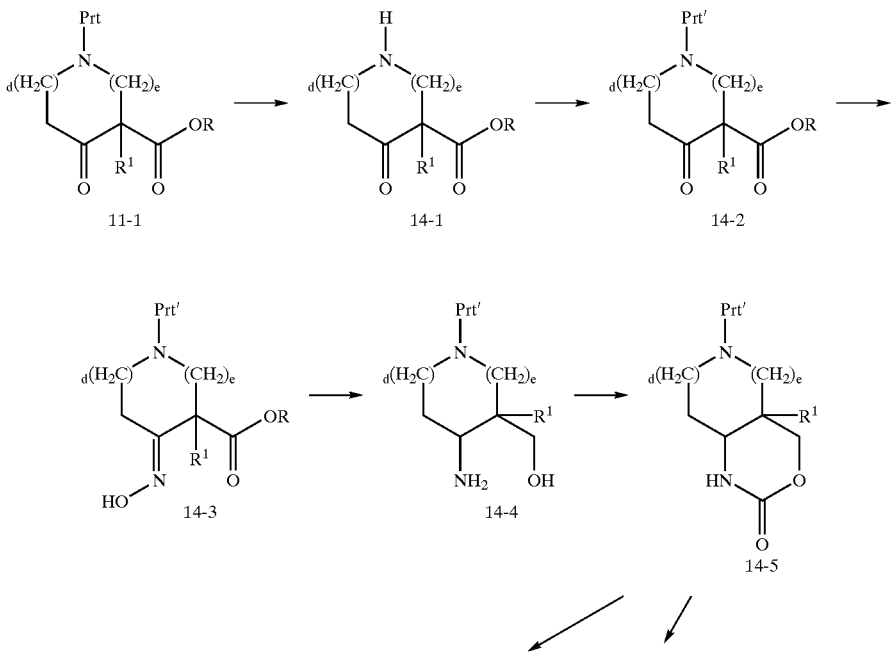

-continued

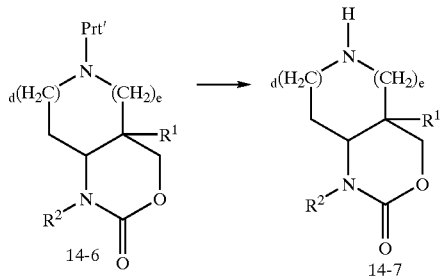

Removal of the carbamate protecting group, Prt, from 11-1 (R is an alkyl group) produces 14-1. Reprotection, such as with a benzyl group gives 14-2. Treating 14-2 with hydroxylamine yields an oxime of formula 14-3. The oxime and ester groups in 14-3 can be reduced to an amine and alcohol, respectively, to form 14-4 with a suitable reducing reagent, such as with LAH in THF. Transformation of 14-4 to a carbamate of formula 14-5 can be achieved by reaction of 14-4 with CDI or another phosgene equivalent in the presence of a base like TEA and solvent such as DME. Deprotection of 14-5 produces 14-7 where $R^2$ is H. Alternatively, alkylation of the carbamate as described above (Scheme 13) affords 14-6, which can be deprotected, as described above, to give 14-7.

SCHEME 15

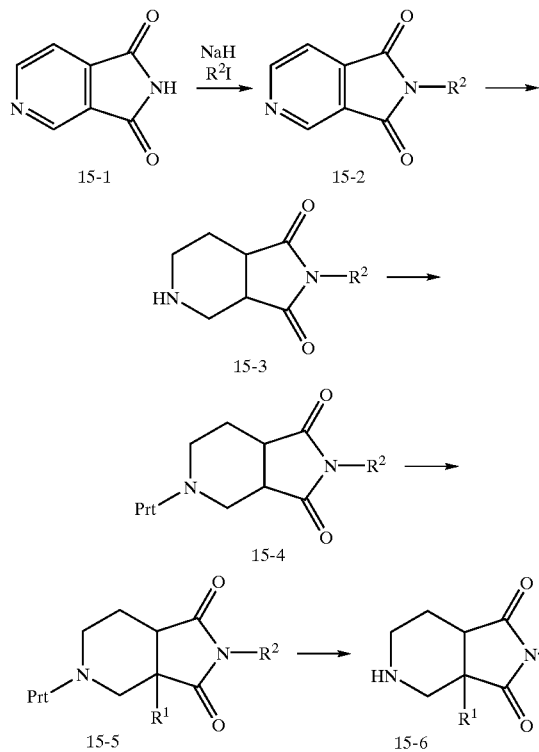

Treating 15-1 with a strong base such as sodium hydride in a suitable solvent such as DMF, followed by treatment with an alkylating agent, such as an alkyl halide, mesylate or tosylate, produces an N-substituted imide of formula 15-2. Reduction of the pyridine ring by catalytic hydrogenation, such as with Pd on carbon in an ethanolic HCl solution converts 15-2 to 15-3. Protection of the nitrogen, such as with a benzyl group, gives 15-4. A compound of the formula 15-5 can be generated upon deprotonation of 15-4 with a suitable strong base such as LHMDS in a solvent such as THF at a temperature of about −78° C., followed by alkylation with an electrophile such as an alkyl halide such as benzyl bromide. Cleavage of the protecting group, as described above, then gives 15-6.

SCHEME 16

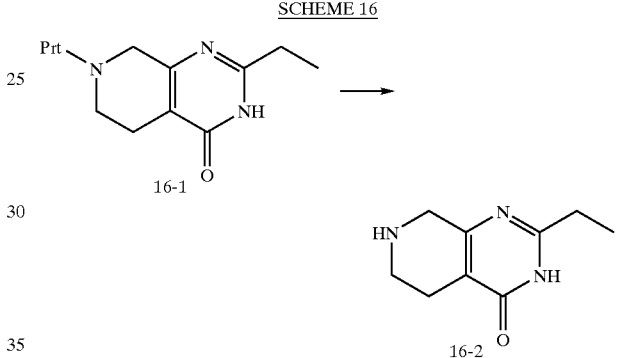

Deprotection of 16-1 as described above produces 16-2.

SCHEME 17

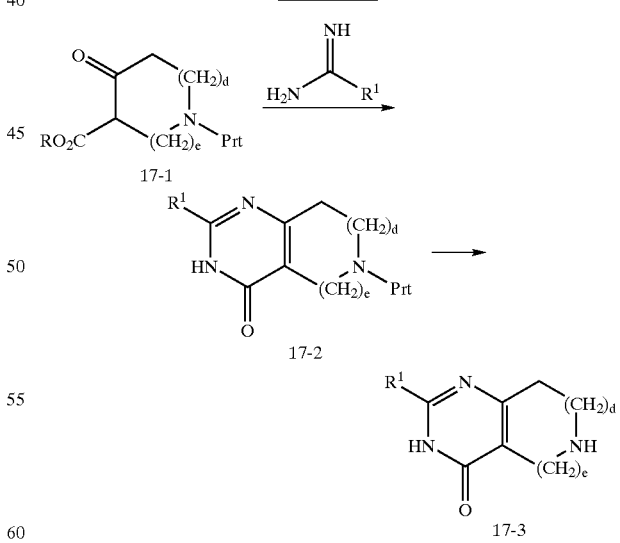

Condensation of 17-1 (R is an alkyl group) with an amidine in a solvent such as ethanol at an elevated temperature, preferably refluxing solvent, produces a heterocyclic intermediate of formula 17-2. Deprotection of 17-2, as described above, gives an intermediate of formula 17-3.

SCHEME 18

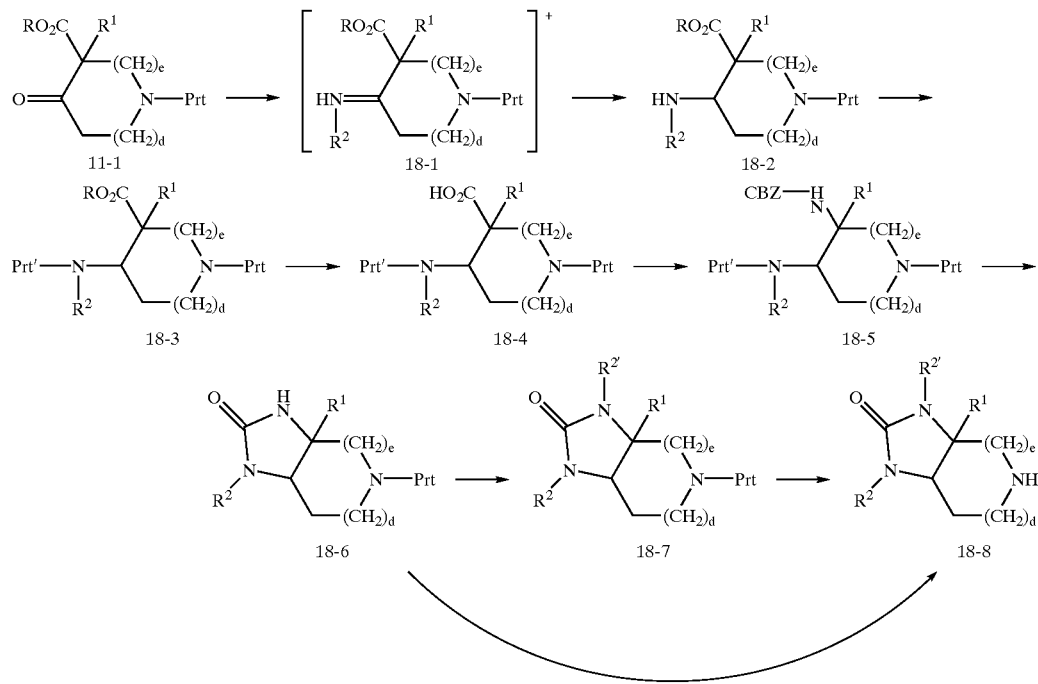

An intermediate amine of formula 18-2 can be prepared from a ketone of formula 11-1 (R is an alkyl group) by reductive amination as described above (see Scheme 8). Protection of the secondary amine in 18-2 produces 18-3. Intermediate carboxylic acids of formula 18-4 can be prepared by hydrolysis of the ester group of formula 18-3 (see Scheme 11). Transformation of 18-4 to 18-5 can be achieved through an intermediate acyl azide as described above (see Scheme 11). Cyclization of an intermediate of formula 18-5 at a suitable temperature after removing Prt' yields an intermediate urea of formula 18-6. Deprotection of 18-6 provides 18-8 where $R^{2'}$ is H. Alternatively, urea 18-6 can be alkylated by deprotonation with a strong base such as sodium hydride, LHMDS, or KHMDS in a suitable solvent such as DMF or THF followed by treatment with an alkylating agent such as an alkyl halide, mesylate or tosylate. Removal of the protecting group transforms 18-7 to 18-8 where $R^2$ and $R^{2'}$ are each alkyl.

SCHEME 19

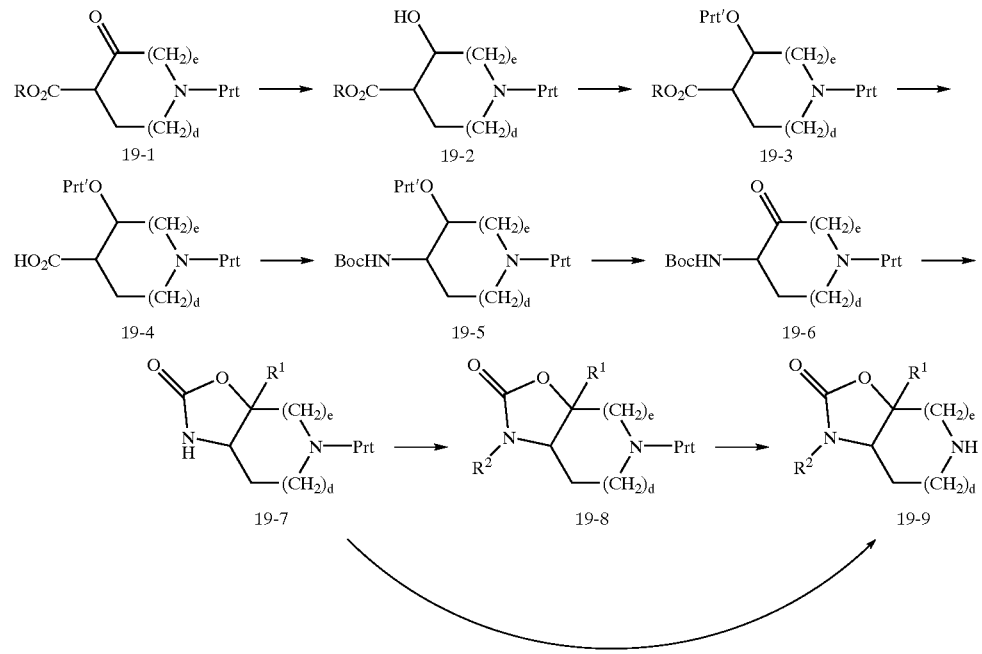

As illustrated in Scheme 19, reduction of a ketoester of formula 19-1, such as with sodium borohydride in methanol, preferably at 0° C., produces an alcohol of formula 19-2. An intermediate of formula 19-3 can be prepared by protection of the hydroxyl group in an intermediate of formula 19-2 with a suitable protecting group, such as forming a tetrahydropyranyl acetal or silyl ether. Transformation of the ester of formula 19-3 to amide 19-5 can be achieved as described above (see Scheme 11). Deprotection of the hydroxy group of 19-5 yields the free alcohol intermediate, which can be oxidized to an intermediate ketone of formula 19-6 with a suitable oxidizing agent, such as pyridinium chlorochromate or a Swern-type reagent (see Scheme 8). Transformation of 19-6 to a cyclized carbamate of formula 19-7 can be achieved by treating 19-6 with an alkyl metal, such as a Grignard reagent, in a suitable solvent such as THF, followed by cyclization. Removal of the protecting group then yields 19-9 wherein $R^2$ is H. Alternatively, the carbamate of 19-7 may be alkylated as described above (see Scheme 13) to afford 19-8, which can then be deprotected to provide 19-9. Those skilled in the art will recognize that an $R^{1A}$ substituent could have been introduced by alkylating ketoester 19-1.

SCHEME 20

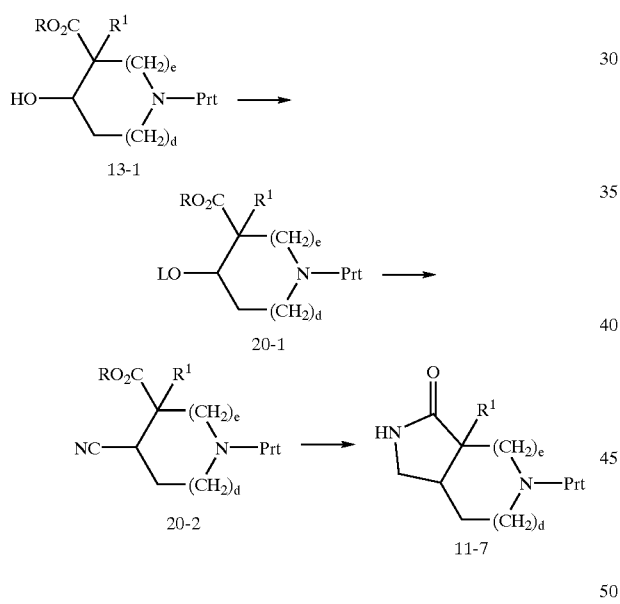

An alternate synthesis of lactam 11-7 is illustrated in Scheme 20. An alcohol of formula 13-1 can be converted to an intermediate nitrile of formula 20-2 by first activating the hydroxyl of 13-1 (R is an alkyl group), such as with methanesulfonyl chloride or methanesulfonic acid in a suitable solvent, such as methylene chloride in the presence of an amine base. Subsequent reaction of 20-1 (LO— is an activated hydroxyl) with a cyanide salt, such as potassium cyanide, then yields an intermediate nitrile of formula 20-2, which can be transformed to 11-7 by catalytic hydrogenation of the nitrile to amine, which then reacts with the ester group to form lactam (11-7). Those skilled in the art will recognize that an $R^{1A}$ substituent could be introduced by alkylating nitrile 20-2.

SCHEME 21

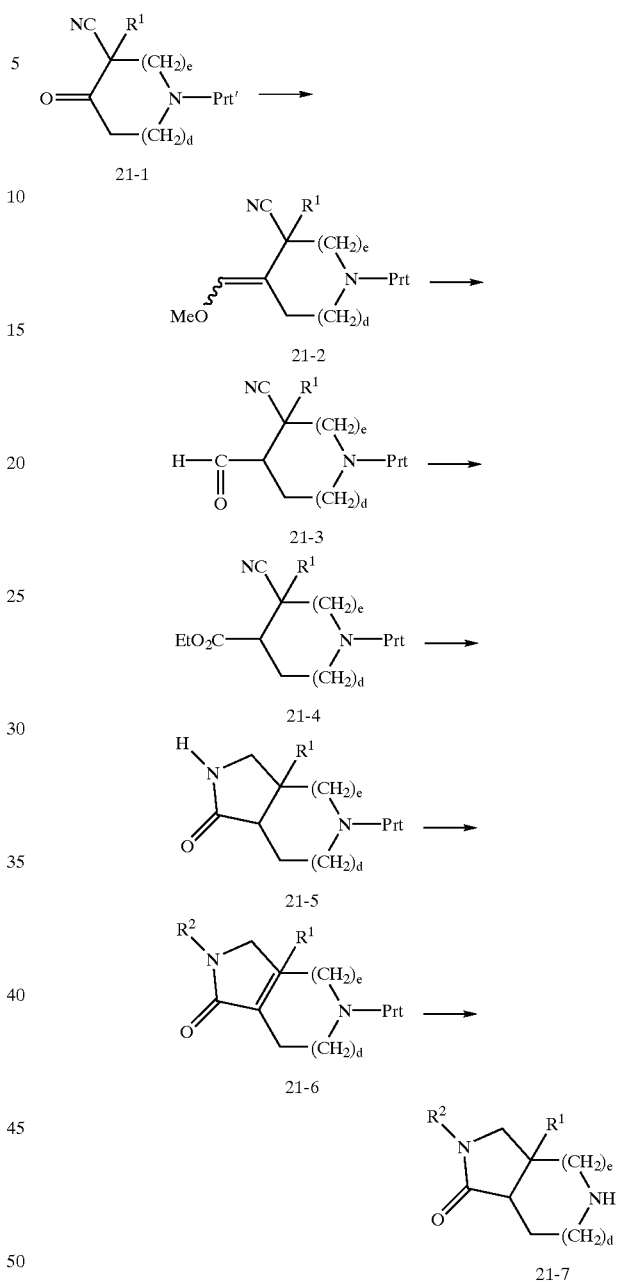

Nitriles of formula 21-1 can be prepared from esters, acid halides and acids of formula 11-1 by a variety of known methods (for examples, see R. Larock pages 976, 980 and 988 in Comprehensive Organic Transformations: A Guide to Functional Group Preparations, VCH Publishers, 1989).

Homologation of ketones of formula 21-1 to provide 21-3 as described above (Scheme 12) yields an aldehyde of formula 21-3. Oxidation of the aldehyde group in 21-3, such as with sodium hypochlorite, provides an acid which can be esterified to give 21-4 by a number of methods described above (Scheme 6). Reduction of the nitrile group in a compound of formula 21-4, such as by catalytic hydrogenation over Pd on carbon, gives an amine which will cyclize to give a lactam of formula 21-5. Deprotection of 21-5 yields 21-7, $R^2$ is H. Alternatively, alkylation of the amide of formula 21-5 as described above (Scheme 11) yields an N-substituted amide of formula 21-6, which can be deprotected to provide 21-7. Those skilled in the art will recognize that an $R^{1A}$ substituent could have been introduced by alkylating ester 21-4.

SCHEME 22

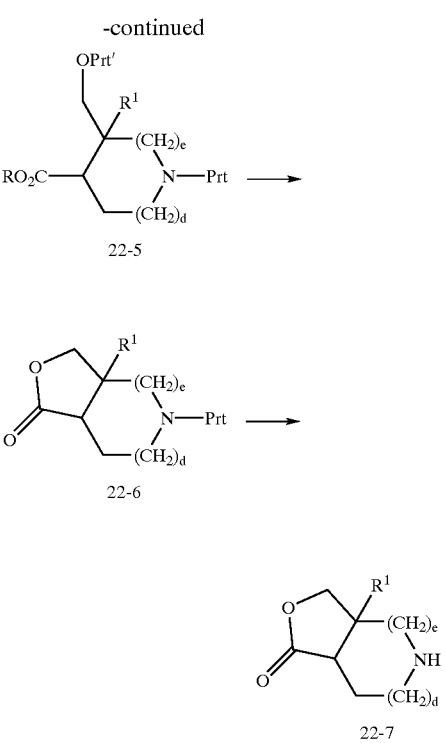

Intermediate alcohols of formula 22-1 can be prepared by reducing the ketone and ester groups of 11-1 (R is an alkyl group), such as with a metal borohydride or lithium aluminum hydride in a suitable solvent such as THF. Selective protection of the primary hydroxyl group of the intermediate of formula 22-1 with a suitable protecting group, such as a trialkylsilyl ether or pivaloyl ester gives a secondary alcohol of formula 22-2. An intermediate nitrile of formula 22-4 can be prepared from the alcohol of formula 22-2 by methods described above (see Scheme 20). An intermediate nitrile of formula 22-4 can be transformed to an ester of formula 22-5 by alcoholysis of nitrile 22-4, for instance with aqueous HCl or sodium hydroxide in ethanol. Removal of the alcohol protecting group and reaction of the hydroxyl group with the adjacent ester group in 22-5 forms a lactone of formula 22-6. Deprotection as described above yields 22-7. Those skilled in the art will recognize that an $R^{1A}$ substituent could have been introduced by treating ketone 11-1 with the appropriate alkyl metal reagent. Substitution ($R^9$, $R^{10}$) adjacent to the lactone oxygen could then be introduced by treating the ester with the appropriate alkyl metal reagent (the ketone would have to be reduced if $R^{1A}$ is not O).

SCHEME 23

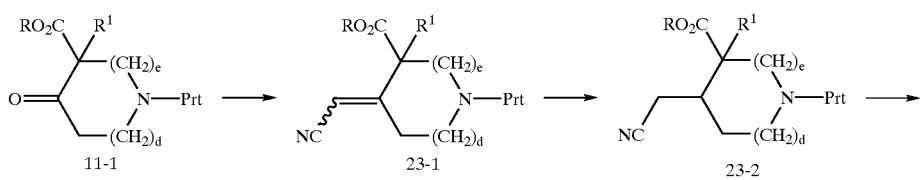

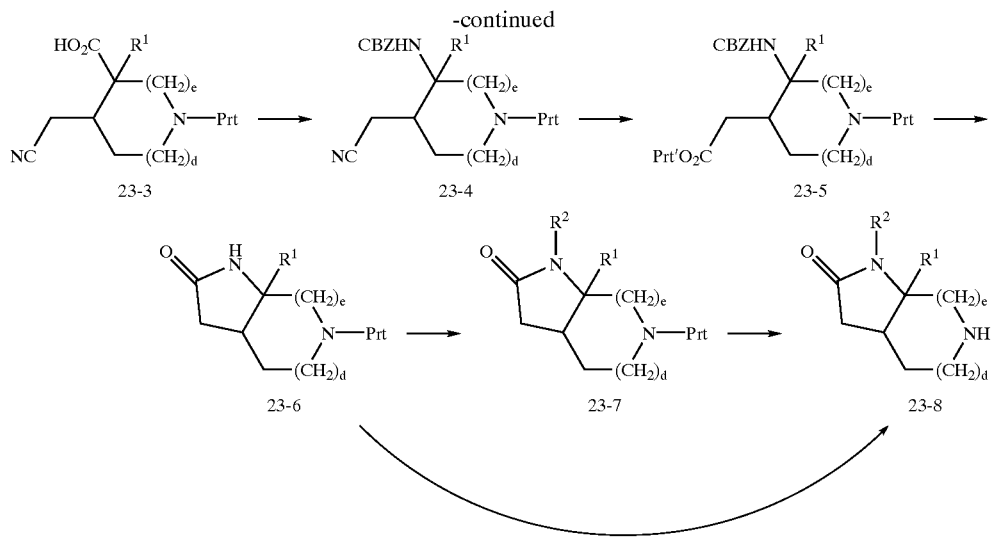

Intermediate α,β-unsaturated nitriles of formula 23-1 can be prepared by olefinating 11-1 (R is an alkyl group) with a reagent such as cyanomethyltriphenylphosphonium chloride and a strong base, such as KHMDS, in a suitable solvent, such as THF. Reduction of the double bond in 23-1, such as with sodium borohydride in pyridine, produces nitrile 23-2. The ester group of formula 23-2 can then be transformed to a carbamate of formula 23-4 by methods described above (see Scheme 11). Alcoholysis of the nitrile of 23-4 in an alcoholic solvent under acidic condition produces an ester of formula 23-5. A lactam of formula 23-6 can be prepared by removal of the CBZ protecting group, followed by cyclization of the amine with the adjacent ester group. Deprotection at this stage provides 23-8, $R^2$ is H. Alternatively, alkylation of the amide (according to Scheme 11) provides an N-substituted lactam, which can be converted to 23-8 by deprotection as described above. One skilled in the art will recognize that an $R^{1A}$ substituent could have been introduced by conjugate addition to the unsaturated nitrile (23-1), such as with an alkyl cuprate. In addition, $R^9$, $R^{10}$ substituents can be introduced next to the lactam carbonyl by alkylating nitrile 23-2.

SCHEME 24

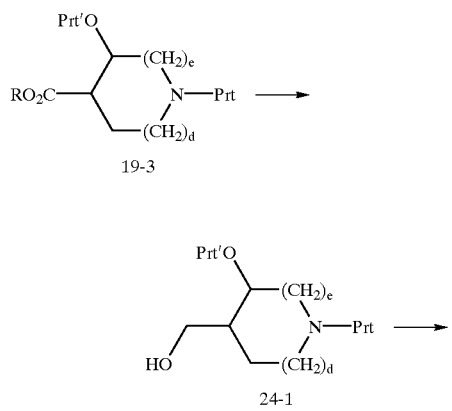

As illustrated in Scheme 24, an alcohol of formula 24-1 can be prepared from 19-3 (R is an alkyl group) by reduction of the ester with a reducing reagent such as lithium borohydride in a solvent such as THF. A nitrile of formula 24-2 can be prepared from the alcohols of formula 24-1 by methods described above (see Scheme 20). Deprotection of the alcohol of 24-2 followed by oxidation of the hydroxyl as previously described (see Scheme 19) produces a ketone 24-3. Treating 24-3 with an alkyl metal such as a Grignard reagent in a suitable solvent such as THF gives an intermediate of formula 24-4. The cyano group of 24-4 can then be converted to an ester by alcoholysis as described above (Scheme 22). Reaction of the tertiary alcohol with the neighboring ester forms a lactone which can then be deprotected to give 24-5. One skilled in the art will recognize that an $R^{1A}$ substituent could be introduced by alkylating ester 19-3. In addition, $R^9$, $R^{10}$ substituents could be introduced adjacent to the lactone carbonyl by alkylation before final deprotection.

SCHEME 25

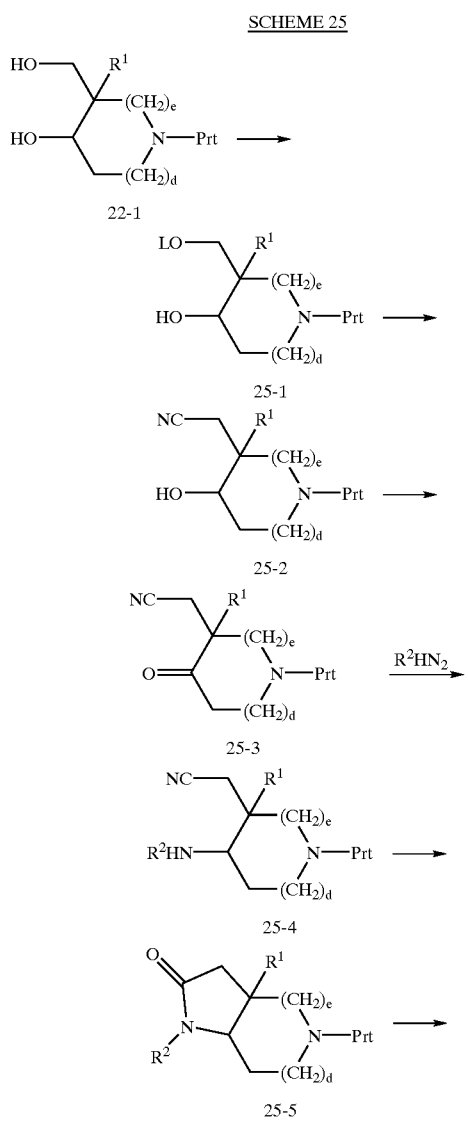

Intermediate of formula 25-1 (LO— is an activated hydroxyl) can be prepared by selective activation of the primary hydroxyl, for instance by tosylation of the less hindered hydroxyl group of 20-1 with tosyl chloride in a suitable solvent. Treating 25-1 with a reagent such as potassium cyanide in a suitable solvent produces a nitrile of formula 25-2. Oxidation of the alcohol (see Scheme 19) of formula 25-2 gives a ketone of formula 25-3. Transformation of 25-3 to 25-4 can be achieved by reductive amination as was described above (see Scheme 8). The cyano amine of formula 25-4 can be converted to a lactam of formula 25-5 by treating 25-4 with a strong acid or base in a protic solvent such as ethanol. Removal of the protecting group on the secondary nitrogen can then provide lactam 25-6. One skilled in the art will recognize that $R^9$, $R^{10}$ substituents could be introduced by alkylation of lactam 25-5.

SCHEME 26

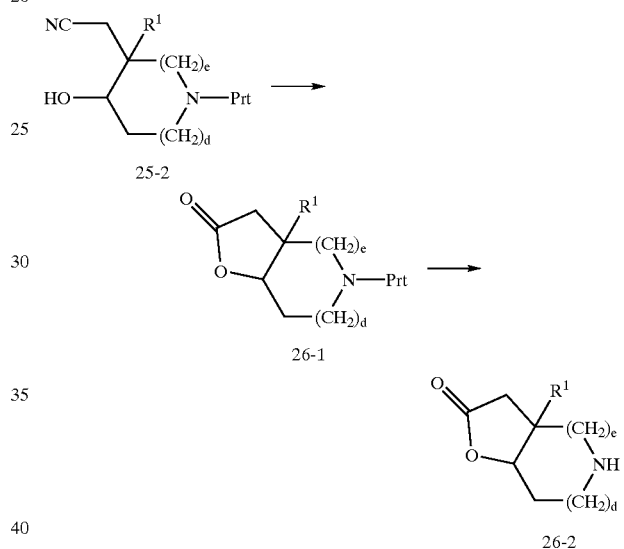

A lactone of formula 26-1 can be prepared by treating a cyano alcohol of formula 25-2 with a strong acid such as HCl, or a strong base such as NaOH, in a protic solvent such as EtOH. Deprotection, as described above, of the secondary amine of formula 26-1 gives 26-2. One skilled in the art will recognize that $R^9$, $R^{10}$ substituents can be introduced by alkylation of lactone 26-1.

SCHEME 27

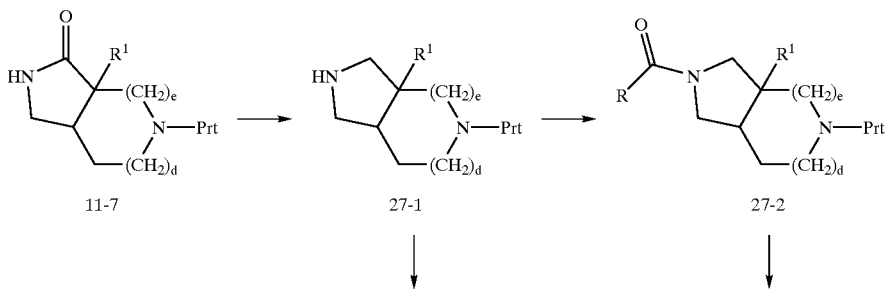

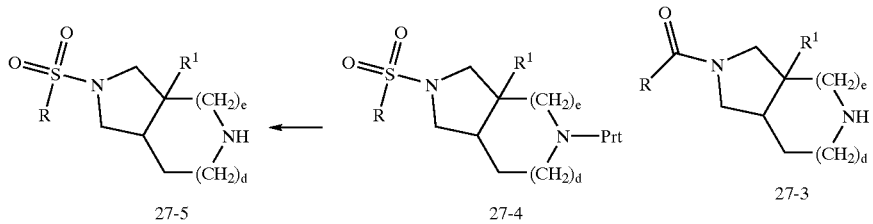

Intermediates of formula 27-1 can be prepared by reducing a lactam of formula 11-7 to a pyrrolidine with a suitable reducing reagent such as borane or lithium aluminum hydride in a suitable solvent such as THF. Treating 27-1 with an acyl chloride of formula RCOCl (where R is an alkyl group) in a suitable solvent produces an intermediate amide of formula 27-2. Removal of the protecting group of the amide of formula 27-2 by the method described previously gives an amide of formula 27-3.

A sulfonamide of formula 27-5 can be prepared by treating 27-1 with a sulfonyl halide such as tosyl chloride in the presence of a base such as pyridine to yield 27-4, followed by removal of the protecting group as previously described.

SCHEME 28

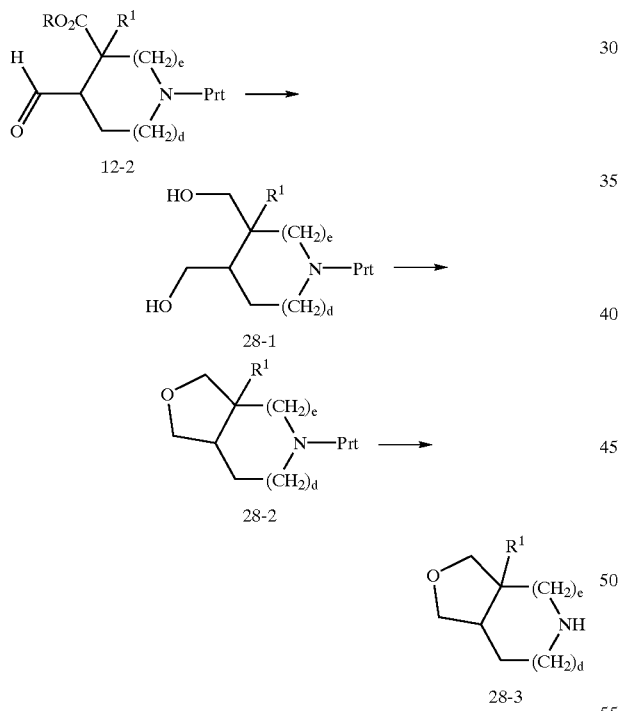

Intermediate diols of formula 28-1 (R is an alkyl group) can be prepared by treating 12-2 with a suitable reducing agent, such as lithium borohydride, in an appropriate solvent, such as THF. Methods for converting diol 28-1 to furan 28-2 include dehydration under acidic conditions, dehydration with a reagent such as $Ph_3P(OEt)_2$, or reaction with a reagent such as toluenesulfonylchloride in the presence of a base followed by displacement of the activated alcohol with the remaining hydroxyl group. Removal of the protecting group from 28-2 subsequently forms a compound of formula 28-3. One skilled in the art will recognize that an $R^{1A}$ substituent can be added by alkylating aldehyde 12-2. In addition, $R^9$, $R^{10}$ substituents can be introduced by treating 12-2 with an alkyl metal reagent.

SCHEME 29

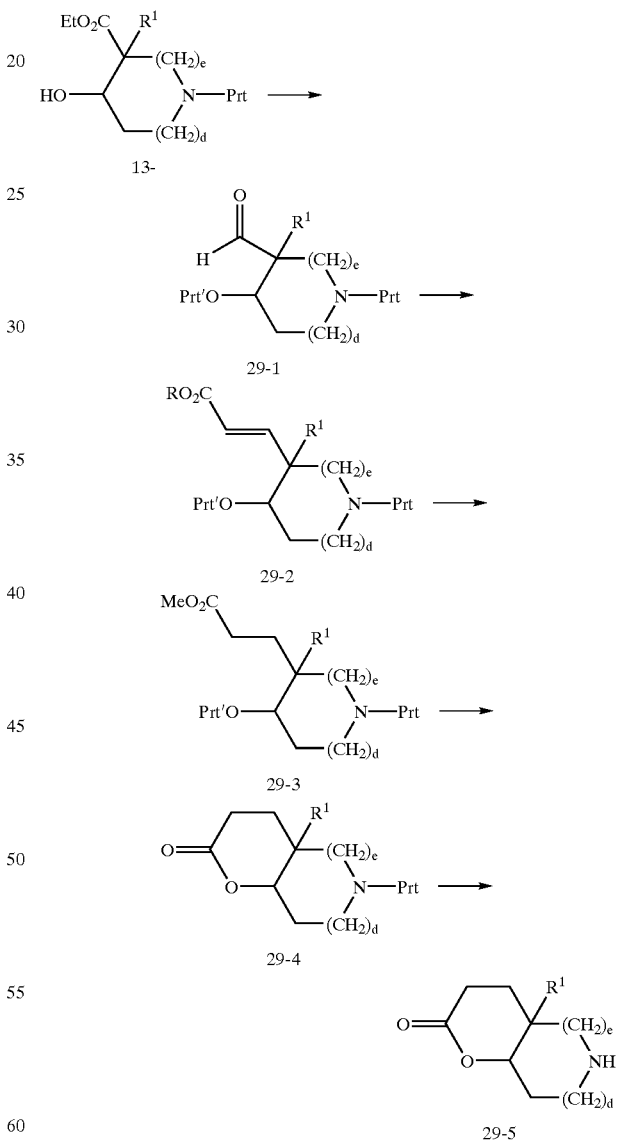

Intermediate aldehydes of formula 29-1 can be prepared by protecting the secondary alcohol of 13-1 such as with a silyl ether, followed by reduction of the ester with a reducing reagent such as diisobutylaluminum hydride at −78° C. in a suitable solvent. Alternatively, 13-1 can be reduced to the primary alcohol with a reagent such as lithium borohydride, and then oxidized to the aldehyde with a variety of reagents described above (see Scheme 8). Homologation of aldehydes of formula 29-1 to saturated esters of formula 29-3 can be performed as previously described (see similar homologation of ketones in Scheme 11). Deprotection of the secondary alcohol of 29-3, followed by cyclization produces lactones of formula 29-4. Deprotection of 29-4 will then give 29-5. An $R^9$ substituent β to the lactone carbonyl may be introduced by conjugate addition to unsaturated ester 29-2, such as with an alkyl cuprate. In addition, $R^9$, $R^{10}$ substituents could be introduced next to the lactone carbonyl by alkylating lactone 29-4.

amine as previously described (see Scheme 8) produces intermediate 30-3. Cyclization of 30-3 at a suitable temperature yields a lactam of formula 30-4, which can be deprotected to give 30-5. One skilled in the art will recognize that $R^9$, $R^{10}$ substituents can be introduced by alkylation of lactam 30-4.

SCHEME 30

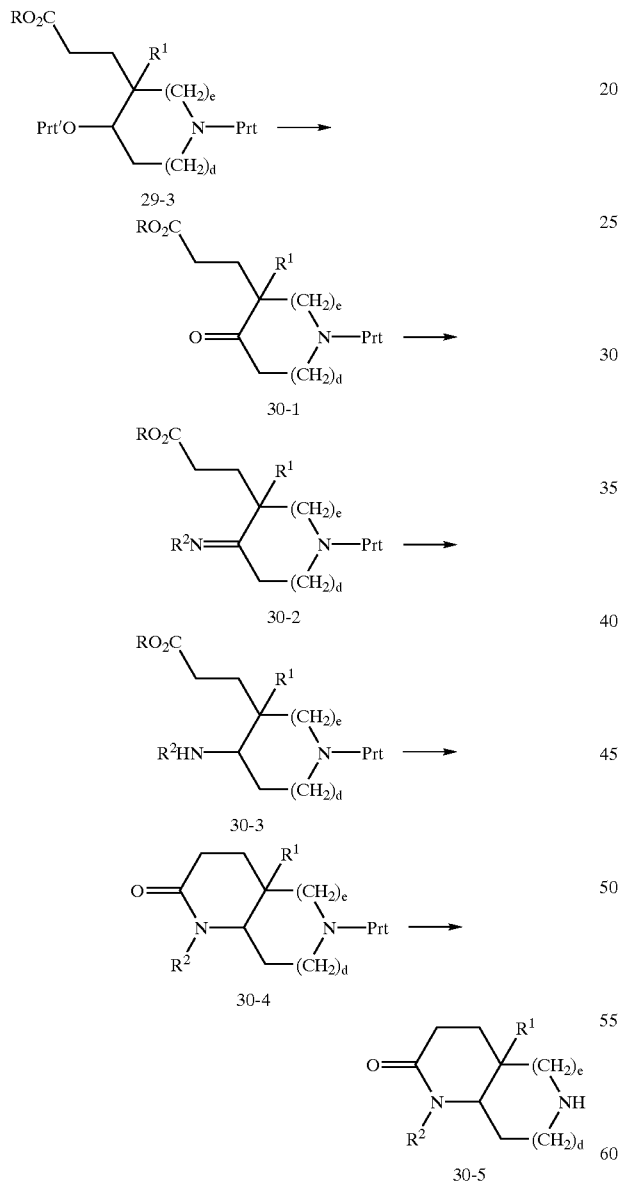

SCHEME 31

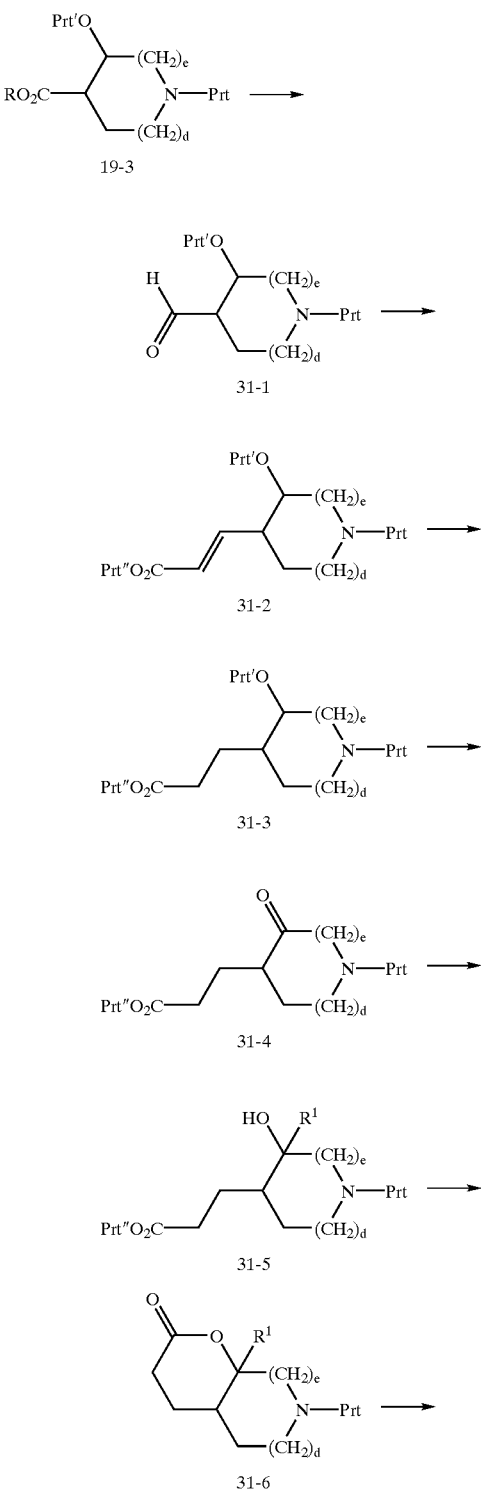

Intermediate ketones of formula 30-1 can be prepared by deprotecting the secondary hydroxyl of 29-3 (R is an alkyl group), followed by oxidation of the alcohol to a ketone (see Scheme 19). Reductive amination of 30-1 with a primary

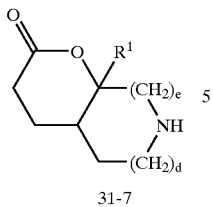

Homologation of 19-3 (R is an alkyl group) to an ester of formula 31-3 can be performed analogously to routes described above (see Scheme 29). Removal of Prt' of 31-3 gives a secondary alcohol which can be oxidized as was previously described (see Scheme 19) to produce a ketone of formula 31-4. Treating 31-4 with an alkyl metal reagent, such as a Grignard reagent, in a suitable solvent produces intermediate 31-5, which can be cyclized to form lactone 31-6. Removal of the protecting group then produces 31-7. One skilled in the art will recognize that an $R^{1A}$ substituent may be introduced by alkylation of ester 19-3. A substituent β to the lactone carbonyl may be introduced by conjugate addition to unsaturated ester 31-2, such as with an alkyl cuprate. Also, $R^9$, $R^{10}$ substituents can be introduced next to the lactone by alkylation of 31-6.

SCHEME 32

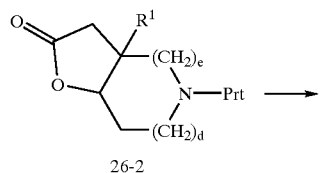

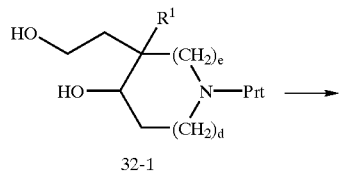

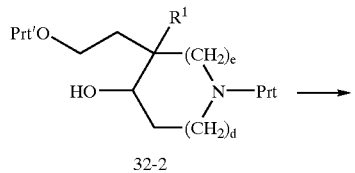

Intermediate diols of formula 32-1 can be prepared by reducing the lactone group of 26-2 with a reagent such as lithium aluminum hydride in a suitable solvent such as THF at a suitable temperature. Selective protection at the less hindered hydroxy group of 32-1, such as with t-butyldimethylsilyl chloride using triethylamine in the presence of DMAP in a solvent such as dichloromethane, produces alcohol 32-2. Conversion of alcohol 32-2 to a nitrile of formula 32-4 may be accomplished as described above (LO— is an activated hydroxyl group) (see Scheme 20). Alcoholysis of the cyano group of formula 32-4 (see Scheme 22), deprotection of the alcohol, and subsequent lactonization forms lactones of formula 32-5. Deprotection of an amine of formula 32-5 gives a lactone of formula 32-6. One skilled in the art will recognize that $R^9$, $R^{10}$ substituents can be introduced β- to the ring oxygen in lactone 32-6 by alkylating lactone 26-2. Substitution α to the lactone ring oxygen may be introduced by treating 26-2 with an alkyl metal reagent.

SCHEME 33

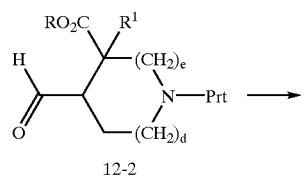 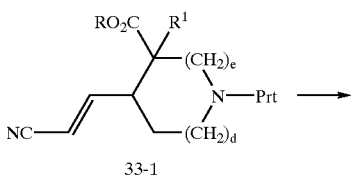 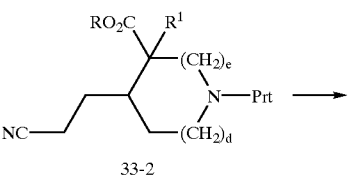

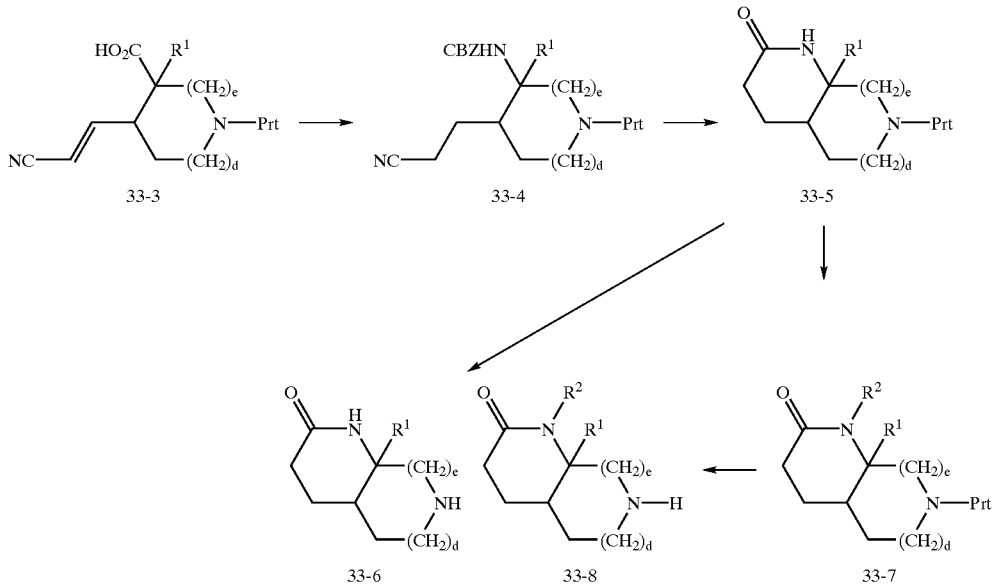

Intermediate nitriles of formula 33-2 can be prepared by homologating 12-2 (R is an alkyl group), analogous to the ketone homologation described in Scheme 23. Conversion of ester 33-2 to carbamates of formula 33-4 can be accomplished as described above (see Scheme 11). Alcoholysis of the cyano group of 33-4 as described above (see Scheme 22) and removal of the CBZ protecting group, followed by cyclization of the amine with the adjacent ester group produces a lactam of formula 33-5. Deprotection of 33-5 gives the lactam of formula 33-6.

Alternatively, alkylation of 33-5 in the usual fashion (see Scheme 11) gives 33-7, which can be deprotected to give 33-8. One skilled in the art will recognize that an $R^{1A}$ substituent may be introduced by alkylating aldehyde 12-2. An $R^9$ substituent may be introduced by conjugate addition to the unsaturated nitrile (33-1). $R^9$, $R^{10}$ substitution can be introduced next to the lactam by alkylation of 33-7.

SCHEME 34

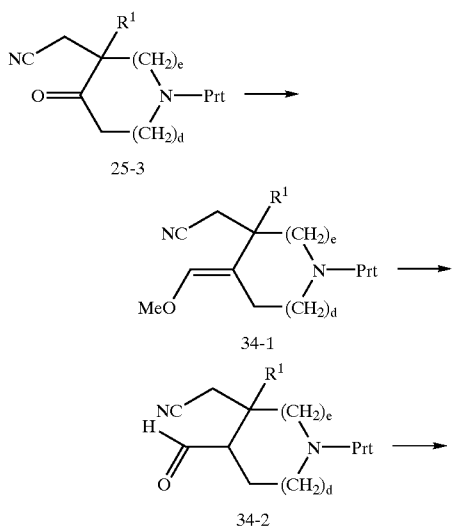

The homologation of 25-3 to give a lactam of formula 34-5 can be analogously performed according to the procedures described in Scheme 21. One skilled in the art will recognize that an $R^{1A}$ substituent may be introduced by alkylating 34-4 (R is an alkyl group). $R^9$, $R^{10}$ substitution may be introduced by alkylating nitrile 34-1.

SCHEME 35

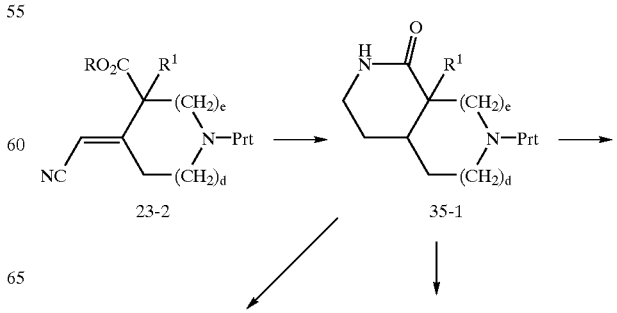

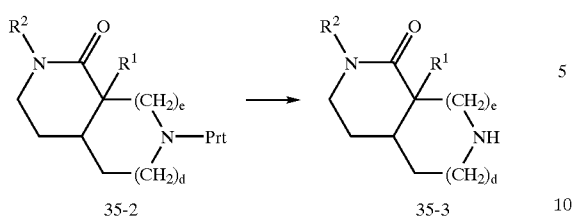

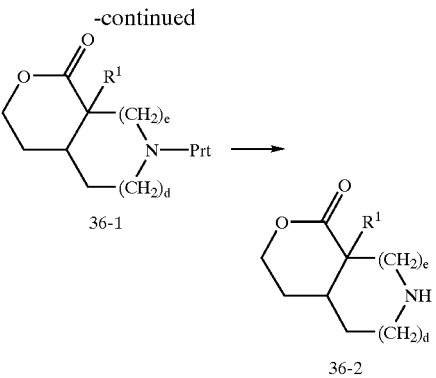

As illustrated in Scheme 35, catalytic hydrogenation of a nitrile of formula 23-2 (R is an alkyl group) gives an amine, followed by cyclization of the amine with the adjacent ester group to give lactams of formula 35-1. Deprotection of 35-1 gives 35-3, $R^2$ is H. Alternatively, alkylation of lactam 35-1 as described above (see Scheme 11) provides N-substituted amides of formula 35-2. Deprotection of 35-2 affords 35-3. One skilled in the art will recognize that an $R^{1A}$ substituent may be introduced by conjugate addition to the unsaturated nitrile.

SCHEME 36

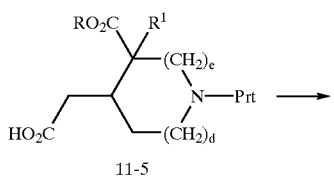

As illustrated in Scheme 36, selective reduction of the carboxylic acid group of 11-5 to an alcohol, such as by treating 11-5 (R is an alkyl group) with borane in a suitable solvent, followed by cyclization of the alcohol and ester produces a lactone of the formula 36-1. Deprotection of 36-1 then gives 36-2.

SCHEME 37

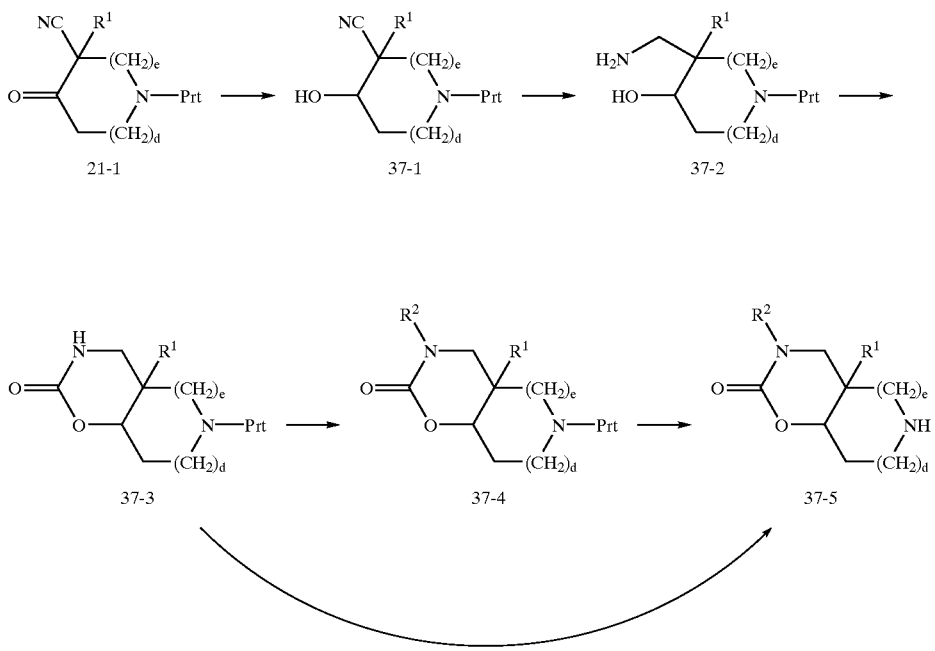

Intermediate alcohols of formula 37-1 can be prepared by reducing the ketone of 21-1, such as with sodium borohydride in a solvent such as methanol at a temperature of about 0° C. Reduction of the cyano group to an amine, such as by catalytic hydrogenation, affords aminoalcohol 37-2. Treating 37-2 with a reagent like CDI or other phosgene equivalent in the presence of a base like TEA (see Scheme 14) produces a cyclized carbamate of formula 37-3. Deprotection of 37-3 then gives 37-5, $R^2$ is H. Alternatively, 37-3 may be alkylated as described above (see Scheme 13) to give an N-substituted carbamate of formula 37-4, which is deprotected to give 37-5. One skilled in the art will recognize that an $R^{1A}$ substituent may be introduced by addition to ketone 21-1.

SCHEME 38

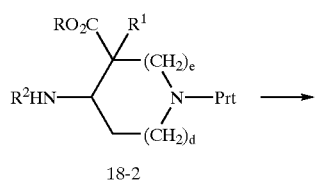

Intermediate aminoalcohols of formula 38-1 can be prepared by reducing an ester of formula 18-2 (R is an alkyl group), such as with lithium borohydride. Treating 38-1 with a phosgene equivalent as described in Scheme 14 produces a cyclized carbamate of formula 38-2. Deprotection subsequently provides 38-3.

SCHEME 39

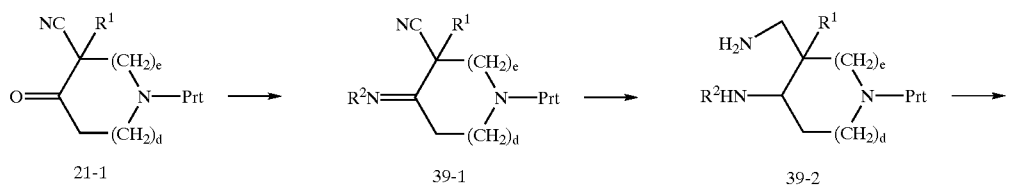

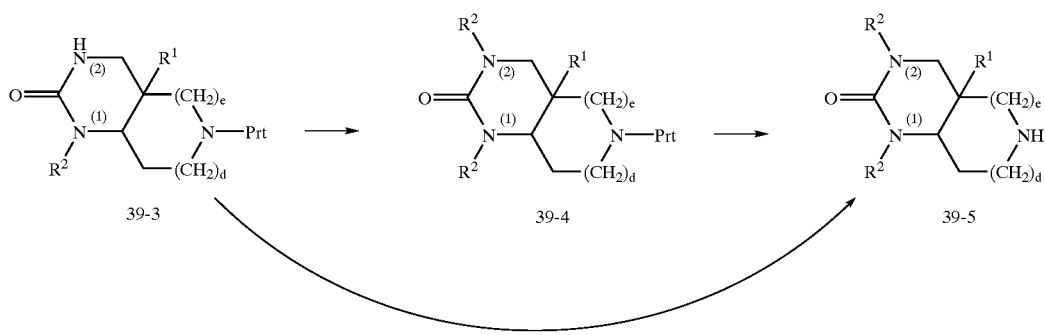

-continued

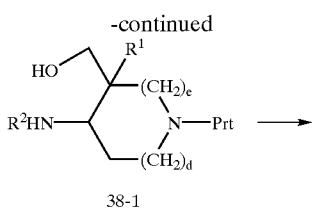

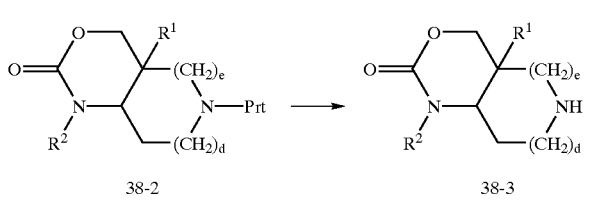

Intermediate imines of formula 39-1 can be prepared by condensing the ketone of 21-1 with a primary amine under dehydrating conditions, such as azeotropic distillation using a solvent like benzene. Catalytic hydrogenation to reduce the nitrile and imine converts 39-1 to 39-2. Treating 39-2 with a reagent like CDI, phosgene, or triphosgene in the presence of a base like TEA produces the cyclized and N-substituted ureas of formula 39-3. Deprotection of this material provides 39-5 where the $R^2$ attached to the (2)-nitrogen is H. Alkylation of 39-3, such as with sodium hydride and an alkyl halide produces the N,N'-substituted ureas of formula 39-4, which can be deprotected to provide 39-5 where the $R^2$ attached to the (2)-nitrogen is an alkyl group.

SCHEME 40

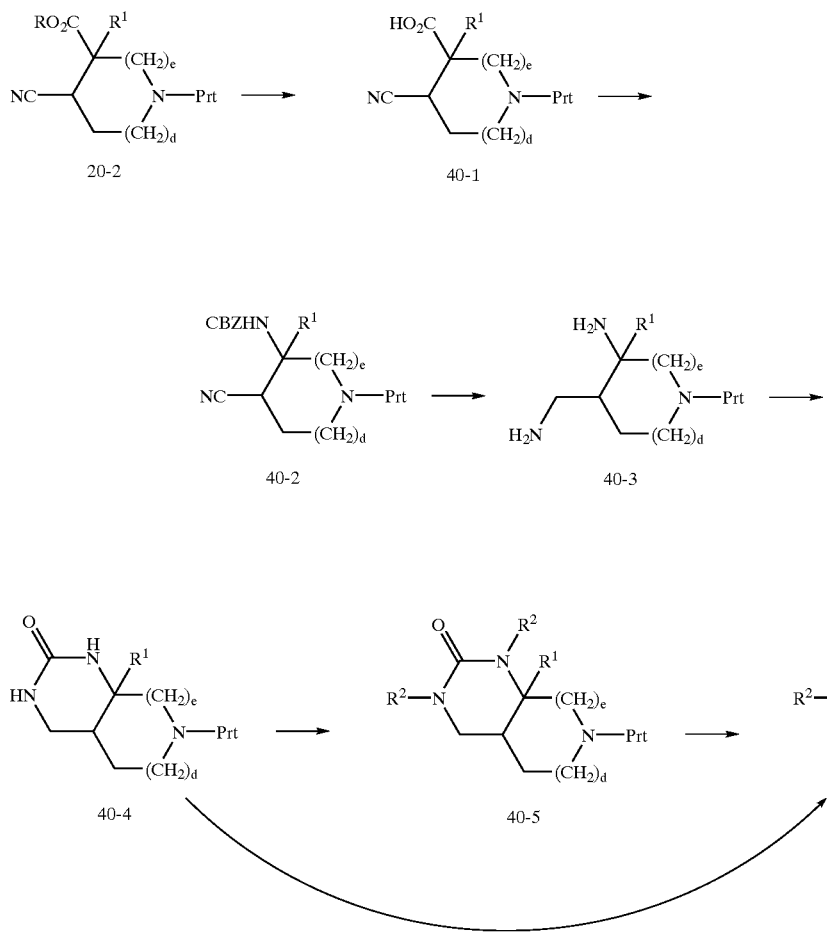

As illustrated in Scheme 40, ester 20-2 (R is an alkyl group) can be converted to carbamate 40-2 as described above (see Scheme 11). Catalytic hydrogenation of 40-2 will reduce the nitrile and cleave the CBZ group to provide a diamine of formula 40-3. Acylating 40-3 with a reagent such as CDI, phosgene, or triphosgene in the presence of a base like TEA produces the cyclized ureas of formula 40-4. Deprotection at this stage provides 40-6 where each $R^2$ is H. Alternatively, alkylation of 40-4, such as by deprotonation with a strong base like sodium hydride followed by reaction with an alkylating reagent like an alkyl halide, tosylate or mesylate produces the N,N'-substituted ureas of formula 40-5. Deprotection then provides 40-6 where each $R^2$ is alkyl. One skilled in the art will recognize that an $R^{1A}$ substituent may be introduced by alkylation of nitrile 20-2.

SCHEME 41

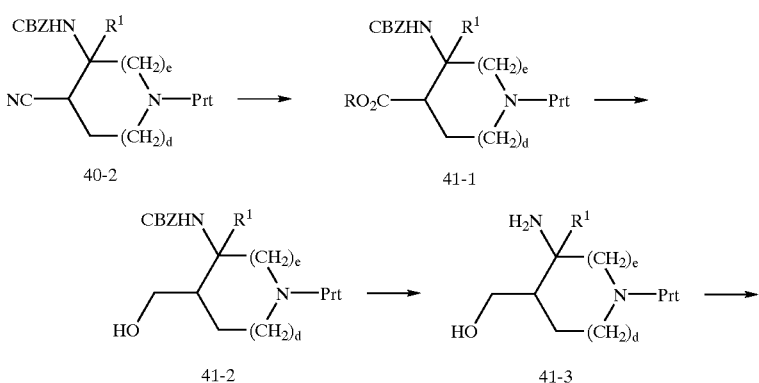

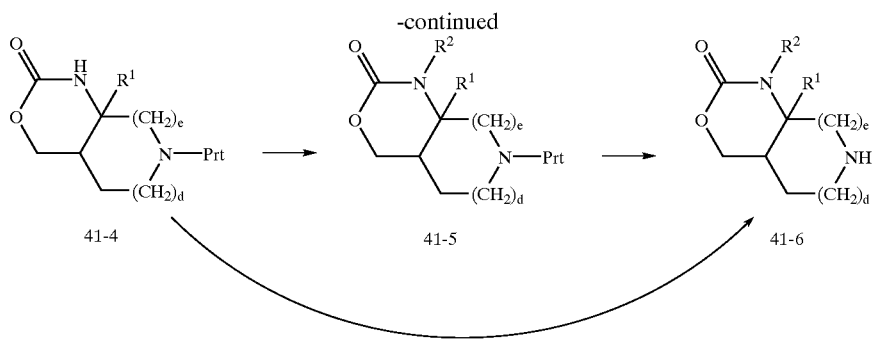

Intermediate esters of formula 41-1 (R is an alkyl group) can be prepared by alcoholysis of the cyano group in 40-2 with ethanolic HCl. Reducing the ester group in 41-1, such as with lithium borohydride in THF produces an alcohol of formula 41-2. Catalytic hydrogenation to remove the CBZ group to yield an amine as previously described converts 41-2 to 41-3. Treating 41-3 with a reagent like CDI or other phosgene equivalent in the presence of a base like TEA produces a carbamate of formula 41-4. Deprotection at this stage provides 41-6 where $R^2$ is H. Alternatively, transformation of 41-4 to N-substituted carbamates of formula 41-5 can be achieved by deprotonating 41-4 with a strong base such as sodium hydride in a solvent like DMF, followed by alkylation with a reagent such as an alkyl halide, tosylate or mesylate. Deprotection then converts 41-5 to 41-6 where $R^2$ is alkyl.

Reaction of a ketoester of formula 42-1 with a chiral amine such as alpha-methylbenzylamine with a suitable aldehyde such as formaldehyde, or reaction of a vinyl ketoester of formula 42-2 with a chiral amine such as alpha-methylbenzylamine with a suitable aldehyde such as formaldehyde, affords a compound of formula 42-3 via a double Mannich reaction. Compound 42-3 is equivalent to 11-1 where d and e are 1, and may be deprotected with a suitable catalyst such as palladium in the presence of hydrogen to give 42-4. In addition, 42-3 could be isolated as a single diastereomer (by selective cyclization or separation of diastereomers), thereby providing 42-4 as a single enantiomer.

SCHEME 42

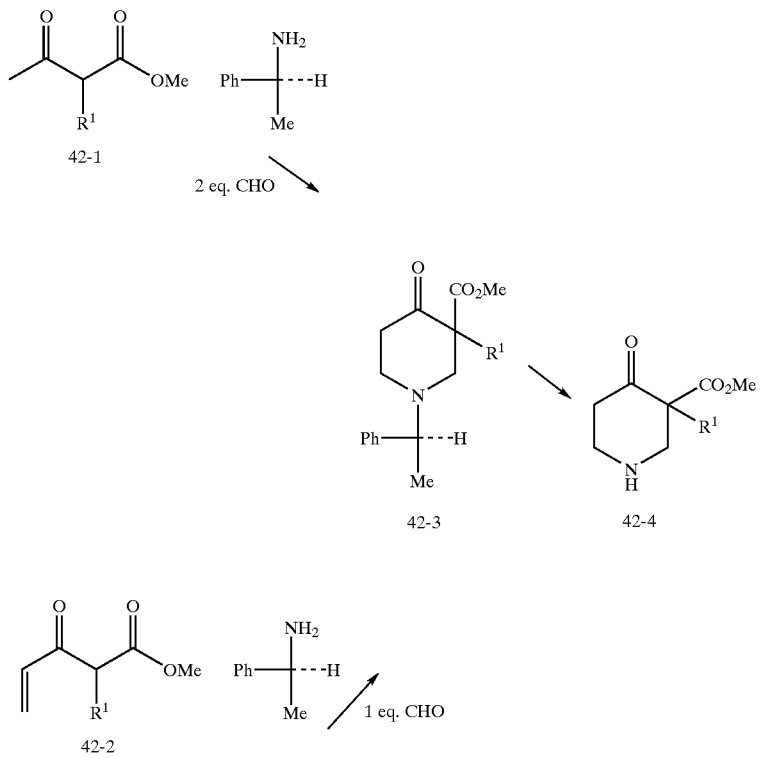

SCHEME 43

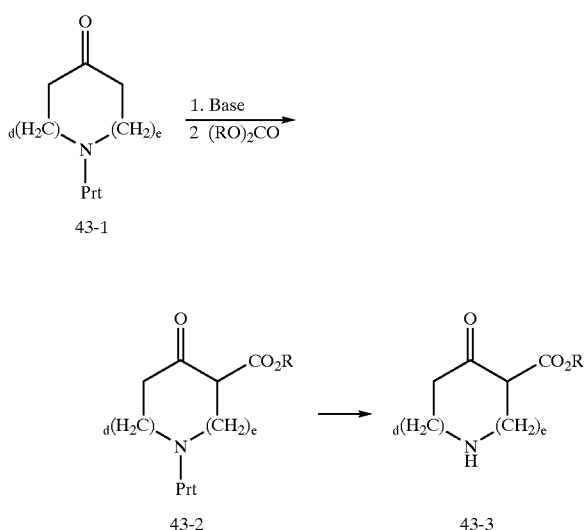

Treatment of a compound of formula 43-1 with a base such as sodium hydride in a solvent such as DMF followed by treatment with diethylcarbonate generates the ethyl ester of compound 43-2 (R is an alkyl group). Deprotection of the amine transforms 43-2 into 43-3. It will be recognized by one skilled in the art that 19-1 is equivalent to 43-3.

SCHEME 44

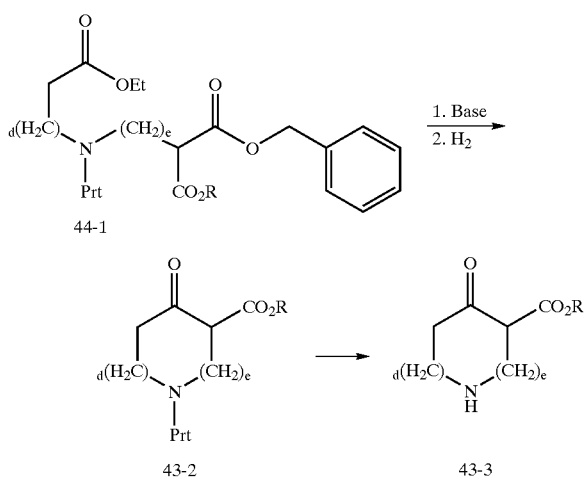

Treatment of a malonic ester of formula 44-1 (R is an alkyl group) with a base such as sodium hydride in a solvent such as DMF and subsequent hydrogenolysis of the benzyl group with hydrogen and a catalyst such as palladium in a suitable solvent such as methanol produces the ester of formula 43-2. Deprotection of the amine generates compounds of formula 43-3. It will be recognized by one skilled in the art that 19-1 is equivalent to 43-3.

SCHEME 45

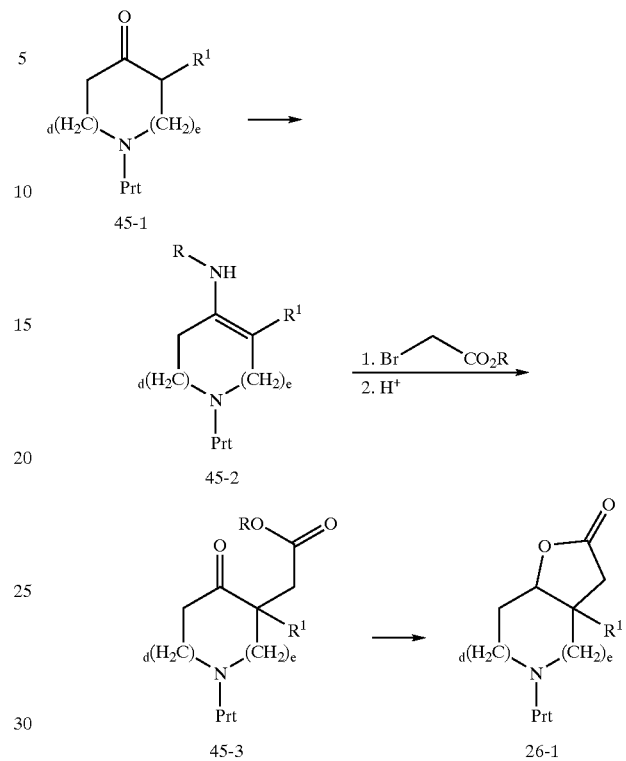

Treatment of a ketone of formula 45-1 with a secondary amine such as piperidine in a suitable solvent such as benzene with removal of water affords an enamine of formula 45-2 (each R is an alkyl group). Alkylation of the enamine with an alpha-haloester such as ethylbromoacetate in a suitable solvent such as benzene or THF using a suitable base such as LDA or $NaN(SiMe_3)_2$ affords a ketoester of formula 45-3. Reduction with a mild reducing agent such as sodium borohydride in methanol and subsequent cyclization then affords 26-1.

SCHEME 46

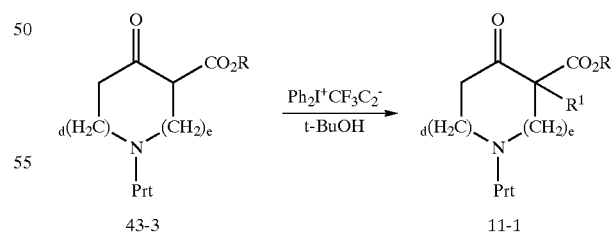

Treatment of a ketoester of formula 43-3 (R is an alkyl group) with an iodonium salt such as diphenyliodonium trifluoroacetate in a suitable solvent such as t-butanol generates a ketoester of formula 11-1 where $R^1$ is phenyl. See Synthesis, (9), 1984 p. 709 for a detailed description.

SCHEME 47

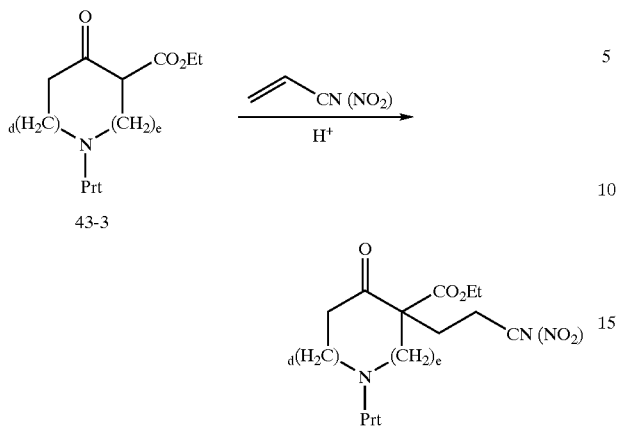

Treatment of a ketoester of formula 43-3 with an olefin such as acrylonitrile or nitroethylene generates a ketoester of formula 11-1 where $R^1$ is $CH_2CH_2CN$ or $R^1$ is $CH_2CH_2NO_2$.

SCHEME 48

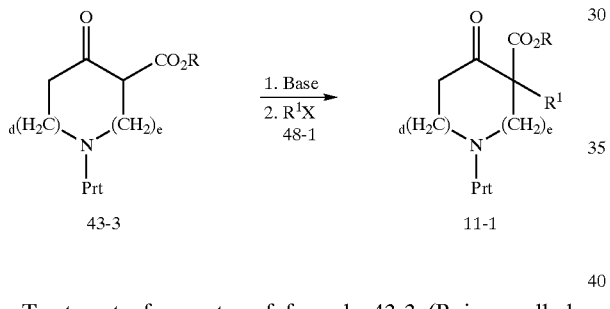

Treatment of an ester of formula 43-3 (R is an alkyl group) with a base such as sodium hydride in a solvent such as DMF followed by an alkyl halide 48-1 generates a compound of formula 11-1 as illustrated in Scheme 48.

SCHEME 49

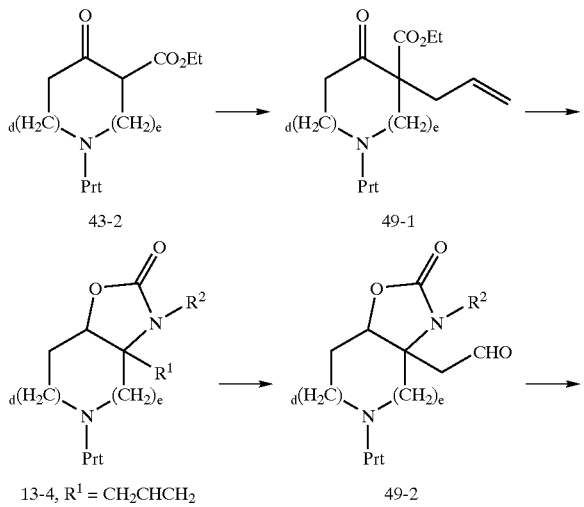

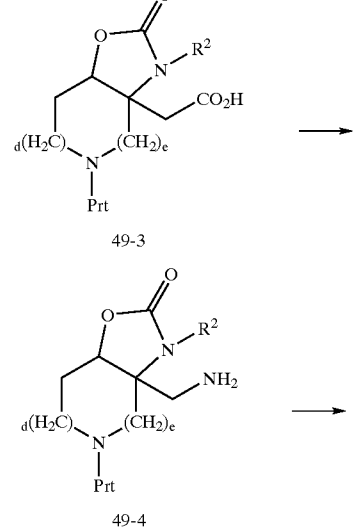

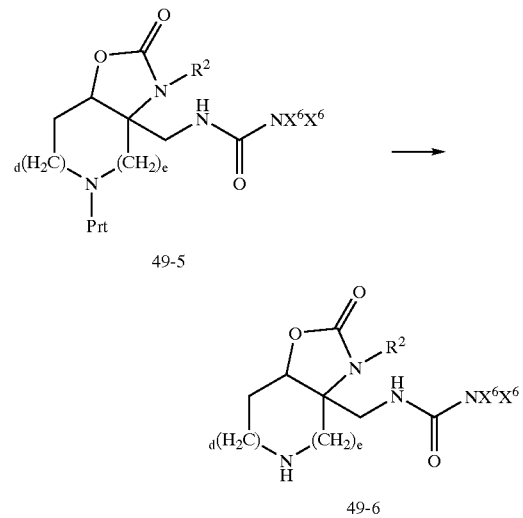

Treatment of a ketoester of formula 43-2 with allyl bromide and a suitable base such as sodium hydride in a suitable solvent such as DMF affords a ketoester of formula 49-1 (11-1, $R^2$ is allyl). Compound 49-1 may then be converted to 13-4 as described in Scheme 13. Ozonolysis of 13-4 in a suitable solvent such as methylene chloride followed by treatment with a reducing agent such as dimethylsulfide affords an aldehyde of formula 49-2. Oxidation of 49-2 affords a carboxylic acid of formula 49-3. Curtius rearrangement of 49-3, followed by hydrolysis of the intermediate isocyanate affords a primary amine of formula 49-4. Treatment of a compound of formula 49-4 with an isocyanate or carbamate affords a urea of formula 49-5. Deprotection of the nitrogen affords compounds of formula 49-6 (e.g., 13-5, wherein $R^1$ is $CH_2NHCONX^6X^6$). Those skilled in the art will recognize that other heterocycles, prepared in previous schemes, could be transformed analogously to the conversion of 13-4 to 49-6.

SCHEME 50

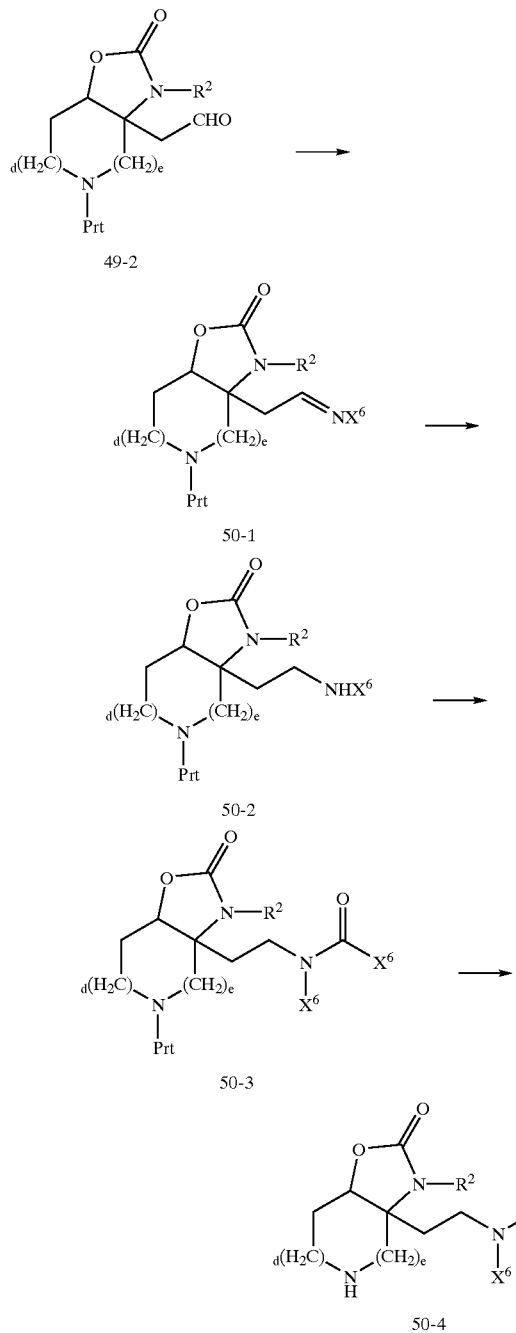

Treatment of a compound of formula 49-2 with a primary amine of formula $HNX^6$ affords an imine of formula 50-1. Reduction of a compound of formula 50-1 affords a compound of formula 50-2. Treatment of a compound of formula 50-2 with an acylating agent affords a compound of formula 50-3. Deprotection of the nitrogen affords compounds of formula 50-4 (13-5, $R^1$ is $CH_2CH_2NX^6COX^6$). Those skilled in the art will recognize that other heterocycles, prepared in previous schemes, could be transformed in a manner analogous to the conversion of 49-2 to 50-4.

SCHEME 51

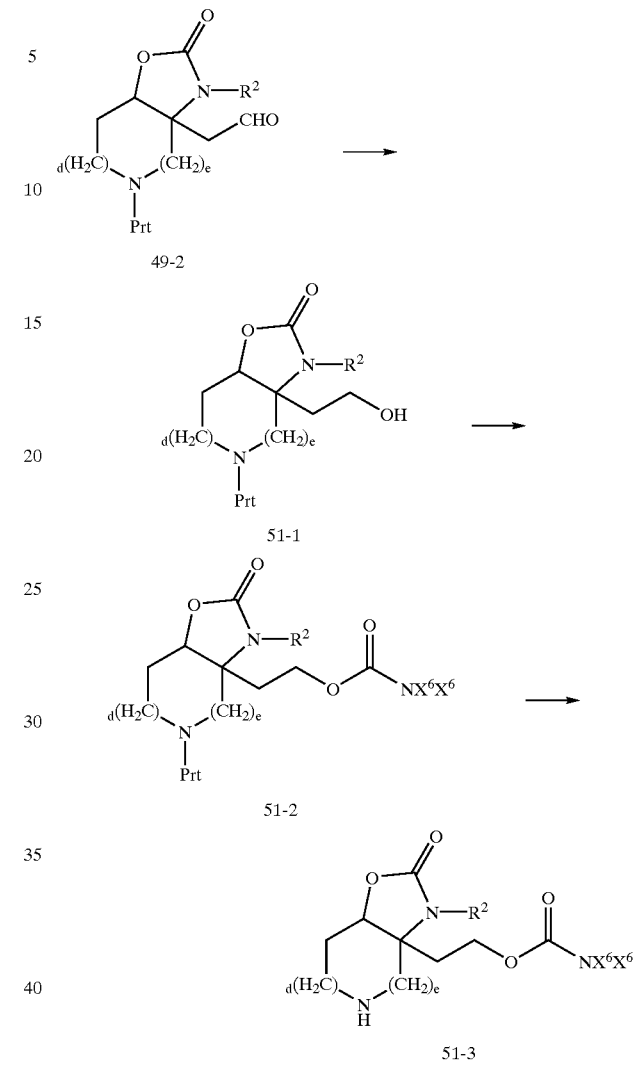

Treatment of a compound of formula 49-2 with a reducing agent such as sodium borohydride affords a compound of formula 51-1. Reaction of 51-1 with an acylating agent such as an isocyanate or carbamate affords compounds of formula 51-2. Deprotection of the nitrogen affords compounds of formula 51-3. Those skilled in the art will recognize that other heterocycles, prepared in previous schemes, could be transformed in a manner analogous to the conversion of 49-2 to 51-3.

SCHEME 52

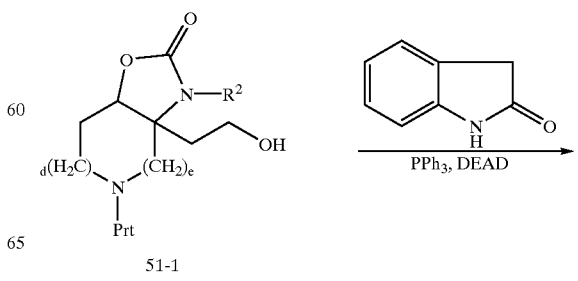

SCHEME 54

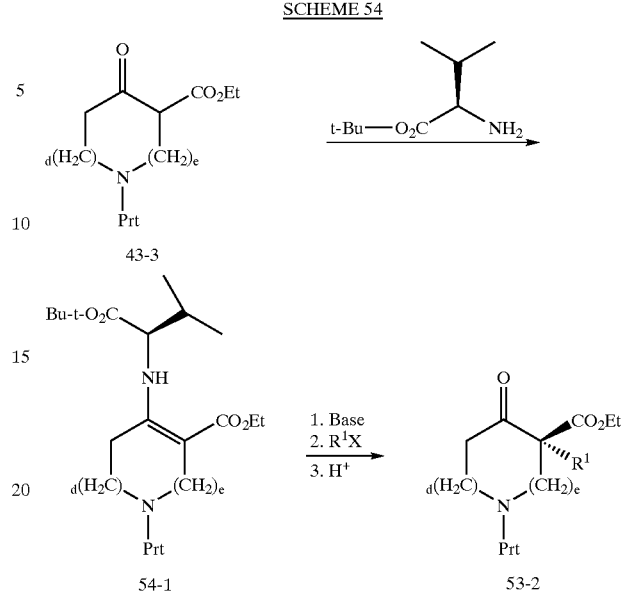

Treatment of a ketoester of formula 43-3 with a chiral amino acid ester such as valine t-butyl ester affords a chiral enamine of formula 54-1. Alkylation of 54-1 with an alkyl halide in the presence of a base such as LDA followed by acid-catalyzed hydrolysis of the enamine affords chiral ketoesters of formula 53-2.

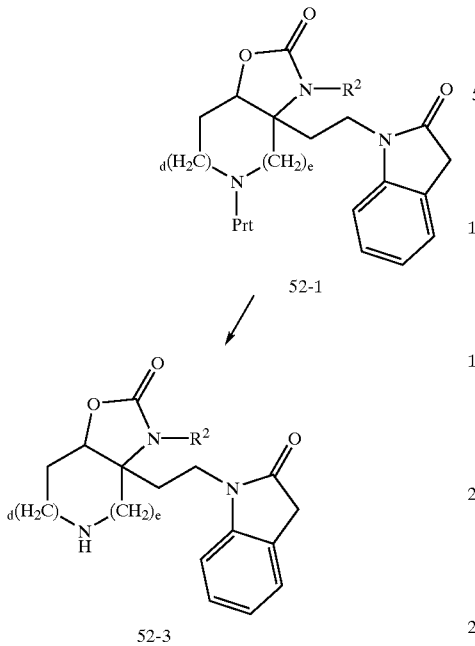

Treatment of a compound of formula 51-1 with a phosphine such as triphenyl phosphine and an azo compound such as diethylazodicarboxylate and an oxindole affords a compound of formula 52-1. Deprotection of the nitrogen affords the compound of formula 52-3. Those skilled in the art will recognize that other heterocycles, prepared in previous schemes, could be transformed in a manner analogous to the conversion of 49-2 to 52-3.

SCHEME 53

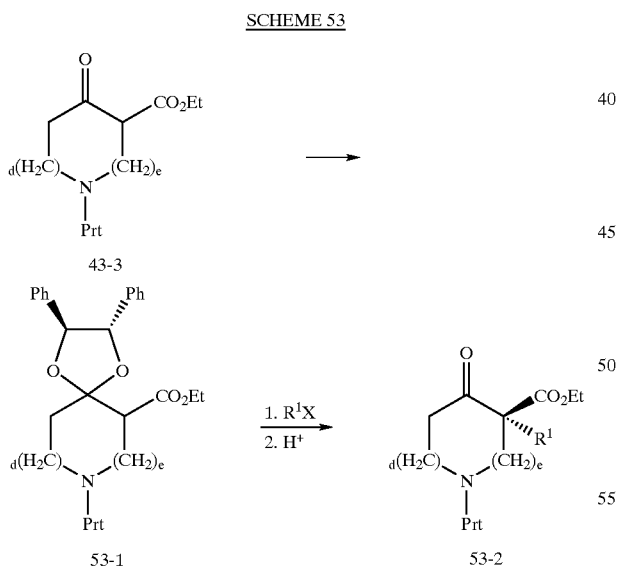

Treatment of a ketoester of formula 43-3 with a chiral diol and acid catalyst with removal of water in a suitable solvent such as benzene affords a chiral ketal like formula 53-1. Alkylation of 53-1 with an alkyl halide in the presence of a base such as LDA followed by acid-catalyzed hydrolysis of the ketal affords chiral ketoesters of formula 53-2. Ketoester 53-2 is a single enantiomer of 11-1 and may be homologated in a similar fashion to give various heterocycles.

SCHEME 55

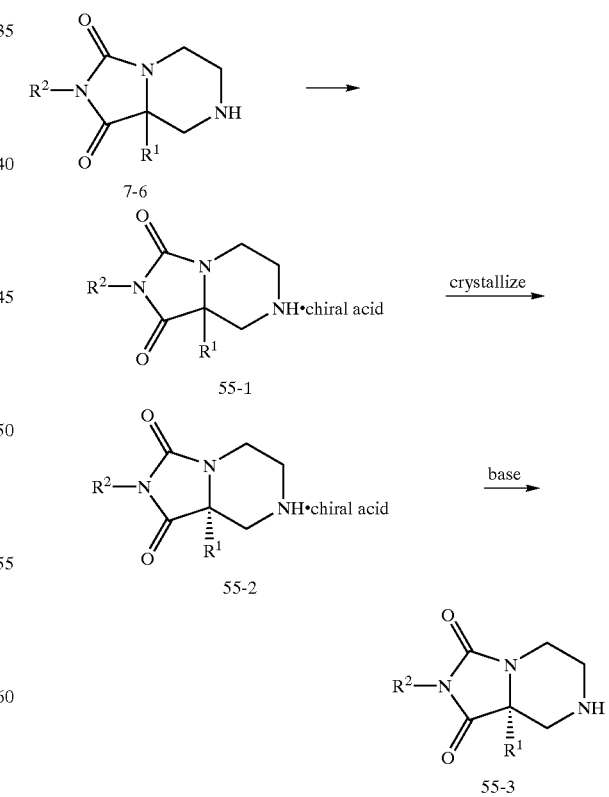

Salt formation of 7-6 with a chiral acid affords a mixture of diastereomeric salts of formula 55-1. Crystallization of the diastereomeric salts affords the acid salt of chiral compounds of formula 55-2. Decomposition of the salt 55-2 with base liberates chiral compounds of formula 55-3. This resolution scheme could be applied to the resolution of other HET-bicyclic compounds described above.

to compounds of formula 57-3 as previously described by Welch, Willard M. (J. Org. Chem 47; 5; 1982; 886–888).

SCHEME 56

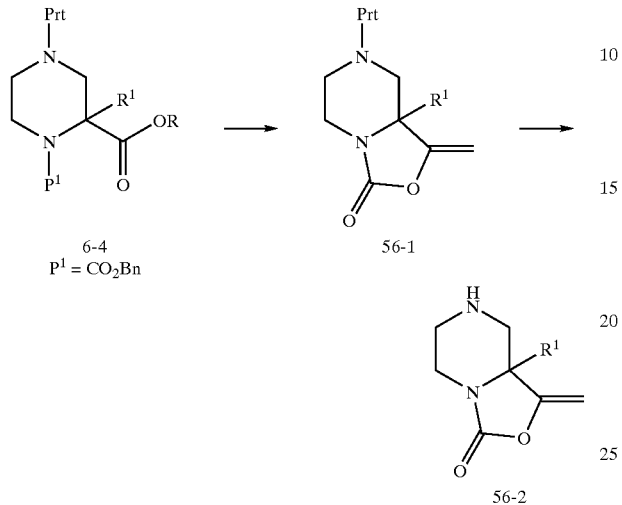

As illustrated in Scheme 56, treatment of 6-4 ($P^1$ is $CO_2Bn$) with an alkyl metal reagent like methyl magnesium bromide affords 56-1. Deprotection as usual then affords 56-2.

SCHEME 57

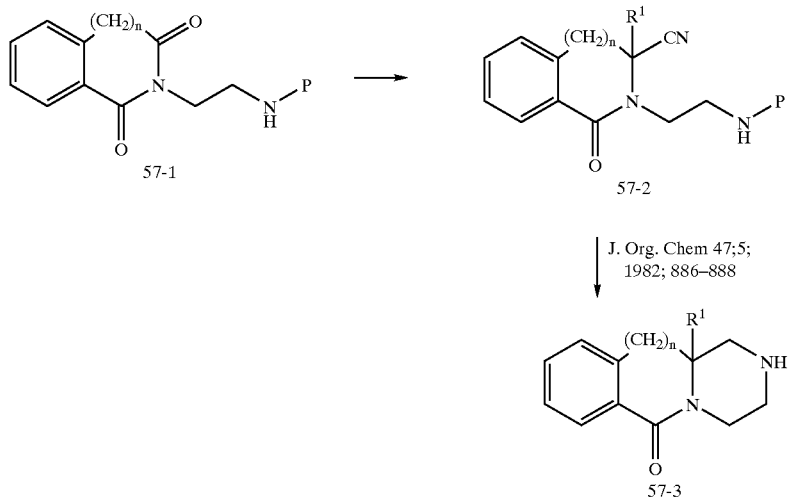

Compounds of formula 57-3 can be prepared from known phthalic or homophthalic anhydrides by methods previously described by Welch, Willard M. (J. Org. Chem 47; 5; 1982; 886–888. J. Org. Chem.; 47; 5; 1982; 886–888) or Machida, Minoru et al. (Heterocycles; 14; 9; 1980; 1255–1258). Alternatively, the analogous phthalimides or homophthalimides of formula 57-1 can be treated with the appropriate hydride reagent (e.g., $NaBH_4$) or organometallic reagent (e.g., methyl Grignard), followed by treatment with sodium or potassium cyanide to produce an intermediate of the formula 57-2. Compounds of formula 57-2 can be converted

SCHEME 58

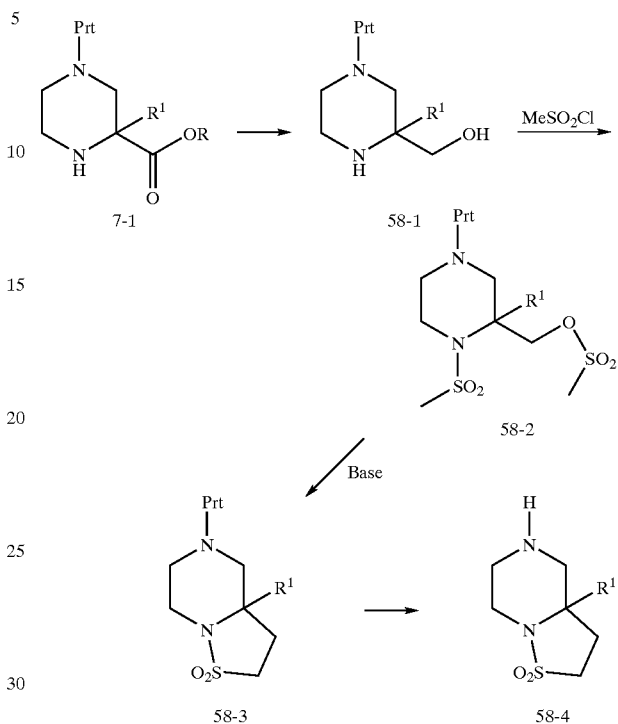

As illustrated in Scheme 58, intermediates of formula 58-4 can be prepared in four steps from compounds of formula 7-1. Compounds of formula 7-1 are treated with a suitable reducing agent such as Super Hydride® in a suitable solvent, preferably THF at a temperature of −20 to 50° C., preferably at around 25° C. to give compounds of formula 58-1. Amino alcohols of formula 58-1 are then treated with at least two equivalents of methanesulfonyl chloride and at least two equivalents of a suitable base, preferably pyridine in a suitable solvent, preferably pyridine at a temperature of −20 to 50° C. preferably around 25° C. to give intermediates of formula 58-2. Treatment of 58-2 with a strong base, preferably sec-butyllithium at a temperature of around −78° C. followed by warming to a temperature of around 25° C. affords intermediates of formula 58-3. Removal of the protecting group as described above, transforms 58-3 into 58-4.

SCHEME 59

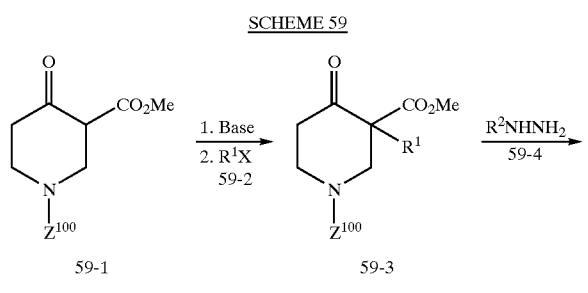

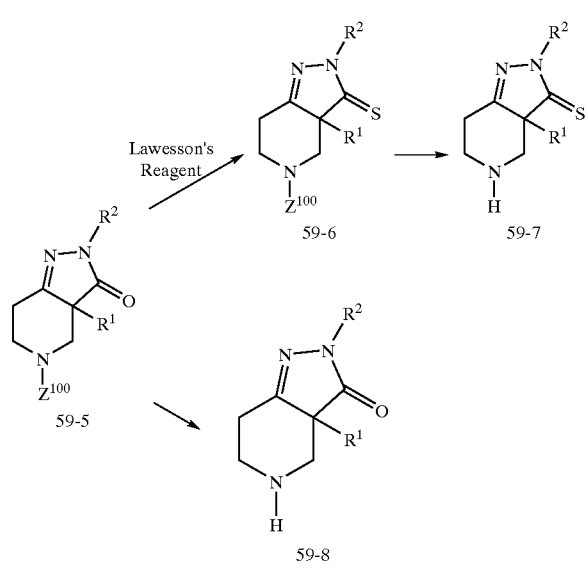

As illustrated in Scheme 59, treatment of an ester of formula 59-1 with a base such as sodium hydride in a solvent such as DMF followed by an alkyl halide 59-2 generates a compound of formula 59-3. Treating a compound of formula 59-3 with a hydrazine of formula 59-4 such as hydrazine or methyl-hydrazine in a solvent such as refluxing ethanol, followed by concentration and heating the residue in toluene at temperatures at or near reflux results in a compound of formula 59-5. Alternatively, 59-3 can be treated with a salt of a hydrazine in the presence of sodium acetate in refluxing ethanol to give 59-5. Deprotection of the amine generates a compound of formula 59-8. Thioamides of formula 59-6 can be formed by treating 59-5 with Lawesson's reagent in refluxing toluene or benzene. Removal of the protecting group transforms 59-6 into 59-7.

SCHEME 60

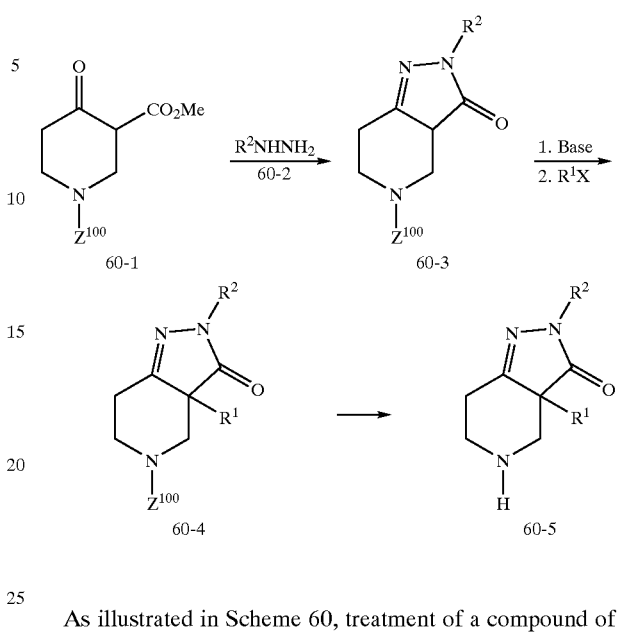

As illustrated in Scheme 60, treatment of a compound of formula 60-1 with a hydrazine of formula 60-2 in a solvent such as refluxing ethanol, followed by concentration and heating the residue in toluene at temperatures at or near reflux results in compounds of formula 60-3. Alternatively, 60-1 can be treated with a salt of a hydrazine in the presence of sodium acetate in refluxing ethanol to give 60-3. The amide of formula 60-3 can be treated with a base such as sodium hydride in a solvent such as DMF followed by an alkyl halide to give 60-4. Deprotection of the amine generates a compound of formula 60-5.

SCHEME 61

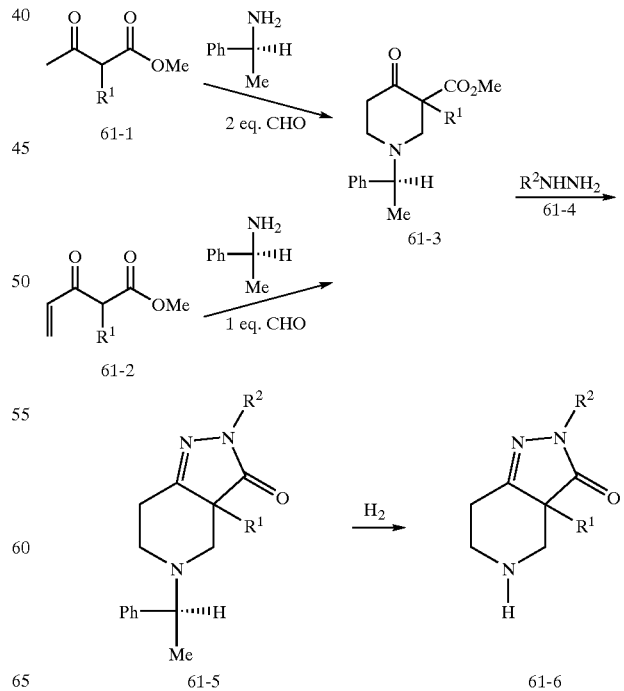

As illustrated in Scheme 61, reaction of a ketoester of formula 61-1 with a chiral amine such as alpha-methylbenzylamine with a suitable aldehyde such as formaldehyde, or reaction of a vinyl ketoester of formula 61-2 with a chiral amine such as alpha-methylbenzylamine with a suitable aldehyde such as formaldehyde, affords a compound of formula 61-3 via a double Mannich reaction. Reaction of 61-3 with a hydrazine generates a chiral compound of formula 61-5. Deprotection of the nitrogen with hydrogen and a suitable catalyst such as palladium affords compounds of formula 61-6.

SCHEME 62

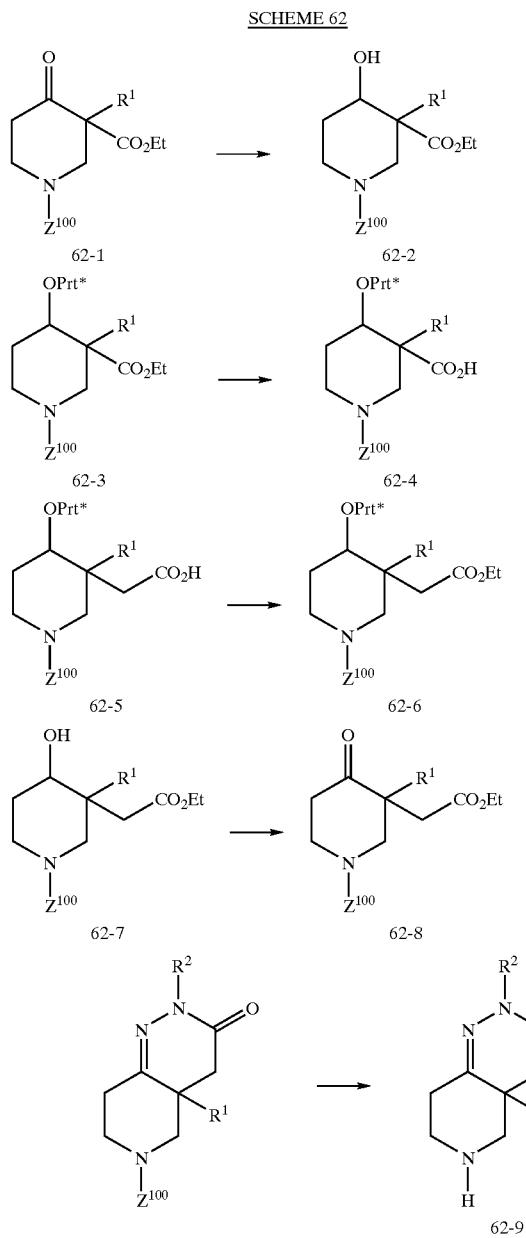

As illustrated in Scheme 62, treatment of a compound of formula 62-1 with a reducing agent such as sodium borohydride and protection of the nitrogen affords a compound if formula 62-2. Protection of the alcohol affords 62-3. Saponification of the ester affords a compound of formula 62-4. Reaction of 62-4 with thionyl chloride followed by treatment with diazomethane affords the homologated acid of formula 62-5. Esterification of 62-5 affords a compound of formula 62-6, which is O-deprotected to give 62-7. Oxidation of 62-7 affords a ketone of formula 62-8. Reaction of 62-8 with a hydrazine, followed by nitrogen deprotection affords a compound of formula 62-9.

SCHEME 63

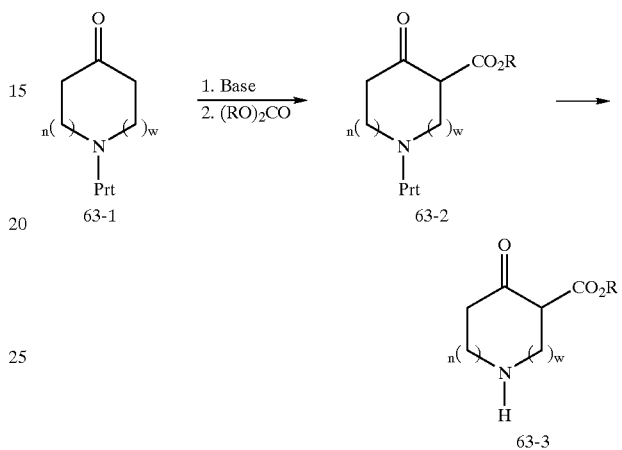

As illustrated in Scheme 63, treatment of a compound of formula 63-1 with a base such as sodium hydride in a solvent such as DMF followed by treatment with diethylcarbonate generates the ethyl ester of compound 63-2. Deprotection of the amine transforms 63-2 into 63-3.

SCHEME 64

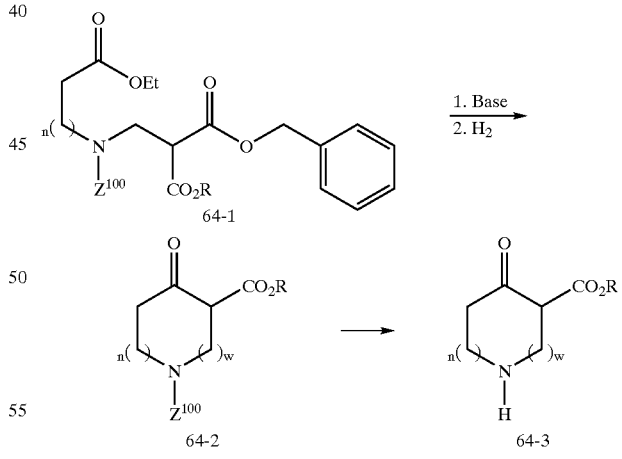

As illustrated in Scheme 64, treatment of a malonic ester of formula 64-1 with a base such as sodium hydride in a solvent such as DMF and subsequent hydrogenolysis of the benzyl group with hydrogen and a catalyst such as palladium in a suitable solvent such as methanol produces the ester of formula 64-2. Deprotection of the amine generates compounds of formula 64-3.

SCHEME 65

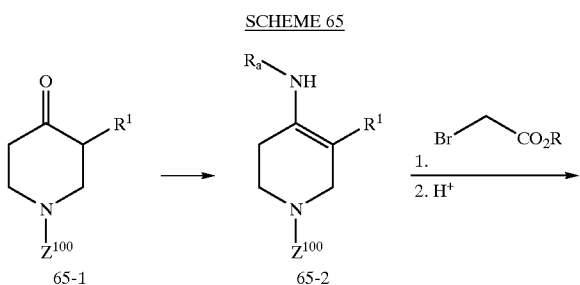

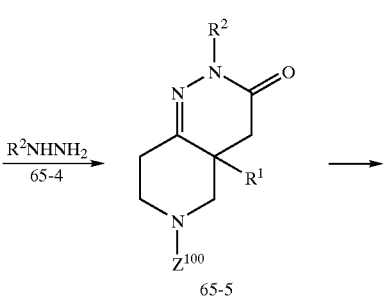

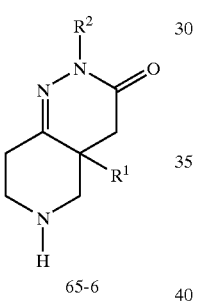

As illustrated in Scheme 65, treatment of a ketone of formula 65-1 with a secondary amine such as piperidine in a suitable solvent such as benzene with removal of water affords an enamine of formula 65-2. Alkylation of the enamine with an alpha-haloester such as ethylbromoacetate in a suitable solvent such as benzene or THF using a suitable base such as LDA or NaN(SiMe$_3$)$_2$ affords a ketoester of formula 65-3. Reaction with a hydrazine of formula 65-4 affords the compound of formula 65-5. Deprotection of the nitrogen affords compounds of formula 65-6.

SCHEME 66

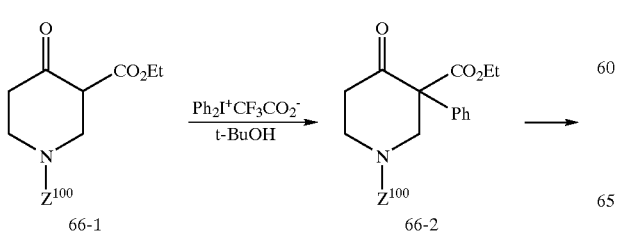

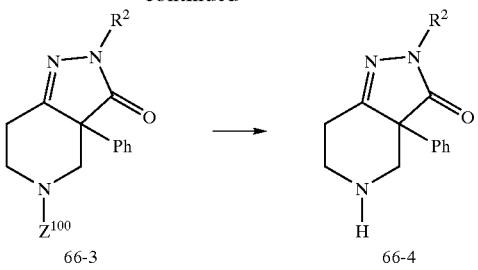

As illustrated in Scheme 66, treatment of a ketoester of formula 66-1 with an iodonium salt such as diphenyliodonium trifluoroacetate in a suitable solvent such as t-butanol generates a ketoester of formula 66-2. Reaction of 66-2 with a hydrazine generates a compound of formula 66-3. Deprotection of the nitrogen affords compounds of formula 66-4, see Synthesis, (9), 1984 p. 709 for a detailed description.

SCHEME 67

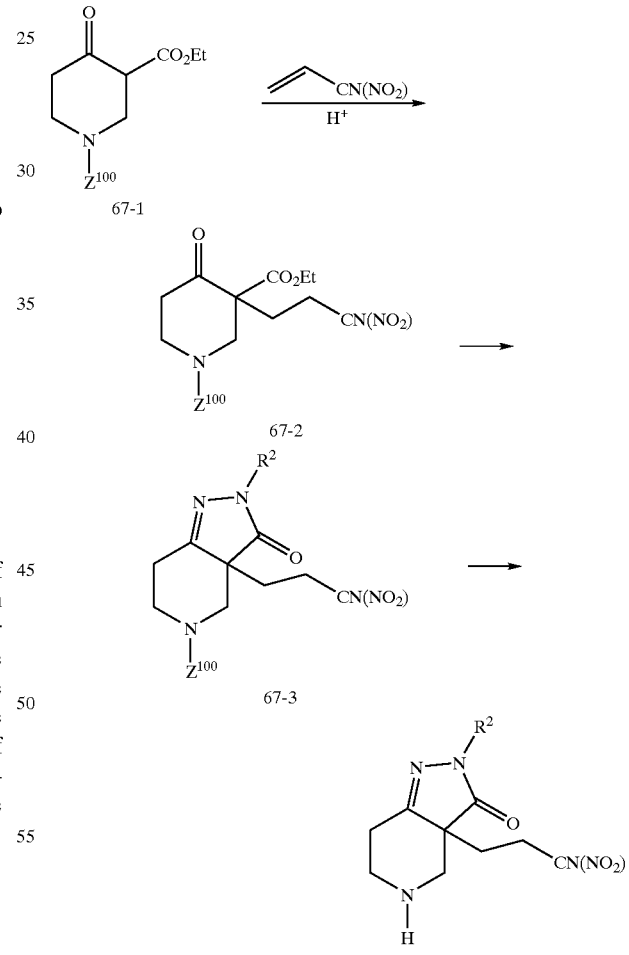

As illustrated in Scheme 67, treatment of a ketoester of formula 67-1 with an olefin such as acrylonitrile generates a ketoester of formula 67-2. Reaction of 67-2 with a hydrazine generates a compound of formula 67-3. Deprotection of the nitrogen affords compounds of formula 67-4.

SCHEME 68

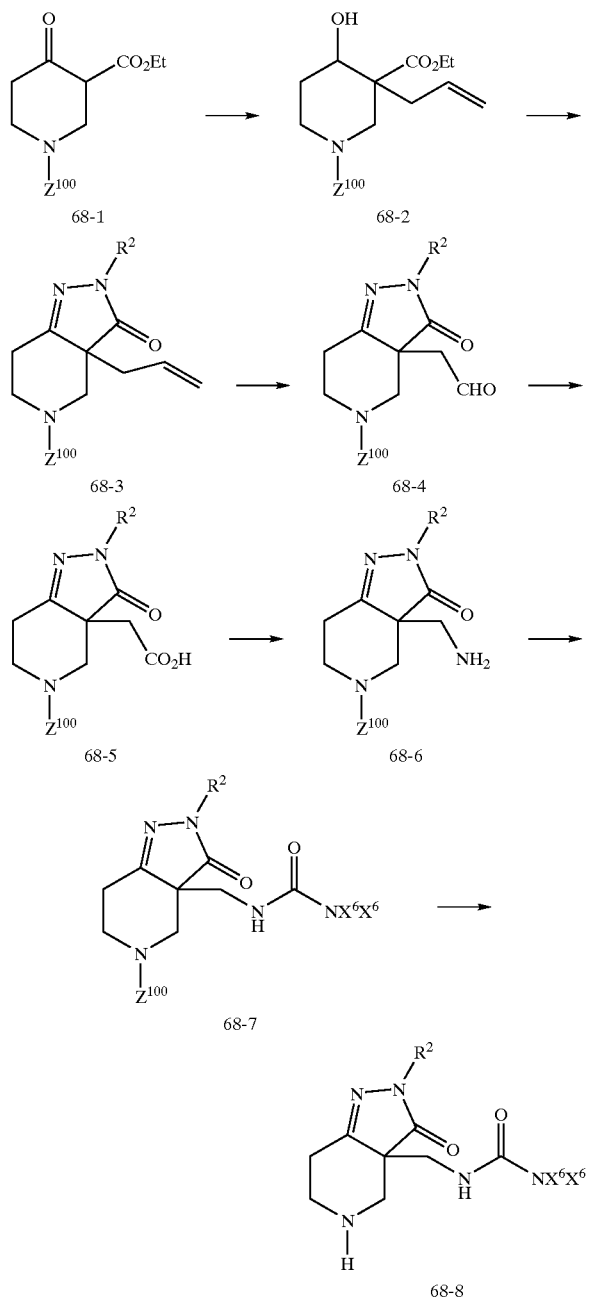

SCHEME 69

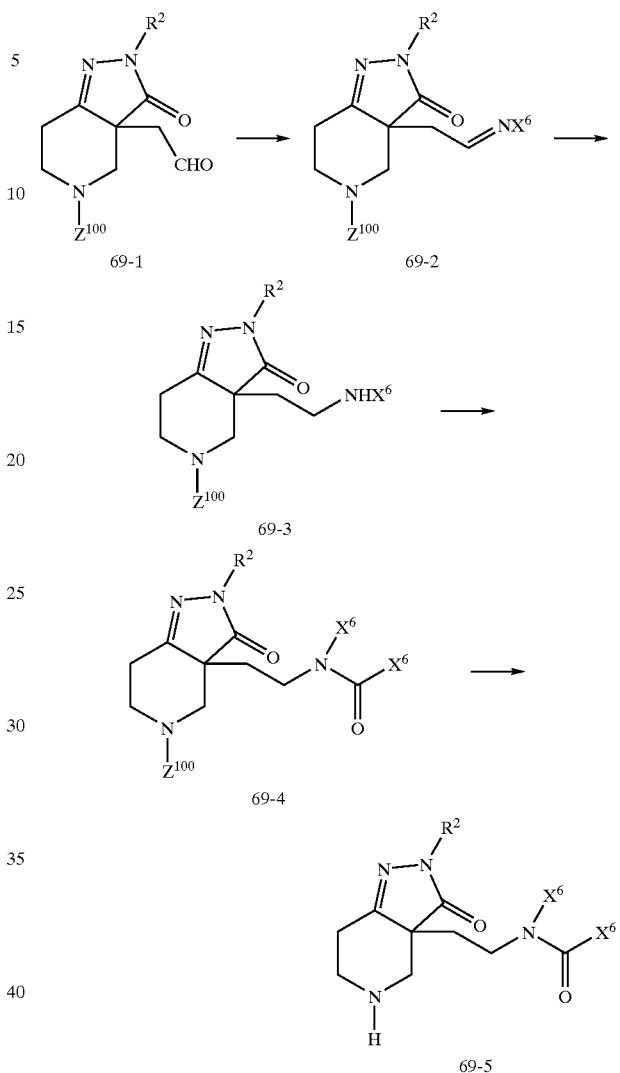

As illustrated in Scheme 68, treatment of a ketoester of formula 68-1 with allyl bromide and a suitable base such as sodium hydride in a suitable solvent such as DMF affords a ketoester of formula 68-2. Reaction of 68-2 with a hydrazine generates a compound of formula 68-3. Ozonolysis of 68-3 in a suitable solvent such as methylene chloride followed by treatment with a reducing agent such as dimethylsulfide affords an aldehyde of formula 68-4. Oxidation of 68-4 affords a carboxylic acid of formula 68-5. Curtius rearrangement of 68-5, followed by hydrolysis of the intermediate isocyanate affords a primary amine of formula 68-6. Treatment of a compound of formula 68-6 with an isocyanate or carbamate affords a urea of formula 68-7. Deprotection of the nitrogen affords compounds of formula 68-8.

As illustrated in Scheme 69, treatment of a compound of formula 69-1 with a primary amine affords an imine of formula 69-2. Reduction of a compound of formula 69-2 affords a compound of formula 69-3. Treatment of a compound of formula 69-3 with an acylating agent affords a compound of formula 69-4. Deprotection of the nitrogen affords compounds of formula 69-5.

SCHEME 70

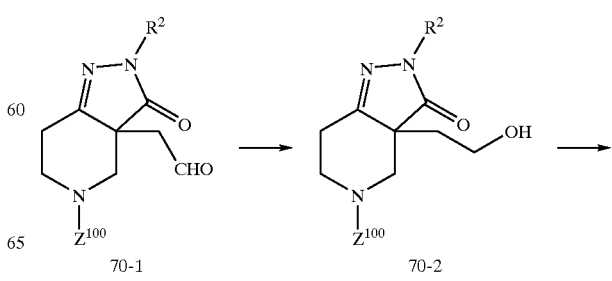

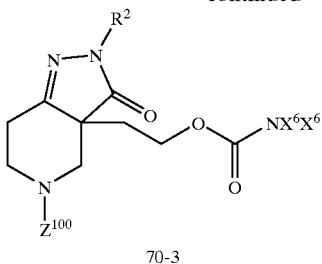

70-3

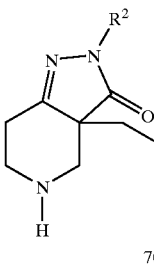

70-4

As illustrated in Scheme 70, treatment of a compound of formula 70-1 with a reducing agent such as sodium borohydride affords a compound of formula 70-2. Reaction of 70-2 with an acylating agent such as an isocyanate or carbamate affords compounds of formula 70-3. Deprotection of the nitrogen affords compounds of formula 70-4.

SCHEME 71

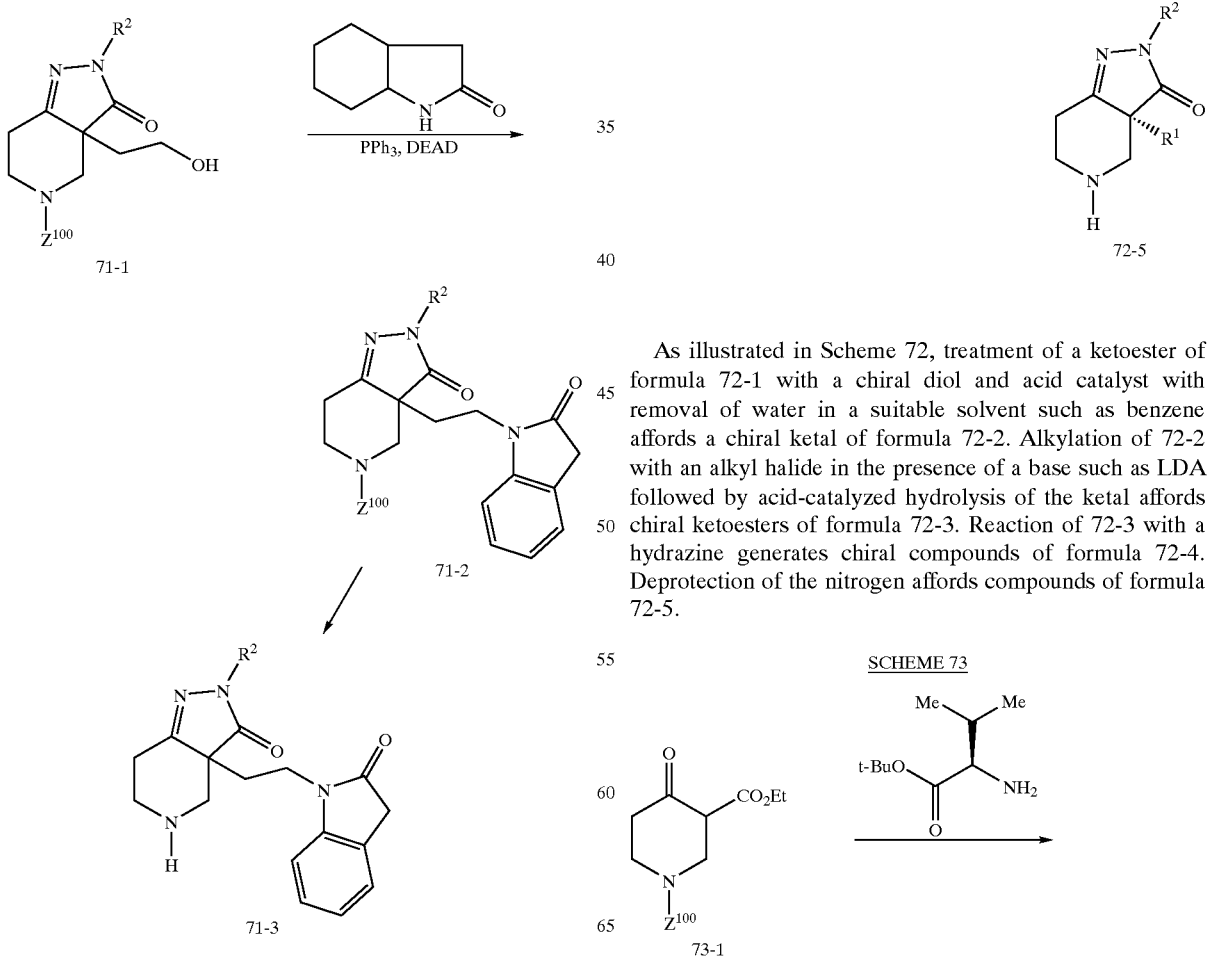

As illustrated in Scheme 71, treatment of a compound of formula 71-1 with a phosphine such as triphenyl phosphine and an azo compound such as diethylazodicarboxylate and an oxindole affords a compound of formula 71-2. Deprotection of the nitrogen affords the compound of formula 71-3.

SCHEME 72

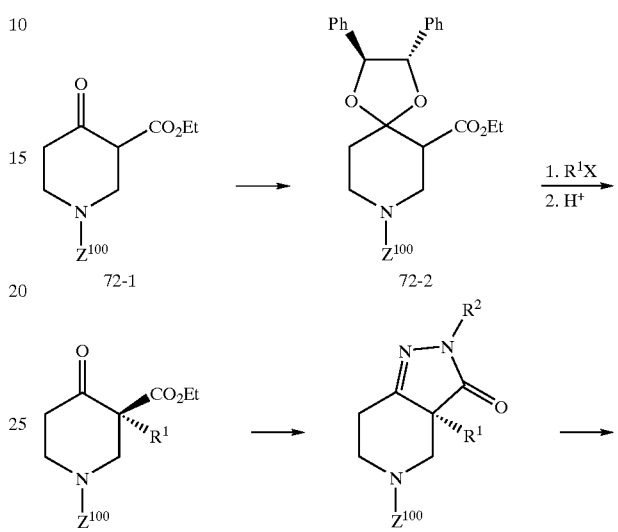

As illustrated in Scheme 72, treatment of a ketoester of formula 72-1 with a chiral diol and acid catalyst with removal of water in a suitable solvent such as benzene affords a chiral ketal of formula 72-2. Alkylation of 72-2 with an alkyl halide in the presence of a base such as LDA followed by acid-catalyzed hydrolysis of the ketal affords chiral ketoesters of formula 72-3. Reaction of 72-3 with a hydrazine generates chiral compounds of formula 72-4. Deprotection of the nitrogen affords compounds of formula 72-5.

SCHEME 73

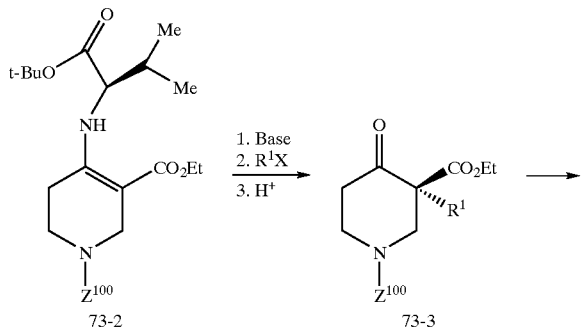

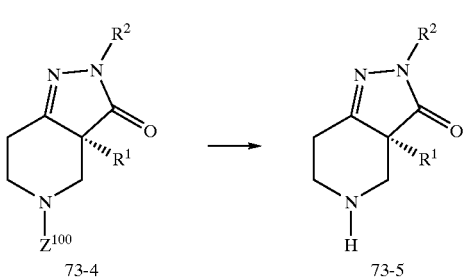

As illustrated in Scheme 73, treatment of a ketoester of formula 73-1 with a chiral amino acid ester such as valine t-butyl ester affords a chiral enamine of formula 73-2. Alkylation of 73-2 with an alkyl halide in the presence of a base such as LDA followed by acid-catalyzed hydrolysis of the enamine affords chiral ketoesters of formula 73-3. Reaction of 73-3 with a hydrazine generates chiral compounds of formula 73-4. Deprotection of the nitrogen affords compounds of formula 73-5.

SCHEME 74

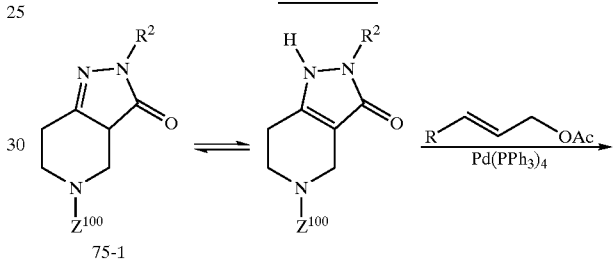

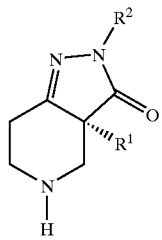

As illustrated in Scheme 21, deprotection of the nitrogen of 74-1 affords compounds of formula 74-2. Salt formation of 74-2 with a chiral acid affords a mixture of diastereomeric salts of formula 74-3. Crystallization of the diastereomeric salts affords the acid salt of chiral compounds of formula 74-4. Decomposition of the salt 74-4 with base liberates chiral compounds of formula 74-5.

SCHEME 75

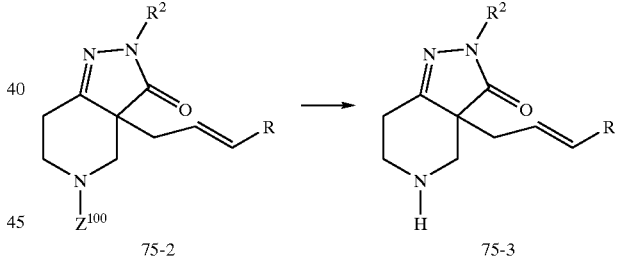

As illustrated in Scheme 75, alkylation of compounds of formula 75-1 with an allylic acetate in the presence of a suitable catalyst such as palladium tetrakis (triphenylphosphine) affords compounds of formula 75-2. Deprotection of the nitrogen affords compounds of formula 75-3, see Tetrahedron (50) p. 515, 1994 for a detailed discussion.

SCHEME 76

Me—C(=O)—CH(CO$_2$Et)—CH$_2$—CO$_2$Et 76-1

1. base, R$^1$X
2. acid
3. CH$_3$I, base
   (R$^1$ = benzyl)

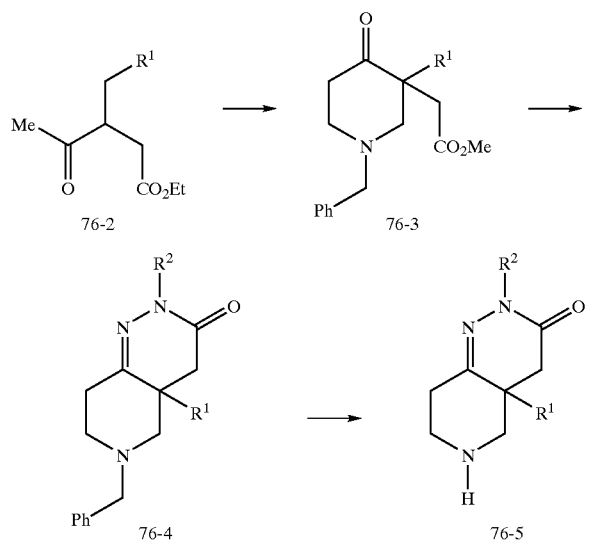

As illustrated in Scheme 76, treatment of a ketodiester of formula 76-1 with an alkyl halide in the presence of a base such as sodium hydride followed by acid-catalyzed hydrolysis and decarboxylation, followed by esterification with methyliodide and a suitable base affords a compound of formula 76-2. Reaction of a compound of formula 76-2 with a suitable aldehyde such as formaldehyde and benzylamine affords a compound of formula 76-3. Reaction of a compound of formula 76-3 with a hydrazine generates compounds of formula 76-4. Deprotection of the nitrogen affords compounds of formula 76-5.

SCHEME 77

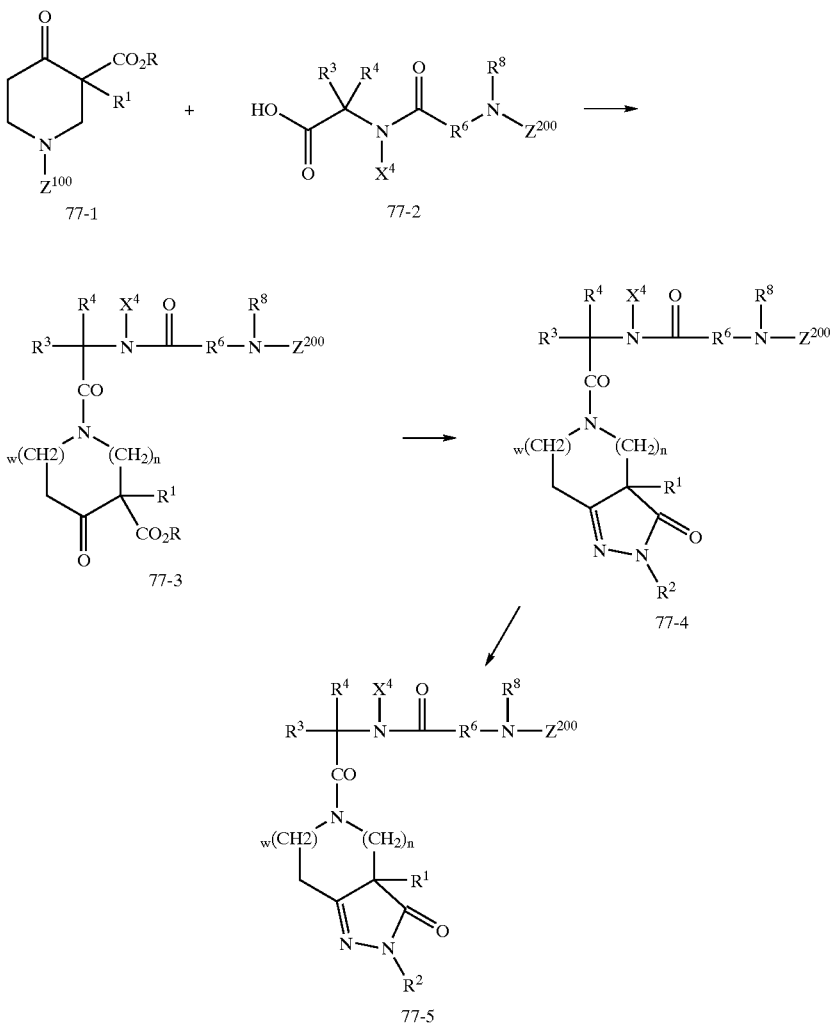

As illustrated in Scheme 77, treatment of an amine of formula 77-1 with an acid of formula 77-2 in an inert solvent such as dichloromethane or DMF by a coupling reagent such as EDC or DCC in the presence of HOBT affords compounds of formula 77-3. Reaction of compounds of formula 77-3 with a hydrazine generates compounds of formula 77-4. Deprotection of the nitrogen affords compounds of formula 77-5.

SCHEME 78

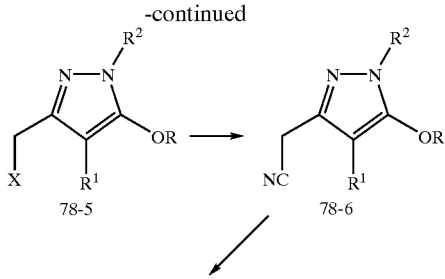

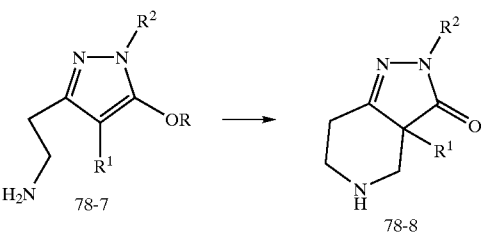

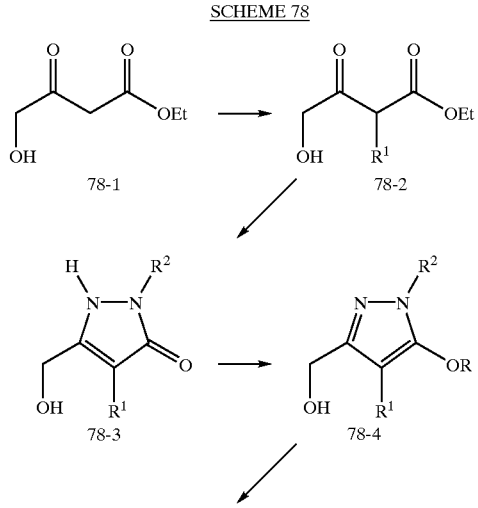

As illustrated in Scheme 78, treatment of a hydroxyacetoacetate ester of formula 78-1 with an alkyl halide in the presence of a suitable base such as sodium hydride affords compounds of formula 78-2. Reaction of 78-2 with a hydrazine generates compounds of formula 78-3. O-Alkylation of the carbonyl oxygen of 78-3 affords 78-4 which is converted to the halide 78-5. Displacement of the halide X by cyanide ion affords the nitrile 78-6. Reduction of 78-6 gives the primary amine 78-7 which is deprotected and cyclized in the presence of formaldehyde to afford 78-8.

SCHEME 79

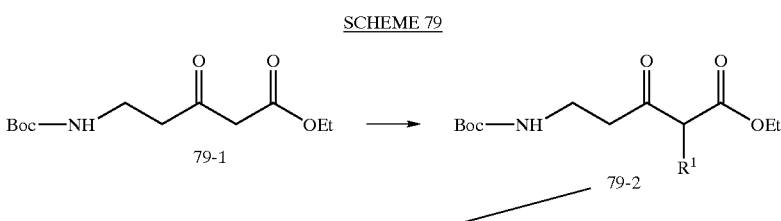

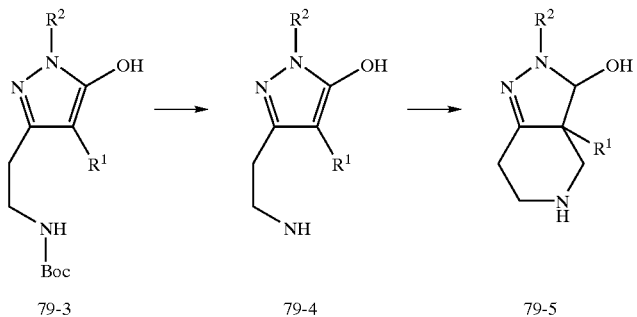

As illustrated in Scheme 79, treatment of a beta-keto-protected aminovalerate such as 79-1 with an alkyl halide in the presence of a suitable base such as sodium hydride affords compounds of formula 79-2. Reaction of compounds of formula 79-2 with a hydrazine generates compounds of formula 79-3. Deprotection of compounds of formula 99 affords primary amines of formula 79-4. Cyclization of compounds of formula 79-4 in the presence of formaldehyde affords compounds of formula 79-5.

SCHEME 80

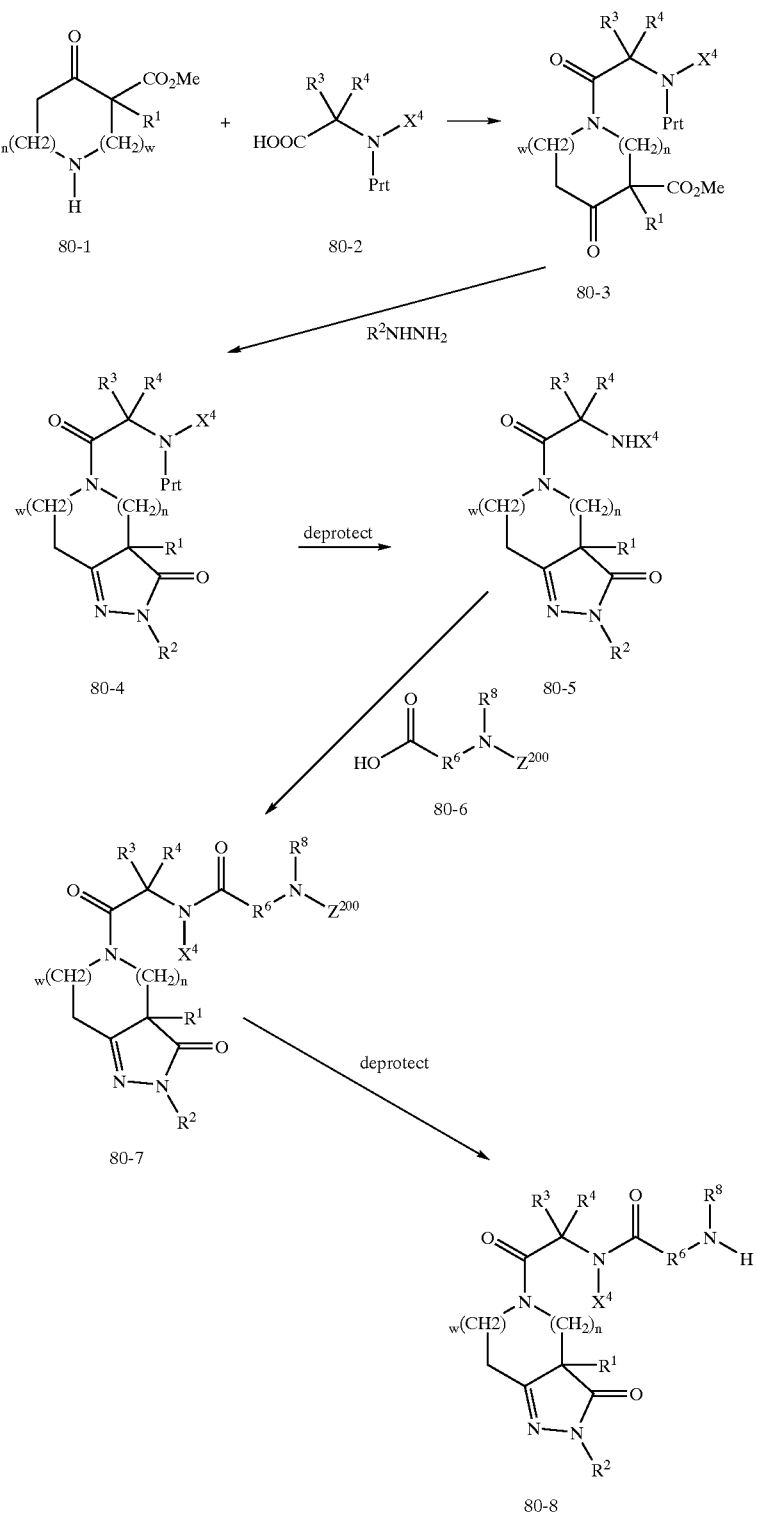

As illustrated in Scheme 80, treatment of the amine of formula 80-1 with an acid such as 80-2 in the presence of EDC and HOAT in a suitable solvent provides keto-esters of formula 80-3. The keto-ester 80-3 can be treated with a salt of hydrazine in the presence of sodium acetate in refluxing ethanol to give hydrazines of formula 80-4. Deprotection under suitable conditions gives amines of formula 80-5. Coupling of intermediates of formula 80-5 to amino acids of formula 80-6 can be effected as described above to give intermediates of formula 80-7. Deprotection of amine 80-7 affords compounds of formula 80-8.

In the above structural formulae and throughout the instant application, the following terms have the indicated meanings unless expressly stated otherwise:

The alkyl groups are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_0$-alkyl occurs in the definition, it means a single covalent bond.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined hereinabove substituted by one or more halogen atoms as defined hereinabove.

The term "halogenated cycloalkyl" is intended to include a cycloalkyl group substituted by one or more halogen atoms as defined hereinabove.

The term "aryl" is intended to include phenyl and naphthyl and aromatic 5- and 6-membered rings with 1 to 4 heteroatoms or fused 5- and/or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

The expression "prodrug" refers to compounds that are drug precursors which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the compounds of this invention include but are not limited to carboxylic acid substituents (e.g., when $R^1$ is —$(CH_2)_qC(O)OX^6$ where $X^6$ is hydrogen, or when $R^2$ or $A^1$ contains carboxylic acid) wherein the free hydrogen is replaced by ($C_1$–$C_4$)alkyl, ($C_2$–$C_{12}$)alkanoyloxymethyl, ($C_4$–$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)-alkylcarbamoyl-($C_1$–$C_2$)alkyl and piperidino-, pyrrolidino- or morpholino($C_2$–$C_3$)alkyl.

Other exemplary prodrugs release an alcohol of Formula I wherein the free hydrogen of the hydroxyl substituent (e.g., when $R^1$ contains hydroxyl) is replaced by ($C_1$–$C_6$) alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$) alkoxycarbonyloxymethyl, N-($C_1$–$C_6$)alkoxycarbonylamino-methyl, succinoyl, ($C_1$–$C_6$)alkanoyl, α-amino($C_1$–$C_4$)alkanoyl, arylacetyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O ($C_1$–$C_6$)alkyl)$_2$ or glycosyl (the radical resulting from detachment of the hydroxyl of the hemiacetal of a carbohydrate).

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as DMF at a temperature of about 0° C. to 100° C. for about 1 to about 24 hours. Alternatively, the acid is combined with the appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as DMF at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

Many protected amino acid derivatives are commercially available, where the protecting groups, Prt, Prt' or Prt", are, for example, BOC, CBZ, FMOC, benzyl or ethoxycarbonyl groups. Other protected amino acid derivatives can be prepared by literature methods well-known to one skilled in the art. Some substituted piperazines and piperidines are commercially available, and many other piperazines and 4-substituted piperidines are known in the literature. Various heterocyclic substituted piperidines and piperazines can be prepared following literature methods using derivatized heterocyclic intermediates. Alternatively, the heterocyclic rings of such compounds can be derivatized by standard means, such as coupling with CDI, hydrogenation of aromatic heterocycles, etc. as is well-known to those skilled in the art.

Certain of the above defined terms may occur more than once in the above formula and upon such occurrence each term shall be defined independently of the other.

The compounds of the instant invention all have at least one asymmetric center as noted by the asterisk in the structural Formula I. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention. In the case of the asymmetric center represented by the asterisk, it has been found that the absolute stereochemistry of the more active and thus more preferred isomer is shown in Formula IA. This preferred absolute configuration also applies to Formula I.

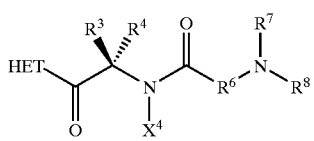

IA

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of Formula I and contacting it with about 1 equivalent of the appropriate corresponding acid of the salt which is desired. Work-up and isolation of the resulting salt is well-known to those of ordinary skill in the art.

It will be recognized that the compounds of Formula I of this invention can exist in radiolabelled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, $^{18}F$ and $^{36}Cl$, respectively. Compounds of Formula I of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability. Radiolabelled compounds of Formula I of this invention can generally be prepared of methods well known to those skilled in the art. Conveniently, such radiolabelled compounds can be prepared by carrying out the procedures disclosed in the above Schemes and/or in the Examples and Preparations below by substituting a readily available radiolabelled reagent for a non-radiolabelled reagent.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release.

The compounds of Formula I can be administered to animals, including humans, to release growth hormone in vivo. The compounds are useful for treating symptoms related to GH deficiency; stimulating pre- and post-natal growth or enhancing feed efficiency and improving carcass quality of animals raised for meat production; increasing milk production in dairy cattle; improving estrous synchronization in livestock such as swine, beef and dairy cattle; improving bone or wound healing and improving vital organ function in animals. The compounds of the present invention, by inducing endogenous GH secretion, will alter body composition and modify other GH-dependent metabolic, immunologic or developmental processes. For example, the compounds of the present invention can be given to chickens, turkeys, livestock animals (such as sheep, pigs, horses, cattle, etc.) and companion animals (e.g., dogs). These compounds may also have utility in aquaculture to accelerate growth and improve the percent lean meat. In addition, these compounds can be administered to humans in vivo as a diagnostic tool to directly determine whether the pituitary is capable of releasing growth hormone. For example, the compounds of Formula I or a pharmaceutically acceptable salt or prodrug thereof can be administered in vivo to children and serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I or a pharmaceutically acceptable salt or prodrug thereof in association with a pharmaceutically acceptable carrier. Optionally, the pharmaceutical compositions can further comprise an anabolic agent in addition to at least one of the compounds of Formula I or a pharmaceutically acceptable salt or prodrug thereof, or another compound which exhibits a different activity, e.g., an antibiotic or coccidiostat (e.g., monensin) growth promotant or an agent to treat osteoporosis or with other pharmaceutically active materials wherein the combination enhances efficacy and minimizes side effects.

Growth promoting and anabolic agents include, but are not limited to, TRH, PTH, diethylstilbesterol, estrogens, β-agonists, theophylline, anabolic steroids, enkephalins, E series prostaglandins, compounds disclosed in U.S. Pat. No. 3,239,345, the disclosure of which is hereby incorporated by reference, e.g., zeranol; compounds disclosed in U.S. Pat. No. 4,036,979, the disclosure of which is hereby incorporated by reference, e.g., sulbenox; and peptides disclosed in U.S. Pat. No. 4,411,890, the disclosure of which is hereby incorporated by reference.

The growth hormone secretagogues of this invention in combination with other growth hormone secretagogues such as the growth hormone releasing peptides GHRP-6 and GHRP-1 as described in U.S. Pat. No. 4,411,890, the disclosure of which is hereby incorporated by reference, and publications WO 89/07110, WO 89/07111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or alpha-2-adrenergic agonists such as clonidine, xylazine, detomidine and medetomidine or serotonin 5HTlD agonists such as sumitriptan or agents which inhibit somatostatin or its release such as physostigmine and pyridostigmine, are useful for increasing the endogenous levels of GH in mammals. The combination of a GH secretagogue of this invention with GRF results in synergistic increases of endogenous growth hormone.

As is well known to those skilled in the art, the known and potential uses of growth hormone are varied and multitudinous [See "Human Growth Hormone", Strobel and Thomas, Pharmacological Reviews, 46, pg. 1–34 (1994); T. Rosen et al., Horm Res, 1995; 43: pp. 93–99; M. Degerblad et al., European Journal of Endocrinology, 1995, 133: pp.180–188; J. O. Jorgensen, European Journal of Endocrinology, 1994, 130: pp. 224–228; K. C. Copeland et al., Journal of Clinical Endocrinology and Metabolism, Vol. 78 No. 5, pp. 1040–1047; J. A. Aloi et al., Journal of Clinical Endocrinology and Metabolism, Vol. 79 No. 4, pp. 943–949; F. Cordido et al., Metab. Clin. Exp., (1995), 44(6), pp. 745–748; K. M. Fairhall et al., J. Endocrinol., (1995), 145(3), pp. 417–426; R. M. Frieboes et al., Neuroendocrinology, (1995), 61(5), pp. 584–589; and M. Llovera et al., Int. J. Cancer, (1995), 61(1), pp. 138–141]. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans or companion animals especially dogs, cats, camels and horses; treating growth hormone deficient adult humans or other animals especially dogs, cats, camels and horses; preventing catabolic side effects of glucocorticoids, treating osteoporosis, stimulating the immune system, accelerating wound healing, accelerating bone fracture repair, treating growth retardation, treating congestive heart failure as disclosed in PCT publications WO 95/28173 and WO 95/28174 (an example of a method for assaying growth hormone secretagogues for efficacy in treating congestive heart failure is disclosed in R. Yang et al., Circulation, Vol. 92, No. 2, p.262, 1995), treating acute or chronic renal failure or insufficiency; treating physiological short stature including growth hormone deficient children, treating short stature associated with chronic illness, treating obesity, treating growth retardation associated with Prader-Willi syndrome and Turner's syndrome; accelerating the recovery and reducing hospitalization of burn patients or following major surgery such as gastrointestinal surgery; treating intrauterine growth retardation, skeletal dysplasia, hypercortisonism and Cushings syndrome; replacing growth hormone in stressed patients; treating osteochondrodysplasias, Noonans syndrome, sleep disorders, Alzheimer's disease, delayed wound healing, and psychosocial deprivation; treating pulmonary dysfunction and ventilator dependency; attenuating protein catabolic response after a major operation; treating malabsorption syndromes, reducing cachexia and protein loss due to chronic illness such as cancer or AIDS; accelerating weight gain and protein accretion in patients on TPN (total parenteral nutrition); treating hyperinsulinemia including nesidioblastosis; adjuvant treatment for ovulation induction and to prevent and treat gastric and duodenal ulcers; stimulating thymic development and preventing age-related decline of thymic function; adjunctive therapy for patients on chronic hemodialysis; treating immunosuppressed patients and enhancing antibody response following vaccination; improving muscle strength, increasing muscle mass, mobility, maintenance of skin thickness, metabolic homeostasis, renal homeostasis in the frail elderly; stimulating osteoblasts, bone remodeling, and cartilage growth; treating neurological diseases such as peripheral and drug induced neuropathy, Guillian-Barre Syndrome, amyotrophic lateral sclerosis, multiple sclerosis, cerebrovascular accidents and demyelinating diseases; and stimulating wool growth in sheep.

Uses of GH in farm animals raised for meat production such as chickens, turkeys, sheep, pigs and cattle include stimulation of pre- and post- natal growth, enhanced feed efficiency in animals raised for meat production, improved carcass quality (increased muscle to fat ratio) (Campbell, R. G. et al., (1989), J. Anim. Sci. 67, 1265; Dave, D. J., Bane, D. P., (1990), The Compendium Food Annual, Vol. 12(1), 117; Holden, P. J., (1990), Agri-Practice, 11(3), 25; Claus, R., Weiber, U., (1994), Livestock Production Science, 37, 245; Roeder, R. et al., (1994), Growth Regulation, 4, 101); increased milk production in dairy cattle (McBride, B. W. et al., (1988), Research and Development in Agriculture 5(1), 1; McDowell, G. H. et al., (1988), Aust. J. Biol. Sci., 41, 279); improved body composition; modification of other GH-dependent metabolic (Claus, R. and Weiber, U., (1994), Livestock Production Science, 37, 245) and immunologic functions such as enhancing antibody response following vaccination or improved developmental processes; and may have utility in aquaculture to accelerate growth and improve the protein-to-fat ratio in fish.

Preferred uses in companion animals include stimulating endogenous growth hormone release in companion animals such as dogs, cats and horses; treating disorders of aging (Detenbeck, L. C., Jowsey, J., Clinical Orthopedics and Related Research, July-August 1969, No. 65, pp. 76–80); stimulating thymic development and preventing age-related decline of thymic function (Goff, B. L. et al., Clinical and Experimental Immunology, 1987, 68:3, pp. 580–587; Morrison, W. B. et al., Am. J. Vet. Res., January 1990, 51:1, pp. 65–70; Roth, J. A. et al., Am. J. Vet. Res., 1984, Vol. 45, pp. 1151–1155); preventing age-related decline of thymic function; preventing age-related decline in cognition; accelerating wound healing (Jacks, T. et al., Vet. Surg. 1996, 25, (5), 430); accelerating bone fracture repair (Pandey, S. K., Udupa, K. N., Indian J. Vet. Surg. 1 (2): 73–78, July 1980); stimulating osteoblasts, bone remodelling and cartilage growth (Harris, W. H. et al., Calc. Tiss. Res., 10, 1972, pp. 1–13; Heaney, R. P. et al., Calc. Tiss. Res. 10, 1972, pp. 14–22; Mankin. H. J. et al., J. of Bone and Joint Surgery, Vol. 60-A, #8, December 1978, pp. 1071–1075); attenuating protein catabolic response, after major surgery, accelerating recovery from burn injuries and major surgeries such as gastrointestinal surgery; stimulating the immune system and enhancing antibody response following vaccination; treating congestive heart failure, treating acute or chronic renal failure or insufficiency, treating obesity; treating growth retardation, skeletal dysplasia and osteochondrodysplasias; preventing catabolic side effects of glucocorticoids; treating Cushing's syndrome; treating malabsorption syndromes, reducing cachexia and protein loss due to chronic illness such as cancer; accelerating weight gain and protein accretion in animals receiving total parenteral nutrition; providing adjuvant treatment for ovulation induction and to prevent gastrointestinal ulcers; improving muscle mass, strength and mobility; maintenance of skin thickness, and improving vital organ function and metabolic homeostasis.

The growth hormone secretagogues of this invention, compounds of Formula I, or a pharmaceutically acceptable salt or prodrug thereof in combination with an alpha-2 adrenergic agonist are useful in promoting GH secretion in humans and other animals (See Cella, S. G. et al., Acta Endocrinologica (Copenh.) 1989, 121, pp. 177–184). As such, a combination of a compound of Formula I or a pharmaceutically acceptable salt or prodrug thereof and an alpha-2 adrenergic agonist is useful in the treatment or prevention of frailty associated with aging, congestive heart failure and obesity which comprises administering to a human or another animal, especially dogs, cats and horses, in need of such treatment a combination of an alpha-2 adrenergic agonist and a compound of Formula I or a pharmaceutically acceptable salt or prodrug thereof, defined above. Preferred alpha-2 adrenergic agonists include clonidine, which is disclosed in U.S. Pat. No. 3,202,660 the disclosure of which is hereby incorporated by reference, xylazine, which is disclosed in U.S. Pat. No. 3,235,550 the disclosure of which is hereby incorporated by reference and medetomidine, which is disclosed in U.S. Pat. No. 4,544,664 the disclosure of which is hereby incorporated by reference. In another aspect, this invention provides methods for accelerating bone fracture repair and wound healing, attenuating protein catabolic response after a major operation, and reducing cachexia and protein loss due to chronic illness, which comprise administering to a human or another animal, especially dogs, cats and horses in need of such treatment a combination of an alpha-2 adrenergic agonist such as clonidine, xylazine or medetomidine and a compound of Formula I or a pharmaceutically acceptable salt or prodrug thereof. It has been shown that alpha-2 adrenergic agonists cause release of endogenous growth hormone in human and canine subjects (Cella et al., Life Sciences (1984), 34:447–454; Hampshire J, Altszuler N., American Journal of Veterinary Research (1981), 42:6, 1073–1076; Valcavi et al., Clinical Endocrinology (1988), 29:309–316; Morrison et al., American Journal of Veterinary Research (1990), 51:1, 65–70;), and that the co-administration of an alpha-2 adrenergic agonist with growth hormone-releasing factor restores defective growth hormone secretion in aged dogs (Arce et al., Brain Research (1990), 537:359–362; Cella et. al., Neuroendocrinology (1993), 57:432–438).

This invention also relates to a method of treating insulin resistant conditions such as Non-insulin Dependent Diabetes Mellitus (NIDDM) and reduced glycemic control associated with obesity and aging in a mammal in need thereof which comprises administering to said mammal an effective amount of a compound of the Formula I or a pharmaceutically acceptable salt or prodrug thereof.

This invention is directed to the use of growth hormone secretagogues specifically growth hormone releasing peptides (GHRP) or GHRP mimetics of Formula I or a pharmaceutically acceptable salt or prodrug thereof to improve glycemic control. Agents that increase growth hormone (GH) levels would not be expected to have this effect since it is widely recognized that GH is diabetogenic in animals and in humans. In acromegalics, glucose utilization and suppression of hepatic glucose production are impaired (see Hansen, I., et al., Am J Physiol, 250:E269 (1986)). In this disease of GH excess, impaired glucose handling and hyperinsulinemia have been reversed by pituitary surgery or chemotherapy which reduced GH levels (see Levin S. R., et al., Am J Med, 57:526 (1974), Feek, C. M., et al., J Clin Endocrinol 22:532 (1981)). Furthermore, administration of GH to older subjects caused hyperglycemia, glucose intolerance and hyperinsulinemia in numerous studies (see Aloia, J. F., et al., J Clin Endocrinol Metab, 43:992 (1976); Binnerts et al., J Clin Endocrinol Metab, 67:1312 (1988); Marcus, R., et al., J Clin Endocrinol Metab, 70:519 (1990)).

Therefore, GH therapy is contra-indicated for individuals with diabetes or those at risk for diabetes.

It will be known to those skilled in the art that there are numerous compounds now being used in an effort to treat the diseases or therapeutic indications enumerated above. Combinations of these therapeutic agents, some of which have also been mentioned above, with growth promotant, exhibit anabolic and desirable properties of these various therapeutic agents. In these combinations, the therapeutic agents and the growth hormone secretagogues of this invention may be independently and sequentially administered in any order or co-administered in dose ranges from one one-hundredth to one times the dose levels which are effective when these compounds and secretagogues are used singly. Combined therapy to inhibit bone resorption, prevent osteoporosis, reduce skeletal fracture, enhance the healing of bone fractures, stimulate bone formation and increase bone mineral density can be effectuated by combinations of bisphosphonates and the growth hormone secretagogues of this invention. See PCT publication WO 95/11029 for a discussion of combination therapy using bisphosphonates and GH secretagogues. The use of bisphosphonates for these utilities has been reviewed, for example, by Hamdy, N. A. T., Role of Bisphosphonates in Metabolic Bone Diseases, Trends in Endocrinol. Metab., 1993, 4, pages 19–25. Bisphosphonates with these utilities include but are not limited to alendronate, tiludronate, dimethyl-APD, risedronate, etidronate, YM-175, clodronate, pamidronate, and BM-210995 (ibandronate). According to their potency, oral daily dosage levels of the bisphosphonate of between 0.1 mg/kg and 5 g/kg of body weight and daily dosage levels of the growth hormone secretagogues of this invention of between 0.01 mg/kg to 20 mg/kg of body weight are administered to patients to obtain effective treatment of osteoporosis.

The compounds of this invention may be combined with a mammalian selective estrogen receptor modulator (SERM). Any SERM may be used as the second compound of this invention. The term selective estrogen receptor modulator includes both estrogen agonist and estrogen antagonists and refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods (see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1): 50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other SERMs will be known to those skilled in the art. A preferred SERM is droloxifene: (phenol, 3-[1-[4[2-(dimethylamino)ethoxy]-phenyl]-2-phenyl-1-butenyl]-, (E)-) and associated compounds which are disclosed in U.S. Pat. No. 5,047,431, the disclosure of which is hereby incorporated by reference.

Another preferred SERM is tamoxifen: (ethanamine,2-[-4-(1,2-diphenyl-1-butenyl)phenoxy]-N,N-dimethyl, (Z)-2, 2-hydroxy-1,2,3-propanetri-carboxylate (1:1)) and associated compounds which are disclosed in U.S. Pat. No. 4,536,516, the disclosure of which is hereby incorporated by reference. Another related compound is 4-hydroxy tamoxifen which is disclosed in U.S. Pat. No. 4,623,660, the disclosure of which is hereby incorporated by reference.

Another preferred SERM is raloxifene: (methanone, [6-hydroxy-2-(4-hydroxyphenyl)benzo[b]thien-3-yl][4-[2-(1-piperidinyl)ethoxy]phenyl]-,hydrochloride) and associated compounds which are disclosed in U.S. Pat. No. 4,418,068, the disclosure of which is hereby incorporated by reference.

Another preferred SERM is idoxifene: Pyrrolidine, 1-[-[4-[[1-(4-iodophenyl)-2-phenyl-1-Butenyl]phenoxy]ethyl] and associated compounds which are disclosed in U.S. Pat. No. 4,839,155, the disclosure of which is hereby incorporated by reference.

Other preferred SERMs include compounds as described in commonly assigned U.S. Pat. No. 5,552,412 the disclosure of which is hereby incorporated by reference. Especially preferred compounds which are described therein are:

cis-6-(4-fluoro-phenyl)-5-[4-(2-piperidin-1-yl-ethoxy)-phenyl]-5,6,7,8-tetrahydro-naphthalen-2-ol;

(−)-cis-6-phenyl-5-[4-(2-pyrrolidin-1-yl-ethoxy)-phenyl]-5,6,7,8-tetrahydro-naphthalen-2-ol;

cis-6-phenyl-5-[4-(2-pyrrolidin-1-yl-ethoxy)-phenyl]-5,6,7,8-tetrahydro-naphthalen-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalen-2-ol; and 1-(4'-pyrrolidinolethoxyphenyl)-2-phenyl-6-hydroxy-1,2,3,4-tetrahydroisoquinoline.

Other SERMs are described in U.S. Pat. No. 4,133,814, the disclosure of which is hereby incorporated by reference. U.S. Pat. No. 4,133,814 discloses derivatives of 2-phenyl-3-aroyl-benzothiophene and 2-phenyl-3-aroylbenzothiophene-1-oxide.

The following paragraphs provide preferred dosage ranges for various anti-resorptive agents.

The amount of the anti-resorptive agent to be used is determined by its activity as a bone loss inhibiting agent. This activity is determined by means of an individual compound's pharmacokinetics and its minimal maximal effective dose in inhibition of bone loss using a protocol such as those referenced above.

In general an effective dosage for the activities of this invention, for example the treatment of osteoporosis, for the SERMs (when used in combination with a compound of Formula I or a pharmaceutically acceptable salt or prodrug thereof of this invention) is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for cis-6-(4-fluoro-phenyl)-5-[4-(2-piperidin-1-yl-ethoxy)-phenyl]-5,6,7,8-tetrahydro-naphthalen-2-ol;

(−)-cis-6-phenyl-5-[4-(2-pyrrolidin-1-yl-ethoxy)-phenyl]-5,6,7,8-tetrahydro-naphthalen-2-ol;

cis-6-phenyl-5-[4-(2-pyrrolidin-1-yl-ethoxy)-phenyl]-5,6,7,8-tetrahydro-naphthalen-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalen-2-ol; or 1-(4'-pyrrolidinolethoxyphenyl)-2-phenyl-6-hydroxy-1,2,3,4-tetrahydroisoquinoline is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

Assay for Stimulation of GH Release from Rat Pituicytes

Compounds that have the ability to stimulate GH secretion from cultured rat pituitary cells are identified using the following protocol. This test is also useful for comparison to standards to determine dosage levels. Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P-6141, St. Louis, Mo.) in HBSS. The tissue-enzyme mixture is stirred in a spinner flask at 30 rpm in a 5% $CO_2$ atmosphere at about 37° C. for about 30 min., with manual trituration after about 15 min. and about 30 min. using a 10-mL pipet. This mixture is centrifuged at 200×g for about 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate, Gibco, Grand Island, N.Y.) and counted. Cells are plated at 6.0–6.5×10$^4$ cells per cm$^2$ in 48-well Costar™ (Cambridge, Mass.) dishes and cultured for 3–4 days in culture medium.

Just prior to GH secretion assay, culture wells are rinsed twice with release medium, then equilibrated for about 30 minutes in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the release medium, which is centrifuged at 2000×g for about 15 minutes to remove cellular material. Rat growth hormone concentrations in the supernatants are determined by a standard radioimmunoassay protocol described below.

Measurement of Rat Growth Hormone

Rat growth hormone concentrations were determined by double antibody radioimmunoassay using a rat growth hormone reference preparation (NIDDK-rGH-RP-2) and rat growth hormone antiserum raised in monkey (NIDDK-anti-rGH-S-5) obtained from Dr. A. Parlow (Harbor-UCLA Medical Center, Torrence, Calif.). Additional rat growth hormone (1.5U/mg, #G2414, Scripps Labs, San Diego, Calif.) is iodinated to a specific activity of approximately 30 $\mu$Ci/$\mu$g by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g rat growth hormone per tube above basal levels.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad libitum. The experiments are conducted in accordance with the NIH Guide for the Care and Use of Laboratory Animals.

On the day of the experiment, test compounds are dissolved in vehicle containing 1% ethanol, 1 mM acetic acid and 0.1% bovine serum albumin in saline. Each test is conducted in three rats. Rats are weighed and anesthetized via intraperitoneal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 $\mu$l). Fifteen minutes after anesthetic administration, test compound is delivered by intravenous injection into the tail vein, with a total injection volume of 1 mL/kg body weight. Additional blood samples are taken from the tail at 5, 10 and 15 minutes after compound administration. Blood samples are kept on ice until serum separation by centrifugation (1430×g for 10 minutes at 10° C.). Serum is stored at −80° C. until serum growth hormone determination by radioimmunoassay as described above.

Assessment of Exogenously-Stimulated Growth Hormone Release in the Dog after Oral Administration On the day of dosing, the test compound is weighed out for the appropriate dose and dissolved in water. Doses are delivered at a volume of 0.5–3 mL/kg by gavage to 2–4 dogs for each dosing regimen. Blood samples (5 mL) are collected from the jugular vein by direct vena puncture pre-dose and at 0.17, 0.33, 0.5, 0.75, 1, 2, 4, 6, 8 and 24 hours post dose using 5 mL vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 $\mu$Ci/$\mu$g. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g canine GH/tube.

Assessment of Canine Growth Hormone and Insulin-Like Growth Factor-1 Levels in the Dog After Chronic Oral Administration The dogs receive test compound daily for either 7 or 14 days. Each day of dosing, the test compound is weighed out for the appropriate dose and dissolved in water. Doses are delivered at a volume of 0.5–3 ml/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.754, 1, 2, 3, 6, 8, 12 and 24 hours post administration on days 0, 7 and 14 using 5 ml vacutainers containing lithium heparin. In addition, blood is drawn pre-dose and 8 hours on days 3 and 10. The prepared plasma is stored at −20° C. until analysis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules and for companion animals the solid dosage forms include an admixture with food and chewable forms. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art..

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range in humans is 0.01 to 5.0 mg/kg of body weight daily which can be administered as a single dose or divided into multiple doses.

A preferred dosage range in animals other than humans is 0.01 to 10.0 mg/kg of body weight daily which can be administered as a single dose or divided into multiple doses. A more preferred dosage range in animals other than humans is 0.1 to 5 mg/kg of body weight daily which can be administered as a single dose or divided into multiple doses.

Throughout this specification the following abbreviations are used with the following meanings:

| | |
|---|---|
| BOC | t-Butyloxycarbonyl |
| Bz | Benzyl |
| BOP | Benzotriazol-1-yloxy tris(dimethylamino) phosphonium hexafluorophosphate |
| CBZ | Benzyloxycarbonyl |
| CDI | N,N'-Carbonyldiimidazole |
| DCC | Dicyclohexylcarbodiimide |
| DEC | 1,2-Diethylaminoethyl chloride hydrochloride |
| DMAP | 4-Dimethylaminopyridine |
| DMF | Dimehtylformamide |
| DPPA | Diphenylphosphoryl azide |
| EDC | 1(3-Dimethylaminopropyl)-3-ethylcarbodiimide hydrochloride |
| EtOAc | Ethyl acetate |
| Hex | Hexane |
| HOAT | 1-Hydroxy-7-azabenzotrizole |
| HOBT | Hydroxybenzotriazole hydrate |
| HPLC | High pressure liquid chromatography |
| Hz | Hertz |
| KHMDS | Potassium Bis(trimethylsilyl)amide |
| LHMDS | Lithium Bis(trimethylsilyl)amide |
| MHz | Megahertz |
| MS | Mass Spectrum |
| NaHMDS | Sodium Bis(trimethylsilyl)amide |
| NMR | Nuclear Magnetic Resonance |
| PPAA | 1-Propanephosphonic acid cyclic anhydride |
| PTH | Parathyroid hormone |
| TFA | Trifluoroacetic acid |
| THF | Tetrahydrofuran |
| TLC | Thin layer chromatography |
| TRH | Thyrotropin releasing hormone |

EXAMPLE ONE

3-Aminomethyl-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-benzamide, hydrochloride

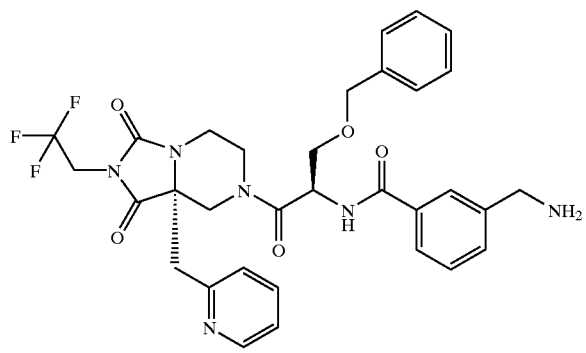

A. 2-Pyridin-2-ylmethyl-piperazine-1,2,4-tricarboxylic acid 1-benzyl ester 4-tert-butyl ester 2-methyl ester A stirred solution of piperazine-1,2,4-tricarboxylic acid 1-benzyl ester 4-tert-butyl ester 2-methyl ester (200 g, 529 mol), prepared as described by Bigge et al. (Tetrahedron Let. 1989, 30, 5193), in tetrahydrofuran (200 mL) and DMF (1.5 L) was cooled to −78° C., and a 0.5 M solution of potassium bis(trimethylsilyl)amide in THF (1.27 L) was added. After the above solution had stirred for about one hour, the free base of 2-picolyl chloride was generated by extracting the corresponding hydrochloride salt (217 g, 1.32 mol) from saturated sodium bicarbonate solution with methylene chloride. The combined organic extracts were dried ($MgSO_4$), concentrated, immediately dissolved in DMF (100 mL), and then added dropwise to the enolate containing solution. The reaction was stirred for 4 hours at −78° C., then slowly warmed to room temperature and stirred overnight. The toluene and THF were removed under reduced pressure. The residue was extracted from water (1.5 L) with ethyl acetate (3×1 L), the combined extracts were then washed with water (1.5 L), dried ($MgSO_4$) and then concentrated in vacuo to give 240 g of crude product of part A which carried on to the next step: +APcI MS $(M+H)^+470$, (M−'Bu+H) 436; $^1H$ NMR=400 MHz (methanol-$d_4$) δ: 8.4 (arom, m, 1H), 7.65–7.2 (arom, m, 7H), 6.94 (arom, m, 1H), 5.18 (CbzNCHH, m, 1H), 5.05 (CbzNCHH, m, 1H), 2.54 (m, 1H), 1.41 (Boc, s, 9H).

B. 3-Pyridin-2-ylmethyl-piperazine-1,3-dicarboxylic acid 1-tert-butyl ester 3-methyl ester The crude product of part A (240 g) in methanol (1 L), and 10% palladium on carbon (10 g, added in 100 mL water) were combined and hydrogenated at about 40–50 psi hydrogen on a Parr® shaker for a about 2 days. The mixture was then filtered though a bed of diatomaceous earth. The diatomaceous earth was washed with ethanol, and the filtrate was concentrated in vacuo to give the de-benzylated amine. Two of the above alkylation/reductions were combined and purified by silica gel chromatography using 1:1 ethyl acetate/hexanes to ethyl acetate to 1:9 methanol/ethyl acetate as eluent and yielded the title compound of part B (217 g, 61%): +APcI $(M+1)^+336$; $^1H$ NMR=400 MHz (methanol-$d_4$) δ: 8.45 (arom, d, 1H), 7.72 (arom, t, 1H), 7.26–7.11 (arom, m, 2H), 4.38 (br s, 1H), 3.57 (MeO, s, 3H), 1.41 (Boc, s, 9H).

C. 1,3-Dioxo-8a-pyridin-2-ylmethyl-2-(2,2,2-trifluoro-ethyl)-hexahydro-imidazo[1,5-a]pyrazine-7-carboxylic acid tert-butyl ester To a suspension of N,N'-carbonyldiimidazole (69 g, 426 mmol) and 2,2,2-trifluoroethylamine hydrochloride (71 g, 527 mmol) in dichloromethane (500 mL) was added triethylamine (76 mL, 544 mmol) at about 0° C. dropwise. The reaction was then warmed to room temperature and stirred at room temperature for about 30 minutes. A solution the title compound of part B (57 g, 170 mmol) in dichloromethane (100 mL) was then added, and the mixture was heated to about 40° C. and then stirred for approximately 2 days. The reaction was quenched with saturated sodium bicarbonate solution, and the mixture was then extracted twice with dichloromethane. The combined organic layers were extracted twice with water, dried over anhydrous magnesium sulfate, filtered and concentrated in vacuo to give crude product. Purification by silica gel chromatography using 1:9 to 1:2 to 1:1 ethyl acetate/hexanes as eluent afforded the title compound of part C (68.3 g, 94%) as an amorphous solid: +APcI MS $(M+H)^+429$; $^1H$ NMR=400 MHz ($CDCL_3$) δ: 8.4 (arom, d, 1H), 7.54 (arom, t, 1H), 7.12 (arom, t, 1H), 7.04 (arom, d, 1H), 4.16–4.00 ($CF_3CH_2$, m, 2H), 3.41 (PyrC$H_2$, Ab$_q$, 2H), 1.50 (Boc, s, 9H).

D. 8a-Pyridin-2-ylmethyl-2-(2,2,2-trifluoro-ethyl)-tetrahydro-imidazo[1,5-a]pyrazine-1,3-dione To a solution of the title compound of part C (22.8 g, 53.2 mmol) in ethanol (1 L) at 0° C. was added concentrated aqueous hydrochloric acid, dropwise. After stirring around 4 hours, the mixture was concentrated under reduced pressure, and then concentrated three more times from ethanol (0.5 L). The residue was extracted from saturated aqueous NaHCO$_3$ with 3:1 chloroform/isopropanol (4×), the combined organic layers were dried over anhydrous magnesium sulfate, filtered and concentrated in vacuo to give the title compound of part D (206 mg, 90%): +APcI MS (M+H)$^+$329; $^1$H NMR=400 MHz (CDCL$_3$) δ8.42 (arom, ddd, 1H), 7.55 (arom, td, 1H), 7.37–7.07 (arom, m, 2H); 4.15–3.98 (CF$_3$CH$_2$, m, 2H), 3.87 (NCHHCH$_2$, m, 1H), 3.79 (CCHHNH, d, 1H), 3.40 (CCHHNH, d, 1H), 3.25 (PyrCHH, d, 1H), 3.13 (NCHHCH$_2$, ddd, 1H), 3.02 (NCH$_2$CHHNH, dd, 1H), 2.74, (PyrCHH, d, 1H), 2.66 (NCH$_2$CHHNH, td, 1H).

E. 1,3-Dioxo-8a(S)-pyridin-2-ylmethyl-2-(2,2,2-trifluoro-ethyl)-hexahydro-imidazo[1,5-a]pyrazine-7-carboxylic acid tert-butyl ester, D-tartrate salt To a solution of the title compound of part D (206 g, 628 mmol) in 10:1 acetone/water (4.5 L) was added D-tartaric acid (94.2 g, 628 mmol). After several minutes a colorless precipitate formed. After stirring for about 2 days the solid was collected by filtration (144 g, 80% ee). The precipitate was then placed in acetone (2 L) and was heated for about 15 hours at about 56° C. The mixture was cooled and the title compound of part E was collected by filtration (117 g, 78% yield). HPLC analysis of the free base of the title compound of part E, generated by extracting the tartrate salt from aqueous sodium bicarbonate with 3:1 chloroform/isopropanol, indicated that the material had an enantiomeric excess of 94%: +APcI MS (M+H)$^+$329.

HPLC analysis was performed on an Hewlett-Packard 1050 system with a 1050 DAD, autosampler and solvent delivery system. Data is imported into a HP Vectra XM series 3 running HP Chemstation ver A.4.02. When possible, samples were dissolved in the mobile phase at 1 mg/ml. A Chiracel AD 4.6×250 mm column was employed with the following solvents: A=hexane+0.1% diethylamine (v/v); C=isopropanol+0.1% diethylamine (v/v). An isocratic elution was employed using 85% A and 15% C with a flow rate of 1 ml/min, detecting at uv, 254 nm. The desired enantiomer eluted at 11.8 min., while the undesired enantiomer eluted at 15.6 min.

F. 3-(tert-Butoxycarbonylamino-methyl)-benzoic acid

A solution of 3-cyanobenzoic acid (4.9 g, 33 mmol) in methanol (75 mL), concentrated hydrochloric acid (5 mL) and 10% palladium on carbon (0.5 g) were combined and hydrogenated at about 45 psi hydrogen on a Parr® shaker for a about 2 days. The mixture was then filtered though a bed of diatomaceous earth. The diatomaceous earth was washed with ethanol, and the filtrate was concentrated in vacuo to give the de-benzylated amine. Two of the above alkylation/reductions were combined and purified by silica gel chromatography using 1:1 ethyl acetate/hexanes to ethyl acetate to 1:9 methanol/ethyl acetate as eluent and yielded crude 3-aminomethylbenzoic acid (5.9 g): +APcI (M+1)$^+$152; $^1$H NMR=400 MHz (methanol-d$_4$) δ: 8.20–7.45 (arom, m, 4H), 4.16 (CH$_2$NH$_2$, s, 2H).

To a solution of the crude amino acid prepared above in dioxane/water (90 mL/45 mL) was added di-tert-butyl dicarbonate (12.9 g, 59 mmol), followed by dropwise addition of triethylamine (6.0 mL, 43 mmol). After stirring about 15 hours the reaction was concentrated under reduced pressure and then filtered through a plug of silica using 1:1 ethyl acetate/hexanes as an eluent to afford the title compound of part F as a colorless solid (5.6 g, 68%): $^1$H NMR=400 MHz (methanol-d$_4$) δ: 8.00–7.80 (arom, m, 2H), 7.55–7.35 (arom, m, 2H), 4.26 (CH$_2$NH, s, 2H), 1.44 (BOC, s, 9H).

G. 3-(tert-Butoxycarbonylamino-methyl)-benzoic acid 2,5-dioxo-pyrrolidin-1-yl ester A stirred solution of N-hydroxysuccinimide (0.92 g, 8.0 mmol), the title compound of part F (197 g, 0.969 mol), and 1-(3-dimethylaminopropyl)-3-ethylcarbodiimide (1.00 g, 4.0 mmol) in anhydrous dichloromethane (15 mL) was stirred at room temperature for about 18 h under nitrogen atmosphere. The reaction mixture was extracted two times with saturated sodium bicarbonate solution and then brine. The organic layer was dried over sodium sulfate, filtered, concentrated in vacuo and then chromatographed using 3:1 to 1:1 hexanes/ethyl acetate to give the title compound of part G as a colorless solid (0.82 g, 59%): $^1$H NMR=400 MHz (methanol-d$_4$)) δ: 8.03 (arom, s, 1H), 7.99 (arom, d, 1H), 7.65 (arom, d, 1H), 7.53 (arom, t, 1H), 4.30 (CH$_2$NH, s, 2H), 2.88 (CH$_2$CH$_2$, s, 4H), 1.44 (BOC, s, 9H).

H. 3-Benzyloxy-2(R)-[3-(tert-butoxycarbonylamino-methyl)-benzoylamino]-propionic acid A stirred solution of D-O-benzylserine (449 mg, 2.30 mmol), the title compound of part G (824 mg, 2.30 mmol), and triethylamine (0.96 mL, 6.9 mmol) in dioxane/water (20 mL/4 mL) was heated to about 45° C. for about 18 hours. The reaction mixture was then concentrated to half volume in vacuo, ethyl acetate (10 mL) and water (10 mL) were added, and the aqueous layer was acidified to pH 3 using 1 N aqueous hydrochloric acid. The mixture was extracted with ethyl acetate, the combined organic layers were dried over anhydrous sodium sulfate, filtered and concentrated in vacuo to give the title compound of part H as a viscous, yellow oil (1.1 g, quant): $^1$H NMR=400 MHz (CDCL$_3$) δ7.80–7.00 (arom, ser. of m, 9H), 5.00 (NH, br s, 1H), 4.94 (CHCO$_2$H, m, 1H), 4.55 (br s, 2H), 4.34 (br s, 2H), 4.03 (m, 1H), 3.81 (m, 1H), 1.44 (BOC, s, 9H).

I. (3-{1(R)-Benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethylcarbamoyl}-benzyl)-carbamic acid tert-butyl ester The title compound of part E (50 mg, 0.10 mmol) was dissolved into 1 mL ethyl acetate, cooled to about 0° C., and triethylamine (0.12 mL, 0.84 mmol) was then added. After stirring for 15 min a solution of the title compound of part H (45 mg, 0.10 mmol) in ethyl acetate (0.5 mL) and 1-propanephosphonic acid cyclic anhydride (0.14 mL, 0.21 mmol) were added and the mixture was stirred about 1 hour. Saturated aqueous sodium bicarbonate was added and the product was extracted with ethyl acetate (3×25 mL). The combined extracts were dried over sodium sulfate, concentrated under reduced pressure, and then purified by silica gel chromatography employing 1:1 hexanes/ethyl acetate to ethyl acetate as eluents to give the title compound of part I (15 mg, 19%) as a colorless oil: +APcI MS (M+1)$^+$739, (M+1).

J. 3-Aminomethyl-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-benzamide To a solution of the title compound of part I (15 mg, 0.020 mmol) in ethanol (1 mL) cooled to about 0° C. was added concentrated hydrochloric acid (1 mL). After about 15 hours at 0° C. the reaction was concentrated under reduced pressure, concentrated two more times from ethanol, and then triturated from ether to afford the title compound of part J (14 mg, quant): +APcI MS (M+1)$^+$639; $^1$H NMR=400 MHz (CD$_3$OD) δ: 8.83–7.25 (series of m, 13H), 3.70 (d, 1H), 3.14 (m, 1H), 1.61 (br s, 6H).

EXAMPLES TWO–TWENTY-ONE

The compounds of Examples Two through Twenty-one are prepared from the appropriate starting materials in a manner analogous to the method of Example One.

Example Two

4-Amino-but-2-enoic acid (2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-amide.

Example Three

4-Amino-pent-2-enoic acid (2-(3a-benzyl-2-methyl-3-oxo-2,3,3a,4,6,7-hexaydro-pyrazolo[4,3-c]pyridin-5-yl)-1-benzyloxymethyl-2-oxo-ethyl)-amide.

Example Four

4-Amino-4-methyl-pent-2-enoic acid (2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-amide.

Example Five

3-Aminomethyl-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide.

Example Six 3-(1-Amino-ethyl)-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide.

Example Seven 3-(1-Amino-1-methyl-ethyl)-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide.

Example Eight 3-(1-Amino-1-methyl-ethyl)-N-(2-(3a-benzyl-03-oxo-2,3,3a,4,6,7-hexahydro-pyrazolo[4,3-c]pyridin-5-yl)-1-benzyloxymethyl-2-oxo-ethyl)-benzamide.

Example Nine 3-(1-Amino-1-methyl-ethyl)-N-(2-(3a-benzyl-2-methyl-3-oxo-2,3,3a,4,6,7-hexahydro-pyrazolo[4,3-c]pyridin-5-yl)-1-(1H-indol-3-ylmethyl)-2-oxo-ethyl)-benzamide.

Example Ten 3-(1-Amino-1-methyl-ethyl)-N-(2-(3a-pyridin-2-ylmethyl-2-(2,2,2-trifluoro-ethyl)-3-oxo-2,3,3a,4,6,7-hexahydro-pyrazolo[4,3-c]pyridin-5-yl)-1-(2,4-difluorobenzyloxymethyl)-2-oxo-ethyl)-benzamide.

Example Eleven

3-Aminomethyl-N-(1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide.

Example Twelve 3-(1-Amino-ethyl)-N-(1-(2,4-difluoro-benzyloxymethyl)-2-(1,3-dioxo-8a-pyridin-2-ylmethyl-2(2,2,2-trifluoro-ethyl)-hexahydro-imidazo[1,5-a]pyrazin-7-yl)-20oxo-ethyl)-benzamide.

Example Thirteen 3-(1-Amino-1-methyl)-N-(1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide.

Example Fourteen

4-Amino-but-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

Example Fifteen

4-Amino-pent-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

Example Sixteen

4-Amino-4-methyl-pent-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

Example Seventeen 3-(1-Amino-ethyl)-N-(benzyloxymethyl-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide.

Example Eighteen 3-(1-Amino-1-methyl-ethyl)-N-(benzyloxymethyl-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide.

Example Nineteen

4-Amino-but-2-enoic acid (1-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

Example Twenty

4-Amino-pent-2-enoic acid (1-(benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

Example Twenty-one

4-Amino-4-methyl-pent-2-enoic acid (1-(benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

What is claimed is:
1. A kit comprising:
a. a first compound of the Formula I:

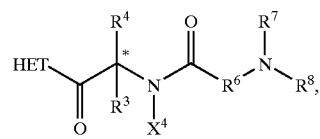

or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein:
HET is the heterocyclic moiety

[structure with COOH, Y, X, Q, N, R¹]

Q is a covalent bond or CH$_2$;
X is CR$^9$R$^{10}$, C=CH$_2$ or C=O;
Y is CR$^9$R$^{10}$, O or NR$^2$;
Z is C=O, C=S or S(O)$_2$;
R$^1$ is hydrogen, —CN, —(CH$_2$)$_q$N(X$^6$)C(O)X$^6$, —(CH$_2$)$_q$N(X$^6$)C(O)(CH$_2$)$_t$—A$^1$, —(CH$_2$)$_q$N(X$^6$)S(O)$_2$(CH$_2$)$_t$—A$^1$, —(CH$_2$)$_q$N(X$^6$)S(O)$_2$X$^6$, —(CH$_2$)$_q$N(X$^6$)C(O)N(X$^6$)(CH$_2$)$_t$—A$^1$, —(CH$_2$)$_q$N(X$^6$)C(O)N(X$^6$)(X$^6$), —(CH$_2$)$_q$C(O)N(X$^6$)(X$^6$), —(CH$_2$)$_q$C(O)N(X$^6$)(CH$_2$)$_t$—A$^1$, —(CH$_2$)$_q$C(O)OX$^6$, —(CH$_2$)$_q$C(O)O(CH$_2$)$_t$—A$^1$, —(CH$_2$)$_q$OX$^6$, —(CH$_2$)$_q$OC(O)X$^6$, —(CH$_2$)$_q$OC(O)(CH$_2$)$_t$A$^1$, —(CH$_2$)$_q$OC(O)N(X$^6$)(CH$_2$)$_t$—A$^1$, —(CH$_2$)$_q$OC(O)N(X$^6$)(X$^6$), —(CH$_2$)$_q$C(O)X$^6$, —(CH$_2$)$_q$C(O)(CH$_2$)$_t$—A$^1$, —(CH$_2$)$_q$C(O)OX$^8$, —(CH$_2$)$_q$N(X$^6$)S(O)$_2$N(X$^6$)(X$^6$), —(CH$_2$)$_q$S(O)$_m$X$^6$, —(CH$_2$)$_q$S(O)$_m$(CH$_2$)$_t$—A$^1$, —(C$_1$–C$_{10}$)alkyl, —(CH$_2$)$_t$—A$^1$, —(CH$_2$)$_q$—(C$_3$–C$_7$)cycloalkyl, (CH$_2$)$_q$—Y$^1$—(C$_1$–C$_6$)alkyl, —(CH$_2$)$_q$—Y$^1$—(CH$_2$)$_t$—A$^1$ or —(CH$_2$)$_q$—Y$^1$—(CH$_2$)$_t$—(C$_3$–C$_7$)cycloalky-I;
where the alkyl and cycloalkyl groups in the definition of R$^1$ are optionally substituted with (C$_1$–C$_4$)alkyl, hydroxy, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl or 1, 2 or 3 fluoro groups;
Y$^1$ is O, S(O)$_m$, —C(O)NX$^6$—, —CH=CH—, —C≡C—, —N(X$^6$)C(O)—, —C(O)NX$^6$—, —C(O)O—, —OC(O)N(X$^6$)— or —OC(O)—;
q is 0, 1, 2, 3 or 4;
t is 0, 1, 2 or 3;
said (CH$_2$)$_q$ group and (CH$_2$)$_t$ group in the definition of R$^1$ are optionally independently substituted with hydroxy, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl, 1, 2 or 3 fluoro groups or 1 or 2 (C$_1$–C$_4$)alkyl groups;
R$^2$, for each occurrence, is hydrogen, (C$_1$–C$_8$)alkyl, —(C$_0$–C$_3$)alkyl-(C$_3$–C$_8$)cycloalkyl, —(C$_1$–C$_4$)alkyl-A$^1$ or A$^1$;
where the alkyl groups and the cycloalkyl groups in the definition of R$^2$ are optionally substituted with hydroxy, —C(O)OX$^6$, —C(O)N(X$^6$)(X$^6$), —N(X$^6$)(X$^6$), —S(O)$_m$(C$_1$–C$_6$)alkyl, —C(O)A$^1$, —C(O)(X$^6$), CF$_3$, CN or 1, 2 or 3 independently selected halogens;
R$^3$ is selected from the group consisting of A$^1$, (C$_1$–C$_{10}$)alkyl, —(C$_1$–C$_6$)alkyl-A$^1$, —(C$_1$–C$_6$)alkyl-(C$_3$–C$_7$)cycloalkyl, —(C$_1$–C$_5$)alkyl-X$^1$—(C$_1$–C$_5$)alkyl, —(C$_1$–C$_5$)alkyl-X$^1$—(C$_0$–C$_5$)alkyl-A$^1$ and —(C$_1$–C$_5$)alkyl-X$^1$—(C$_1$–C$_5$)alkyl-(C$_3$–C$_7$)cycloalkyl;
where the alkyl groups in the definition of R$^3$ are optionally substituted with —S(O)$_m$(C$_1$–C$_6$)alkyl, —C(O)OX$^3$, 1, 2, 3, 4 or 5 independently selected halogens or 1, 2 or 3 independently selected —OX$^3$ groups; X$^1$ is O, S(O)$_m$, —N(X$^2$)C(O)—, —C(O)N(X$^2$)—, —OC(O)—, —C(O)O—, —CX$^2$=CX$^2$—, —N(X$^2$)C(O)O—, —OC(O)N(X$^2$)— or —C≡C—;
R$^4$ is hydrogen, (C$_1$–C$_6$)alkyl or (C$_3$–C$_7$)cycloalkyl, or R$^4$ is taken together with R$^3$ and the carbon atom to which they are attached and form (C$_5$–C$_7$)cycloalkyl, (C$_5$–C$_7$) cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;
X$^4$ is hydrogen or (C$_1$–C$_6$)alkyl or X$^4$ is taken together with R$^4$ and the nitrogen atom to which X$^4$ is attached and the carbon atom to which R$^4$ is attached and form a five to seven membered ring;
R$^6$ is —(CR$^a$R$^b$)$_a$—E—(CR$^a$R$^b$)$_b$—, where the —(CR$^a$R$^b$)$_a$— group is attached to the carbonyl carbon of the amide group of the compound of formula I and the —(CR$^a$R$^b$)$_b$ group is attached to the terminal nitrogen atom of the compound of formula I;
E is —O—, —S—, —CH=CH— or an aromatic moiety selected from

[aromatic ring structures: benzene, pyridine, pyrimidine, naphthalene, thiophene, imidazole, thiazole]

said aromatic moiety in the definition of E optionally substituted with up to three halo, hydroxy, —N(R$^c$)(R$^c$), (C$_1$–C$_6$)alkyl or (C$_1$–C$_6$)alkoxy;
R$^a$ and R$^b$ are, for each occurrence, independently hydrogen, (C$_1$–C$_6$)alkyl, trifluoromethyl, phenyl or monosubstituted (C$_1$–C$_6$)alkyl where the substituents are imidazolyl, naphthyl, phenyl, indolyl, p-hydroxyphenyl, —OR$^c$, S(O)$_m$R$^c$, C(O)OR$^c$, (C$_3$–C$_7$)cycloalkyl, —N(R$^c$)(R$^c$), or —C(O)N(R$^c$)(R$^c$);
R$^c$, for each occurrence, is independently hydrogen or (C$_1$–C$_6$)alkyl;
a and b are independently 0, 1, 2 or 3, with the proviso that if E is —O— or —S— then b is 2 or 3, and with the further proviso that if E is —CH=CH— then b is 1, 2 or 3;
R$^7$ and R$^8$ are each independently hydrogen or optionally substituted (C$_1$–C$_6$)alkyl;
where the optionally substituted (C$_1$–C$_6$)alkyl in the definition of R$^7$ and R$^8$ is optionally independently substituted with A$^1$, —C(O)O—(C$_1$–C$_6$)alkyl, —S(O)$_m$(C$_1$–C$_6$)alkyl, 1 to 5 halogens, 1 to 3 hydroxy groups, 1 to 3 —O—C(O)(O)(C$_1$–C$_{10}$)alkyl groups or 1 to 3 (C$_1$–C$_6$)alkoxy groups; or
R$^7$ and R$^8$ can be taken together to form —(CH$_2$)$_r$—L—(CH$_2$)$_r$—;
where L is C(X$^2$)(X$^2$), S(O)$_m$ or N(X$^2$);
R$^9$ and R$^{10}$ are each independently selected from the group consisting of hydrogen, fluoro, hydroxy and $(C_1-C_5)$alkyl optionally independently substituted with 1–5 halogens;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, QCF$_3$, OCF$_2$H, CF$_3$, CH$_3$, OCH$_3$, —OX$^5$, —C(O)N(X$^6$)(X$^6$), —C(O)OX$^6$, oxo, $(C_1-C_6)$alkyl, nitro, cyano, benzyl, —S(O)$_m$(C$_1$–C$_6$)alkyl, 1H-tetrazol-5-yl, phenyl, phenoxy, phenylalkyloxy, halophenyl, methylenedioxy, —N(X$^6$)(X$^6$), —N(X$^6$)C(O)(X$^6$), —S(O)$_2$N(X$^6$)(X$^6$), —N(X$^6$)S(O)$_2$-phenyl, —N(X$^6$)S(O)$_2$X$^6$, —CONX$^{11}$X$^{12}$, —S(O)$_2$NX$^{11}$X$^{12}$, —NX$^6$S(O)$_2$X$^{12}$, —NX$^6$CONX$^{11}$X$^{12}$, —NX$^6$S(O)$_2$NX$^{11}$X$^{12}$, —NX$^6$C(O)X$^{12}$, imidazolyl, thiazolyl and tetrazolyl, provided that if $A^1$ is optionally substituted with methylenedioxy then it can only be substituted with one methylenedioxy;

where $X^{11}$, for each occurrence, is independently hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$ alkoxycarbonyl, —S(O)$_m$(C$_1$–C$_6$)alkyl, 1 to 5 halogens, 1 to 3 hydroxy groups, 1 to 3 $(C_1-C_{10})$alkanoyloxy groups or 1 to 3 $(C_1-C_6)$ alkoxy groups;

$X^{12}$, for each occurrence, is independently hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, CH$_3$, OCH$_3$, OCF$_3$ and CF$_3$;

or $X^{11}$ and $X^{12}$ are taken together to form —(CH$_2$)$_r$—L$^1$—(CH$_2$)$_r$—;

L$^1$ is C(X$^2$)(X$^2$), O, S(O)$_m$ or N(X$^2$);

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with —S(O)$_m$(C$_1$–C$_6$)alkyl, —C(O)OX$^3$, 1 to 5 halogens or 1–3 OX$^3$ groups;

$X^3$ for each occurrence is independently hydrogen or $(C_1-C_6)$alkyl;

$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, CONH$_2$, —S(O)$_m$(C$_1$–C$_6$)alkyl, carboxylate $(C_1-C_4)$ alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or NX$^7$ as a ring member;

$X^7$ is hydrogen or $(C_1-C_6)$alkyl optionally substituted with hydroxy;

m for each occurrence is independently 0, 1 or 2;

with the proviso that:
$X^6$ and $X^{12}$ cannot be hydrogen when attached to C(O) or S(O)$_2$ in the form C(O)X$^6$, C(O)X$^{12}$, S(O)$_2$X$^6$ or S(O)$_2$X$^{12}$;

b. a second compound selected from group consisting of a selective estrogen receptor modulator (SERM); calcitonin; a functional somatostatin antagonist; a bisphosphonate; estrogen or conjugated estrogens; a β$_3$ adrenergic receptor agonist; and a growth hormone secretagogue selected from the group consisting of GHRP-6, Hexarelin, GHRP-1, growth hormone releasing factor (GRF), IGF-1, IGF-2 and B-HT920 or an analog thereof; and a pharmaceutically acceptable carder or diluent in a second unit dosage form; and c. a container.

2. A kit of claim 1 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $X^4$ is hydrogen;

$R^4$ is hydrogen or methyl;

$R^7$ is hydrogen or $(C_1-C_3)$alkyl; and $R^8$ is hydrogen or $(C_1-C_3)$alkyl optionally substituted with up to two hydroxyl groups.

3. A kit of claim 2 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^1$ is —(CH$_2$)$_t$—A$^1$, —(CH$_2$)$_q$—(C$_3$–C$_7$)cycloalkyl or $(C_1-C_{10})$alkyl;

where A$^1$ in the definition of $R^1$ is optionally substituted with up to three substituents, each substituent being independently selected from the group consisting of fluoro, chloro, methyl, methoxy, trifluoromethoxy, difluoromethoxy and trifluoromethyl; and the cycloalkyl and alkyl groups in the definition of $R^1$ are optionally substituted with $(C_1-C_4)$alkyl, hydroxyl, $(C_1-C_4)$alkoxy, carboxyl, CONH$_2$, —S(O)$_m$(C$_1$–C$_6$) alkyl, —CO$_2$(C$_1$–C$_4$alkyl ester, 1H-tetrazol-5-yl or up to 3 fluoro.

4. A kit of claim 3 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein Z is C=O; is a covalent bond; X is C=O; $R^2$ is H, methyl, ethyl or trifluoroethyl; $R^1$ is $A^1$—$CH_2$—, where $A^1$ in the definition of $R^1$ is phenyl or pyridyl where said phenyl or pyridyl is optionally substituted with up to three substituents, each substituent being independently selected from the group consisting of fluoro, chloro, methyl, methoxy, difluoromethoxy, trifluoromethoxy and trifluoromethyl; and $R^3$ is phenyl-$CH_2$—O—$CH_2$—, pyridyl-$CH_2$—O—$CH_2$—, phenyl-$(CH_2)_3$—, 3-indolyl-$CH_2$—, alpha-naphthy($C_1$-$C_4$)alkyl or thiazolyl-$CH_2$—O—$CH_2$—, wherein the aryl portion of the groups defined for $R^3$ is optionally substituted with up to three substituents, each substituent being independently selected from the group consisting of fluoro, chloro, methyl, methoxy, difluoromethoxy, trifluoromethoxy and trifluoromethyl; and Y is $NR^2$.

5. A kit of claim 4 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein $R^1$ is phenyl-$CH_2$— or pyridyl-$CH_2$—; $R^2$ is methyl, ethyl or trifluoroethyl; $R^3$ is phenyl-$CH_2$—O—$CH_2$—, 3-indolyl-methyl or 2,4-difluorobenzyloxymethyl; $R^4$, $X^4$, $R^7$ and $R^8$ are each hydrogen; $R^a$ is hydrogen or methyl; $R^b$ is hydrogen or methyl; a is 0; b is 1; and E is metaphenylene or vinylene.

6. A kit of claim 5 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, selected from the group consisting of: 3-aminomethyl-N-(1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 3-(1-amino-ethyl)-N-(1-(2,4-difluoro-benzyloxymethyl)-2-(1,3-dioxo-8a-pyridin-2-ylmethyl-2(2,2,2-trifluoro-ethyl)-hexahydro-imidazo[1,5-a]pyrazin-7-yl)-2-oxo-ethyl)-benzamide; 3-(1-amino-1-methyl-N-(1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 4-amino-but-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; 4-amino-pent-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; 4-amino-4-methyl-pent-2-enoic acid (1-(2,4-difluoro-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; 3-aminomethyl-N-(2-(1,3-dioxo-8a-pyridin-2-ylmethyl-2-(2,2,2-trifluoro-ethyl)-hexahydro-imidazo[1,5-a]pyrazin-7-yl)-1-benzyloxymethyl-2-oxo-ethyl)-benzamide; 3-(1-amino-ethyl)-N-(benzyloxymethyl-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 3-(1-amino-1-methyl-ethyl-N-(benzyloxymethyl-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-benzamide; 4-amino-but-2-enoic acid (1-benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; 4-amino-pent-2-enoic acid (1-(benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide; and 4-amino-4-methyl-pent-2-enoic acid (1-(benzyloxymethyl)-2-(1,3-dioxo-8a-pyridin-2-ylmethyl-2-(2,2,2-trifluoro-ethyl)-hexahydro-imidazo[1,5-a]pyrazin-7-yl)-2-oxo-ethyl)-amide.

7. A kit of claim 1 wherein the second compound is a bisphosphonate.

8. A kit of claim 7 wherein the bisphosphonate is alendronate or ibandronate.

9. A kit of claim 1 wherein the second compound is a selective estrogen receptor modulator (SERM).

10. A kit of claim 9 wherein the SERM is tamoxifen, droloxifene, raloxifene, idoxifene; cis-6-(4-fluoro-phenyl)-5-[4-(2-piperidin-1-yl-ethoxy)-phenyl]-5,6,7,8-tetrahydro-naphthalene-2-ol; (−)-cis-6-phenyl-5-[4-(2-pyrrolidin-1-yl-ethoxy)-phenyl]-5,6,7,8-tetrahydro-naphthalene-2-ol; cis-6-phenyl-5-[4-(2-pyrrolidin-1-yl-ethoxy)-phenyl]-5,6,7,8-tetrahydro-naphthalene-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydro-isoquinoline.

11. A kit of claim 1 wherein the second compound is a growth hormone secretagogue selected from the group consisting of GHRP-6, Hexarelin, GHRP-1, growth hormone releasing factor (GAF), IGF-1, IGF-2 and B-HT920 or an analog thereof.

12. A kit comprising:
a. a first compound of the Formula I:

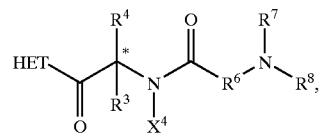

I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein:

HET is a heterocyclic moiety selected from the group consisting of

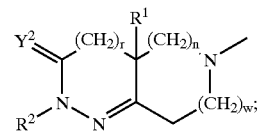

f is 0 or 1;
n and w are each 1;
$Y^2$ is oxygen;

R¹ is $(C_1-C_{10})$alkyl, —$(CH_2)_t$—A¹, or —$(CH_2)_q$—$(C_3-C_7)$cycloalkyl;

where the alkyl and cycloalkyl groups in the definition of R¹ are optionally substituted with $(C_1-C_4)$ alkyl, hydroxy, $(C_1-C_4)$alkoxy, carboxyl, —$CONH_2$, —$S(O)_m(C_1-C_6)$alkyl, —$CO_2(C_1-C_4)$ alkyl ester, 1H-tetrazol-5-yl or 1, 2 or 3 fluoro groups;

q is 0, 1, 2, 3 or 4;

t is 0, 1, 2 or 3;

R² is hydrogen, $(C_1-C_8)$alkyl, —$(C_0-C_3)$alkyl-$(C_3-C_8)$ cycloalkyl, or phenyl;

where the $(C_1-C_8)$alkyl group in the definition of R² is optionally substituted with hydroxy, $CF_3$, or 1, 2 or 3 independently selected halogens;

R³ is phenyl-$CH_2$—O—$CH_2$—, phenyl-$CH_2$—$CH_2$—$CH_2$—, naphthyl-$CH_2$, 3-indolyl-methyl; said phenyl being optionally substituted with up to three fluoro or chloro;

R⁴ is hydrogen or methyl:

X⁴ is hydrogen;

R⁶ is —$(CR^aR^b)_a$—E—$(CR^aR^b)_b$—, where the —$(CR^aR^b)_a$— group is attached to the carbonyl carbon of the amide group of the compound of formula I and the —$(CR^aR^b)_b$ group is attached to the terminal nitrogen atom of the compound of formula I;

E is —CH=CH— or an aromatic moiety selected from

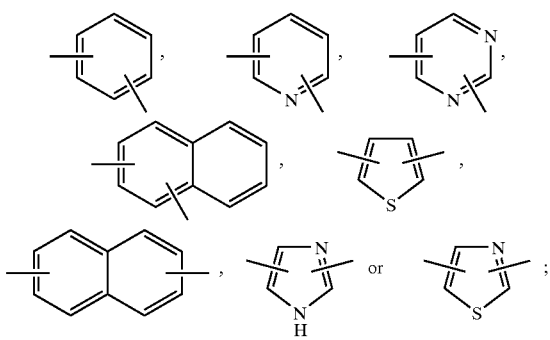

said aromatic moiety in the definition of E optionally substituted with up to three halo, hydroxy, —$N(R^c)(R^c)$, $(C_1-C_6)$alkyl or $(C_1-C_6)$alkoxy;

$R^a$ and $R^b$ are, for each occurrences, independently hydrogen or methyl;

$R^c$, for each occurrence, is independently hydrogen or $(C_1-C_6)$alkyl;

a and b are independently 0, 1, 2 or 3;

R⁷ and R⁸ are each independently hydrogen or $(C_1-C_3)$ alkyl optionally substituted with up to two hydroxyl groups;

A¹ is phenyl, pyridyl or thiazolyl;

A¹ in the definition of R¹ is optionally substituted with up to three substituents, each substituent independently selected from the group consisting of F, Cl, $OCF_3$, $OCF_2H$, $CF_3$, $CH_3$, or $OCH_3$;

m for each occurrence is independently 0, 1 or 2;

b. a second compound selected from group consisting of a selective estrogen receptor modulator (SERM); calcitonin; a functional somatostatin antagonist; a bisphosphonate; estrogen or conjugated estrogens; a β₃ adrenergic receptor agonist; and a growth hormone secretagogue selected from the group consisting of GHRP-6, Hexarelin, GHRP-1, growth hormone releasing factor (GRF), IGF-1, IGF-2 and B-HT920 or an analog thereof; and a pharmaceutically acceptable carrier or diluent in a second unit dosage form; and c. a container.

13. A kit of claim 12 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein n and w are each 1; f is 0; R² is H, methyl, ethyl or trifluoroethyl and R¹ is phenyl-$CH_2$—, pyridyl-$CH_2$— or thiazolyl-$CH_2$.

14. A kit of claim 13 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein R⁷ and R⁸ are each hydrogen; R⁴ is hydrogen; a is 0; b is 1; and E is vinylene or metaphenylene.

15. A kit of claim 14 wherein the first compound is of Formula I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, selected from 4-amino-but-2-enoic acid (2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-amide; 4-amino-pent-2-enoic acid (2-(3a-benzyl-2-methyl-3-oxo-2,3,3a,4,6,7-hexaydro-pyrazolo[4,3-c]pyridin-5-yl)-1-benzoyloxymethyl-2-oxo--ethyl)-amide; 4-amino-4-methyl-pent-2-enoic acid (2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-amide; 3-aminomethyl-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide; 3-(1-amino-ethyl)-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide; 3-(1-amino-1-methyl-ethyl)-N-(2-(3a-benzyl-2-methyl-3-oxo-2,3,3a,4,6,7-hexahydro-pyrazolo[4,3-c]pyridin-5-yl)-1-benzyloxymethyl-2-oxo-ethyl)-benzamide; 3-(1-amino-1-methyl-ethyl)-N-(2-(3a-benzyl-03-oxo-2,3,3a,4,6,7-hexahydro-pyrazolo[4,3-c]pyridin-5-yl)-1-benzyloxymethyl-2-oxo-ethyl)-benzamide; 3-(1-amino-1-methyl-ethyl)-N-(2-(3a-benzyl-2-methyl-3-oxo-2,3,3a,4,6,7-hexahydro-pyrazolo[4,3-c]pyridin-5-yl)-1-(1H-indol-3-ylmethyl)-2-oxo-ethyl)-benzamide; and 3-(1-amino-1-methyl-ethyl)-N-(2-(3a-pyridin-2-ylmethyl-2-(2,2,2-trifluoro-ethyl)-3-oxo-2,3,3a,4,6,7-hexahydro-pyrazolo[4,3-c]pyridin-5-yl)-1-(2,4-difluorobenzyloxymethyl)-2-oxo-ethyl)-benzamide.

16. A kit of claim 12 wherein the second compound is a bisphosphonate.

17. A kit of claim 16 wherein the bisphosphonate is alendronate or ibandronate.

18. A kit of claim 12 wherein the second compound is a selective estrogen receptor modulator (SERM).

19. A kit of claim 18 wherein the SERM is tamoxifen, droloxifene, raloxifene, idoxifene; cis-6-(4-fluoro-phenyl)-5-[4-(2-piperidin-1-yl-ethoxy)-phenyl]-5,6,7,8-tetrahydro-naphthalene-2-ol; (−)-cis-6-phenyl-5-[4-(2-pyrrolidin-1-yl-ethoxy)-phenyl]-5,8,7,8-tetrahydro-naphthalene-2-ol; cis-6-phenyl-5-[4-(2-pyrrolidin-1-yl-ethoxy)-phenyl]-5,6,7,8-tetrahydro-naphthalene-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydro-isoquinoline.

20. A kit of claim 12 wherein the second compound is a growth hormone secretagogue selected from the group consisting of GHRP-6, Hexarelin, GHRP-1, growth hormone releasing factor (GRF), IGF-1, IGF-2 and B-HT920 or an analog thereof.

* * * * *